United States Patent
Ashraf et al.

(10) Patent No.: US 12,161,539 B2
(45) Date of Patent: *Dec. 10, 2024

(54) STRETCH LAMINATE WITH BEAMED ELASTICS AND FORMED NONWOVEN LAYER

(71) Applicant: The Procter & Gamble Company, Cincinnati, OH (US)

(72) Inventors: Arman Ashraf, Mason, OH (US); Gary Dean LaVon, Liberty Township, OH (US); Bret Darren Seitz, West Chester, OH (US); Sarah Marie Wade, Springfield Township, OH (US); Joseph Allen Eckstein, Sunman, IN (US); Vanessa Marie Melendez, Cincinnati, OH (US); Elizabeth Jo Bruns, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 301 days.

This patent is subject to a terminal disclaimer.

(21) Appl. No.: 17/935,951

(22) Filed: Sep. 28, 2022

(65) Prior Publication Data

US 2023/0036659 A1 Feb. 2, 2023

Related U.S. Application Data

(63) Continuation of application No. 16/445,838, filed on Jun. 19, 2019, now Pat. No. 11,547,613, which is a
(Continued)

(51) Int. Cl.
*A61F 13/49* (2006.01)
*A61F 13/15* (2006.01)
(Continued)

(52) U.S. Cl.
CPC .... *A61F 13/4902* (2013.01); *A61F 13/15699* (2013.01); *A61F 13/15764* (2013.01);
(Continued)

(58) Field of Classification Search
CPC B32B 5/04; B32B 2262/0207; D04H 13/001; A61F 13/4902; A61F 13/15699;
(Continued)

(56) References Cited

U.S. PATENT DOCUMENTS

| 1,065,525 A | 6/1913 | Henkel |
| 3,113,225 A | 12/1963 | Claus |

(Continued)

FOREIGN PATENT DOCUMENTS

| CA | 2158790 A1 | 3/1996 |
| CN | 1107738 A | 9/1995 |

(Continued)

OTHER PUBLICATIONS

Extended EPO Search Report and Opinion, Application No. 23204254.9 dated Feb. 6, 2024, 07 pages.
(Continued)

*Primary Examiner* — Susan S Su
(74) *Attorney, Agent, or Firm* — Christian M. Best

(57) ABSTRACT

A stretch laminate is disclosed. The stretch laminate may include a layer of nonwoven material that includes an accumulation of filaments and has an inner surface and an outer surface, the outer surface having an ordered arrangement of zones, each zone having an attenuated region adjacent to a build-up region wherein the attenuated region has a first basis weight and the build-up region has a second basis weight greater than the first basis weight, the difference in basis weights corresponding to disposition of the filaments according to the ordered arrangement. The stretch laminate may include a plurality of elastic strands space
(Continued)

apart from each other in a crotch-stretch direction. In some examples the elastic strands may have an Average Strand Spacing no greater than 3 mm and/or an Average Decitex no greater than 300, and/or an Average Pre-Strain no greater than 250 percent.

16 Claims, 18 Drawing Sheets

Related U.S. Application Data continuation-in-part of application No. 15/846,349, filed on Dec. 19, 2017, now Pat. No. 11,000,426, and a continuation-in-part of application No. 15/846,745, filed on Dec. 19, 2017, now abandoned, and a continuation-in-part of application No. 15/838,405, filed on Dec. 12, 2017, now Pat. No. 11,219,555, and a continuation-in-part of application No. 15/833,057, filed on Dec. 6, 2017, now Pat. No. 11,147,717, and a continuation-in-part of application No. 15/832,929, filed on Dec. 6, 2017, now Pat. No. 11,141,321, and a continuation-in-part of application No. 15/831,448, filed on Dec. 5, 2017, now Pat. No. 10,973,699, and a continuation-in-part of application No. 15/831,464, filed on Dec. 5, 2017, now Pat. No. 11,642,249.

(60) Provisional application No. 62/687,031, filed on Jun. 19, 2018.

(51) Int. Cl.
*B32B 5/04* (2006.01)
*A61F 13/84* (2006.01)
*D04H 13/00* (2006.01)

(52) U.S. Cl.
CPC .............. *A61F 2013/15406* (2013.01); *A61F 2013/15943* (2013.01); *A61F 2013/49022* (2013.01); *A61F 2013/8497* (2013.01); *B32B 5/04* (2013.01); *B32B 2262/0207* (2013.01); *D04H 13/001* (2013.01)

(58) Field of Classification Search
CPC ...... A61F 13/15764; A61F 2013/15406; A61F 2013/15943; A61F 2013/49022; A61F 2013/8497; A61F 13/49013; A61F 13/19015; A61F 2013/49025; A61F 2013/49026; A61F 2013/49031–49034; A61F 2013/49038; A61F 2013/49039
See application file for complete search history.

(56) References Cited

U.S. PATENT DOCUMENTS

| | | |
|---|---|---|
| 3,423,266 A | 1/1969 | Davies et al. |
| 3,508,722 A | 4/1970 | Kohl |
| 3,562,041 A | 2/1971 | Robertson |
| 3,575,782 A | 4/1971 | Hansen |
| 3,692,618 A | 9/1972 | Dorschner et al. |
| 3,733,238 A | 5/1973 | Long |
| 3,802,817 A | 4/1974 | Matsuki et al. |
| 3,860,003 A | 1/1975 | Buell |
| 4,100,324 A | 7/1978 | Anderson et al. |
| 4,333,979 A | 6/1982 | Sciaraffa |
| 4,525,905 A | 7/1985 | Bogucki-land |
| 4,589,876 A | 5/1986 | Van Tilburg |
| 4,610,678 A | 9/1986 | Weisman |
| 4,673,402 A | 6/1987 | Weisman |
| 4,695,278 A | 9/1987 | Lawson |
| 4,704,115 A | 11/1987 | Buell |
| 4,741,941 A | 5/1988 | Englebert |
| 4,795,454 A | 1/1989 | Dragoo |
| 4,834,735 A | 5/1989 | Alemany |
| 4,854,984 A | 8/1989 | Ball |
| 4,888,231 A | 12/1989 | Angstadt |
| 4,909,803 A | 3/1990 | Aziz |
| 4,940,464 A | 7/1990 | Van Gompel |
| 4,970,104 A | 11/1990 | Radwanski |
| 5,003,676 A | 4/1991 | Mcfalls |
| 5,060,881 A | 10/1991 | Bogucki-land |
| 5,092,861 A | 3/1992 | Nomura |
| 5,110,403 A | 5/1992 | Ehlert |
| 5,167,897 A | 12/1992 | Weber |
| 5,246,433 A | 9/1993 | Hasse |
| 5,334,289 A | 8/1994 | Trokhan |
| 5,360,420 A | 11/1994 | Cook |
| 5,393,360 A | 2/1995 | Bridges |
| 5,413,849 A | 5/1995 | Austin |
| 5,508,102 A | 4/1996 | Georger et al. |
| 5,514,523 A | 5/1996 | Trokhan |
| 5,562,646 A | 10/1996 | Goldman |
| 5,569,234 A | 10/1996 | Buell |
| 5,575,874 A | 11/1996 | Griesbach, III |
| 5,599,335 A | 2/1997 | Goldman |
| 5,599,420 A | 2/1997 | Yeo |
| 5,628,097 A | 5/1997 | Benson |
| 5,643,588 A | 7/1997 | Roe |
| 5,643,653 A | 7/1997 | Griesbach, III |
| 5,669,894 A | 9/1997 | Goldman |
| 5,674,216 A | 10/1997 | Buell |
| 5,702,551 A | 12/1997 | Huber |
| 5,725,927 A | 3/1998 | Zilg et al. |
| 5,762,641 A | 6/1998 | Bewick-sonntag |
| 5,775,380 A | 7/1998 | Roelstraete |
| 5,858,504 A | 1/1999 | Fitting |
| 5,887,322 A | 3/1999 | Hartzheim |
| 5,895,623 A | 4/1999 | Trokhan |
| 5,897,545 A | 4/1999 | Kline |
| 5,916,661 A | 6/1999 | Benson |
| 5,957,908 A | 9/1999 | Kline |
| 5,964,973 A | 10/1999 | Heath et al. |
| 5,968,025 A | 10/1999 | Roe |
| 6,036,796 A | 3/2000 | Halbert |
| 6,043,168 A | 3/2000 | Colman |
| 6,107,537 A | 8/2000 | Elder |
| 6,107,539 A | 8/2000 | Palumbo |
| 6,118,041 A | 9/2000 | Roe |
| 6,120,487 A | 9/2000 | Ashton |
| 6,120,489 A | 9/2000 | Johnson |
| 6,139,941 A | 10/2000 | Jankevics |
| 6,153,209 A | 11/2000 | Vega |
| 6,248,195 B1 | 6/2001 | Schmitz |
| 6,291,039 B1 | 9/2001 | Combe |
| 6,319,239 B1 | 11/2001 | Daniels |
| 6,319,455 B1 | 11/2001 | Kauschke et al. |
| 6,331,268 B1 | 12/2001 | Kauschke et al. |
| 6,331,345 B1 | 12/2001 | Kauschke et al. |
| 6,361,638 B2 | 3/2002 | Takai |
| 6,383,431 B1 | 5/2002 | Dobrin |
| 6,395,957 B1 | 5/2002 | Chen |
| 6,410,129 B2 | 6/2002 | Zhang |
| 6,426,444 B2 | 7/2002 | Roe |
| 6,436,512 B1 | 8/2002 | Kauschke et al. |
| 6,508,641 B1 | 1/2003 | Kubik |
| 6,545,197 B1 | 4/2003 | Muller |
| 6,554,815 B1 | 4/2003 | Umebayashi |
| 6,586,652 B1 | 7/2003 | Roe |
| 6,617,016 B2 | 9/2003 | Zhang |
| 6,627,787 B1 | 9/2003 | Roe |
| 6,632,504 B1 | 10/2003 | Gillespie |
| 6,645,330 B2 | 11/2003 | Pargass |
| 6,673,418 B1 | 1/2004 | Deolivera |
| 6,676,054 B2 | 1/2004 | Heaney |
| 6,790,798 B1 | 9/2004 | Suzuki |
| 6,818,802 B2 | 11/2004 | Takai et al. |
| 6,821,301 B2 | 11/2004 | Azuse |
| 6,825,393 B2 | 11/2004 | Roe |
| 6,861,571 B1 | 3/2005 | Roe |
| 7,008,685 B2 | 3/2006 | Groitzsch |
| 7,118,558 B2 | 10/2006 | Wu |

(56) References Cited

U.S. PATENT DOCUMENTS

| | | |
|---|---|---|
| 7,306,582 B2 | 12/2007 | Adams |
| 7,465,367 B2 | 12/2008 | Day |
| 7,507,463 B2 | 3/2009 | Noda et al. |
| 7,553,535 B2 | 6/2009 | Noda et al. |
| 7,569,039 B2 | 8/2009 | Matsuda |
| 7,582,348 B2 | 9/2009 | Ando |
| 7,642,398 B2 | 1/2010 | Jaerpenberg |
| 7,662,462 B2 | 2/2010 | Noda et al. |
| 7,708,849 B2 | 5/2010 | Mccabe |
| 7,777,094 B2 | 8/2010 | Mori |
| 7,861,756 B2 | 1/2011 | Jenquin |
| 7,878,447 B2 | 2/2011 | Hartzheim |
| 7,897,240 B2 | 3/2011 | Noda et al. |
| 7,901,393 B2 | 3/2011 | Matsuda |
| 7,905,446 B2 | 3/2011 | Hartzheim |
| 7,954,213 B2 | 6/2011 | Mizutani |
| 7,955,549 B2 | 6/2011 | Noda et al. |
| 8,017,534 B2 | 9/2011 | Harvey et al. |
| 8,093,161 B2 | 1/2012 | Bansal |
| 8,143,177 B2 | 3/2012 | Noda |
| 8,183,431 B2 | 5/2012 | Noda et al. |
| 8,186,296 B2 | 5/2012 | Brown |
| 8,226,625 B2 | 7/2012 | Turner |
| 8,273,941 B2 | 9/2012 | Uematsu et al. |
| 8,304,600 B2 | 11/2012 | Noda et al. |
| 8,308,706 B2 | 11/2012 | Fukae |
| 8,377,554 B2 | 2/2013 | Martin |
| 8,388,594 B2 | 3/2013 | Turner |
| 8,440,043 B1 | 5/2013 | Schneider |
| 8,551,608 B2 | 10/2013 | Kawakami et al. |
| 8,574,209 B2 | 11/2013 | Nishitani et al. |
| 8,585,666 B2 | 11/2013 | Weisman |
| 8,647,319 B2 | 2/2014 | Een |
| 8,729,332 B2 | 5/2014 | Takahashi |
| 8,758,569 B2 | 6/2014 | Aberg et al. |
| 8,778,127 B2 | 7/2014 | Schneider |
| 8,853,108 B2 | 10/2014 | Ahoniemi |
| 8,865,965 B2 | 10/2014 | Sato et al. |
| 8,906,275 B2 | 12/2014 | Davis |
| 9,005,392 B2 | 4/2015 | Schneider |
| 9,039,855 B2 | 5/2015 | Schneider |
| 9,050,213 B2 | 6/2015 | Lavon |
| 9,095,477 B2 | 8/2015 | Yamaguchi et al. |
| 9,156,229 B2 | 10/2015 | Noda et al. |
| 9,156,648 B2 | 10/2015 | Yamamoto |
| 9,168,182 B2 | 10/2015 | Hargett |
| 9,198,804 B2 | 12/2015 | Nakamura |
| 9,205,005 B2 | 12/2015 | Kikuchi et al. |
| 9,226,861 B2 | 1/2016 | Lavon |
| 9,248,054 B2 | 2/2016 | Brown |
| 9,265,672 B2 | 2/2016 | Brown |
| 9,295,590 B2 | 3/2016 | Brown |
| 9,440,043 B2 | 9/2016 | Arora |
| 9,453,303 B2 | 9/2016 | Aberg |
| 9,486,371 B2 | 11/2016 | Wirtz et al. |
| 9,539,735 B2 | 1/2017 | Ferguson |
| 9,732,454 B2 | 8/2017 | Davis |
| 9,758,339 B2 | 9/2017 | Yanez, Jr. |
| 9,795,520 B2 | 10/2017 | Kaneko |
| 9,877,876 B2 | 1/2018 | Huang |
| 9,903,070 B2 | 2/2018 | Mourad et al. |
| 9,944,047 B2 | 4/2018 | Burt et al. |
| 10,190,244 B2 | 1/2019 | Ashraf |
| 10,577,722 B2 | 3/2020 | Ashraf et al. |
| 10,596,045 B2 | 3/2020 | Koshijima |
| 2001/0029141 A1 | 10/2001 | Mizutani |
| 2001/0030014 A1 | 10/2001 | Kwok |
| 2002/0004654 A1 | 1/2002 | Daniels et al. |
| 2002/0009940 A1* | 1/2002 | May ............... B32B 5/04 264/211.14 |
| 2002/0046802 A1 | 4/2002 | Tachibana |
| 2002/0103469 A1 | 8/2002 | Chen |
| 2002/0134067 A1 | 9/2002 | Heaney |
| 2002/0153271 A1 | 10/2002 | Mcmanus |
| 2002/0177829 A1 | 11/2002 | Fell |
| 2002/0193032 A1 | 12/2002 | Newkirk et al. |
| 2003/0078553 A1 | 4/2003 | Wada |
| 2003/0087056 A1 | 5/2003 | Ducker |
| 2003/0093045 A1 | 5/2003 | Erdman |
| 2003/0119404 A1 | 6/2003 | Belau |
| 2003/0125687 A1 | 7/2003 | Gubernick et al. |
| 2003/0144643 A1 | 7/2003 | Jarpenberg |
| 2003/0203162 A1 | 10/2003 | Fenwick |
| 2003/0203691 A1 | 10/2003 | Fenwick et al. |
| 2003/0211802 A1 | 11/2003 | Keck et al. |
| 2003/0233082 A1 | 12/2003 | Kline |
| 2004/0006323 A1 | 1/2004 | Hall |
| 2004/0059309 A1 | 3/2004 | Nortman |
| 2004/0097895 A1 | 5/2004 | Busam |
| 2004/0121120 A1 | 6/2004 | Gray |
| 2004/0127875 A1 | 7/2004 | Hammons et al. |
| 2004/0127883 A1 | 7/2004 | Cowell et al. |
| 2004/0133180 A1 | 7/2004 | Mori |
| 2004/0158212 A1 | 8/2004 | Ponomarenko |
| 2004/0158217 A1 | 8/2004 | Wu |
| 2004/0219854 A1 | 11/2004 | Groitzsch |
| 2004/0230171 A1 | 11/2004 | Ando |
| 2004/0254554 A1 | 12/2004 | Mavinkurve et al. |
| 2005/0013975 A1 | 1/2005 | Brock |
| 2005/0107764 A1 | 5/2005 | Matsuda |
| 2005/0136773 A1 | 6/2005 | Yahiaoui |
| 2005/0148971 A1 | 7/2005 | Kuroda et al. |
| 2005/0230037 A1 | 10/2005 | Jenquin |
| 2006/0047260 A1 | 3/2006 | Ashton |
| 2006/0069373 A1 | 3/2006 | Schlinz |
| 2006/0087053 A1 | 4/2006 | Odonnell |
| 2006/0089616 A1 | 4/2006 | Belau et al. |
| 2006/0105075 A1 | 5/2006 | Otsubo |
| 2006/0189954 A1 | 8/2006 | Kudo |
| 2006/0270302 A1 | 11/2006 | Ando |
| 2006/0286343 A1 | 12/2006 | Curro |
| 2007/0026753 A1 | 2/2007 | Neely |
| 2007/0045143 A1 | 3/2007 | Clough |
| 2007/0045144 A1 | 3/2007 | Wheeler |
| 2007/0131335 A1 | 6/2007 | Zhou |
| 2007/0141311 A1 | 6/2007 | Mleziva |
| 2007/0167929 A1 | 7/2007 | Fossum et al. |
| 2007/0179466 A1 | 8/2007 | Tremblay |
| 2007/0298214 A1 | 12/2007 | Noda et al. |
| 2007/0298667 A1 | 12/2007 | Noda et al. |
| 2008/0045915 A1 | 2/2008 | Noda et al. |
| 2008/0149292 A1 | 6/2008 | Scherb |
| 2008/0161768 A1 | 7/2008 | Baba |
| 2008/0287897 A1 | 11/2008 | Guzman |
| 2009/0240222 A1 | 9/2009 | Tomoko et al. |
| 2009/0312730 A1 | 12/2009 | Lavon |
| 2010/0022151 A1 | 1/2010 | Malowaniec |
| 2010/0036346 A1 | 2/2010 | Hammons |
| 2010/0048072 A1 | 2/2010 | Kauschke |
| 2010/0075103 A1 | 3/2010 | Miyamoto |
| 2010/0076394 A1 | 3/2010 | Hayase |
| 2010/0248575 A1 | 9/2010 | Malz |
| 2010/0307668 A1 | 12/2010 | Lange |
| 2011/0118689 A1 | 5/2011 | Een |
| 2011/0144605 A1 | 6/2011 | Noda |
| 2011/0250378 A1 | 10/2011 | Eaton |
| 2012/0004633 A1 | 1/2012 | R. Marcelo |
| 2012/0061015 A1 | 3/2012 | Lavon |
| 2012/0061016 A1 | 3/2012 | Lavon |
| 2012/0095429 A1 | 4/2012 | Kobayashi |
| 2012/0196091 A1 | 8/2012 | Mizutani et al. |
| 2012/0296303 A1 | 11/2012 | Ng et al. |
| 2013/0032656 A1 | 2/2013 | Yamamoto |
| 2013/0072887 A1 | 3/2013 | Lavon |
| 2013/0112584 A1 | 5/2013 | Gaspari |
| 2013/0139960 A1 | 6/2013 | Maruyama |
| 2013/0171421 A1 | 7/2013 | Weisman |
| 2013/0199696 A1 | 8/2013 | Schneider |
| 2013/0199707 A1 | 8/2013 | Schneider |
| 2013/0211356 A1 | 8/2013 | Nishikawa |
| 2013/0255861 A1 | 10/2013 | Schneider |
| 2013/0255862 A1 | 10/2013 | Schneider |
| 2013/0255863 A1 | 10/2013 | Lavon |
| 2013/0255864 A1 | 10/2013 | Schneider |

(56) References Cited

U.S. PATENT DOCUMENTS

| | | |
|---|---|---|
| 2013/0255865 A1 | 10/2013 | Brown |
| 2013/0261589 A1 | 10/2013 | Fujkawa |
| 2013/0306226 A1 | 11/2013 | Zink |
| 2013/0320584 A1 | 12/2013 | Davis et al. |
| 2014/0000794 A1 | 1/2014 | Hamilton |
| 2014/0018759 A1 | 1/2014 | Jayasinghe |
| 2014/0041797 A1 | 2/2014 | Schneider |
| 2014/0045401 A1 | 2/2014 | Kunihiro et al. |
| 2014/0127460 A1 | 5/2014 | Xu |
| 2014/0148773 A1 | 5/2014 | Brown |
| 2014/0234575 A1 | 8/2014 | Mitsuno |
| 2014/0235127 A1 | 8/2014 | Dejesus |
| 2014/0257231 A1 | 9/2014 | Wang |
| 2014/0276517 A1 | 9/2014 | Chester |
| 2014/0296815 A1 | 10/2014 | Takken |
| 2014/0305570 A1 | 10/2014 | Matsunaga |
| 2014/0324009 A1 | 10/2014 | Lee |
| 2014/0343525 A1 | 11/2014 | Roh et al. |
| 2014/0377506 A1 | 12/2014 | Eckstein |
| 2014/0377513 A1 | 12/2014 | Galie |
| 2015/0083309 A1 | 3/2015 | Long |
| 2015/0173967 A1 | 6/2015 | Kreuzer |
| 2015/0230995 A1 | 8/2015 | Kaneko |
| 2015/0282999 A1 | 10/2015 | Arizti |
| 2015/0320613 A1 | 11/2015 | Seitz |
| 2015/0320619 A1 | 11/2015 | Seitz |
| 2015/0328056 A1 | 11/2015 | Een |
| 2015/0351972 A1 | 12/2015 | Bing-wo |
| 2016/0058624 A1 | 3/2016 | Hohm |
| 2016/0058627 A1 | 3/2016 | Barnes |
| 2016/0067119 A1 | 3/2016 | Weisman |
| 2016/0074256 A1 | 3/2016 | Strube et al. |
| 2016/0100989 A1 | 4/2016 | Seitz |
| 2016/0100997 A1 | 4/2016 | Seitz |
| 2016/0106633 A1 | 4/2016 | Nagata |
| 2016/0129661 A1 | 5/2016 | Arora |
| 2016/0136009 A1 | 5/2016 | Weisman |
| 2016/0228305 A1 | 8/2016 | Gualtieri |
| 2016/0331600 A1 | 11/2016 | Polidori |
| 2016/0355950 A1 | 12/2016 | Young et al. |
| 2017/0000695 A1 | 1/2017 | Castillo et al. |
| 2017/0002486 A1 | 1/2017 | Castillo et al. |
| 2017/0014281 A1 | 1/2017 | Xie |
| 2017/0014291 A1 | 1/2017 | Tao et al. |
| 2017/0027774 A1 | 2/2017 | Ashraf |
| 2017/0029993 A1 | 2/2017 | Ashraf |
| 2017/0029994 A1 | 2/2017 | Ashraf |
| 2017/0056256 A1 | 3/2017 | Smith |
| 2017/0065461 A1 | 3/2017 | Schneider |
| 2017/0079852 A1 | 3/2017 | Fujima |
| 2017/0119595 A1 | 5/2017 | Carla |
| 2017/0121873 A1 | 5/2017 | Kimura et al. |
| 2017/0191198 A1 | 7/2017 | Ashraf |
| 2017/0258650 A1 | 9/2017 | Rosati |
| 2017/0258651 A1 | 9/2017 | Hammons |
| 2017/0319403 A1 | 11/2017 | Bewick-sonntag |
| 2017/0342617 A1 | 11/2017 | Castillo |
| 2017/0348163 A1 | 12/2017 | Lakso |
| 2018/0002848 A1 | 1/2018 | Burt et al. |
| 2018/0092784 A1 | 4/2018 | Wade |
| 2018/0140473 A1 | 5/2018 | Koshijima |
| 2018/0168874 A1 | 6/2018 | Lavon |
| 2018/0168875 A1 | 6/2018 | Lavon |
| 2018/0168876 A1 | 6/2018 | Lavon |
| 2018/0168877 A1 | 6/2018 | Schneider |
| 2018/0168878 A1 | 6/2018 | Schneider |
| 2018/0168879 A1 | 6/2018 | Schneider |
| 2018/0168880 A1 | 6/2018 | Schneider |
| 2018/0168885 A1 | 6/2018 | Zink, II |
| 2018/0168887 A1 | 6/2018 | Lavon |
| 2018/0168889 A1 | 6/2018 | Lavon |
| 2018/0168890 A1 | 6/2018 | Lavon |
| 2018/0168891 A1 | 6/2018 | Wise |
| 2018/0168892 A1 | 6/2018 | Lavon |
| 2018/0168893 A1 | 6/2018 | Ashraf |
| 2018/0169964 A1 | 6/2018 | Schneider |
| 2018/0170026 A1 | 6/2018 | Schneider |
| 2018/0170027 A1 | 6/2018 | Schneider |
| 2018/0214318 A1 | 8/2018 | Ashraf |
| 2018/0214321 A1 | 8/2018 | Ashraf |
| 2018/0216269 A1 | 8/2018 | Ashraf |
| 2018/0216270 A1 | 8/2018 | Ashraf |
| 2018/0216271 A1 | 8/2018 | Ashraf |
| 2019/0003079 A1 | 1/2019 | Ashraf |
| 2019/0003080 A1 | 1/2019 | Ashraf |
| 2019/0070041 A1 | 3/2019 | Schneider |
| 2019/0070042 A1 | 3/2019 | Beck |
| 2019/0112737 A1 | 4/2019 | Ashraf |
| 2019/0246196 A1 | 8/2019 | Han |
| 2019/0298586 A1 | 10/2019 | Ashraf |
| 2019/0298587 A1 | 10/2019 | Ashraf |
| 2019/0374392 A1 | 12/2019 | Ninomiya |
| 2019/0374404 A1 | 12/2019 | Ninomiya |
| 2019/0380887 A1 | 12/2019 | Ashraf et al. |
| 2020/0054501 A1 | 2/2020 | Seto et al. |
| 2020/0155370 A1 | 5/2020 | Ohtsubo |
| 2020/0155371 A1 | 5/2020 | Ohtsubo |
| 2020/0206040 A1 | 7/2020 | Andrews |
| 2020/0214901 A1 | 7/2020 | Andrews |
| 2020/0298545 A1 | 9/2020 | Andrews |
| 2020/0360198 A1 | 11/2020 | Ashraf et al. |
| 2020/0397629 A1 | 12/2020 | Aviles et al. |
| 2020/0397630 A1 | 12/2020 | Arora et al. |

FOREIGN PATENT DOCUMENTS

| | | |
|---|---|---|
| CN | 1276196 A | 12/2000 |
| CN | 1342446 A | 4/2002 |
| CN | 1348514 A | 5/2002 |
| CN | 1685009 A | 10/2005 |
| CN | 1685099 A | 10/2005 |
| CN | 1731965 A | 2/2006 |
| CN | 1778702 A | 5/2006 |
| CN | 1934306 A | 3/2007 |
| CN | 101410078 A | 4/2009 |
| CN | 101746057 A | 6/2010 |
| CN | 102448418 A | 5/2012 |
| CN | 103502004 A | 1/2014 |
| CN | 104507436 A | 4/2015 |
| CN | 105073079 A | 11/2015 |
| CN | 204931997 U | 1/2016 |
| CN | 105395319 A | 3/2016 |
| CN | 105997351 A | 10/2016 |
| CN | 107809987 A | 3/2018 |
| CN | 108348372 A | 7/2018 |
| EP | 0973470 A1 | 1/2000 |
| EP | 0989218 A1 | 3/2000 |
| EP | 1305248 A2 | 5/2003 |
| EP | 1452157 A1 | 9/2004 |
| EP | 1473148 A1 | 11/2004 |
| EP | 1393701 B1 | 7/2013 |
| EP | 2660377 B1 | 4/2014 |
| EP | 3056176 A1 | 8/2016 |
| EP | 3092997 B1 | 8/2017 |
| EP | 3251642 A1 | 12/2017 |
| EP | 3257488 A1 | 12/2017 |
| EP | 3563817 A1 | 11/2019 |
| JP | H03213543 A | 9/1991 |
| JP | H0430847 A | 2/1992 |
| JP | H06254117 A | 9/1994 |
| JP | H0871107 A | 3/1996 |
| JP | H08132576 A | 5/1996 |
| JP | H1176298 A | 3/1999 |
| JP | 2000026015 A | 1/2000 |
| JP | 2002035029 A | 2/2002 |
| JP | 2002178428 A | 6/2002 |
| JP | 2002238934 A | 8/2002 |
| JP | 2002248127 A | 9/2002 |
| JP | 2003103740 A | 4/2003 |
| JP | 2004229857 A | 8/2004 |
| JP | 2004237410 A | 8/2004 |
| JP | 2004254862 A | 9/2004 |
| JP | 2004298362 A | 10/2004 |
| JP | 2005320636 A | 11/2005 |

(56) References Cited

FOREIGN PATENT DOCUMENTS

| | | |
|---|---|---|
| JP | 2006149747 A | 6/2006 |
| JP | 2006149749 A | 6/2006 |
| JP | 2006204673 A | 8/2006 |
| JP | 2007190397 A | 8/2007 |
| JP | 2008029749 A | 2/2008 |
| JP | 2008055198 A | 3/2008 |
| JP | 2008105425 A | 5/2008 |
| JP | 2008148942 A | 7/2008 |
| JP | 2008179128 A | 8/2008 |
| JP | 2008194493 A | 8/2008 |
| JP | 2008229006 A | 10/2008 |
| JP | 2008229007 A | 10/2008 |
| JP | 2008253290 A | 10/2008 |
| JP | 2008260131 A | 10/2008 |
| JP | 2008264480 A | 11/2008 |
| JP | 2008272250 A | 11/2008 |
| JP | 2008272253 A | 11/2008 |
| JP | 2008296585 A | 12/2008 |
| JP | 2009000161 A | 1/2009 |
| JP | 2009000173 A | 1/2009 |
| JP | 2009039341 A | 2/2009 |
| JP | 2009056156 A | 3/2009 |
| JP | 2009172231 A | 8/2009 |
| JP | 2009240804 A | 10/2009 |
| JP | 2009241607 A | 10/2009 |
| JP | 2010005918 A | 1/2010 |
| JP | 2010131833 A | 6/2010 |
| JP | 2011015707 A | 1/2011 |
| JP | 2011178124 A | 9/2011 |
| JP | 2011225000 A | 11/2011 |
| JP | 2012050882 A | 3/2012 |
| JP | 2012050883 A | 3/2012 |
| JP | 2012105908 A | 6/2012 |
| JP | 2012115358 A | 6/2012 |
| JP | 5124187 B2 | 11/2012 |
| JP | 5124188 B2 | 11/2012 |
| JP | 2013138795 A | 7/2013 |
| JP | 2014097257 A | 5/2014 |
| JP | 2014188042 A | 10/2014 |
| JP | 2015171501 A | 10/2015 |
| JP | 2016013687 A | 1/2016 |
| JP | 2016016536 A | 2/2016 |
| JP | 5942819 B2 | 6/2016 |
| JP | 2016112217 A | 6/2016 |
| JP | 2016193199 A | 11/2016 |
| JP | 6149635 B2 | 6/2017 |
| JP | 2017528612 A | 9/2017 |
| JP | 2017222970 A | 12/2017 |
| JP | 2018102641 A | 7/2018 |
| JP | 2019024947 A | 2/2019 |
| JP | 2019083863 A | 6/2019 |
| JP | 2020054741 A | 4/2020 |
| JP | 2020054742 A | 4/2020 |
| JP | 2020054744 A | 4/2020 |
| JP | 2020054745 A | 4/2020 |
| JP | 2022117131 A | 8/2022 |
| RU | 2424256 C2 | 7/2011 |
| WO | 03015681 A1 | 2/2003 |
| WO | 2006057369 A1 | 6/2006 |
| WO | 2008123348 A1 | 10/2008 |
| WO | 2011137962 A1 | 11/2011 |
| WO | 2012086730 A1 | 6/2012 |
| WO | 2013018846 A1 | 2/2013 |
| WO | 2013084977 A1 | 6/2013 |
| WO | 2013091150 A1 | 6/2013 |
| WO | 2013099625 A1 | 7/2013 |
| WO | 2013145966 A1 | 10/2013 |
| WO | 2014084168 A1 | 6/2014 |
| WO | 2014196669 A2 | 12/2014 |
| WO | 2015002331 A2 | 1/2015 |
| WO | 2016056092 A1 | 4/2016 |
| WO | 2016056093 A1 | 4/2016 |
| WO | 2016063346 A1 | 4/2016 |
| WO | 2016067387 A1 | 5/2016 |
| WO | 2016071981 A1 | 5/2016 |
| WO | 2016075974 A1 | 5/2016 |
| WO | 2016098416 A1 | 6/2016 |
| WO | 2016104412 A1 | 6/2016 |
| WO | 2016104422 A1 | 6/2016 |
| WO | 2016158499 A1 | 10/2016 |
| WO | 2016158746 A1 | 10/2016 |
| WO | 2016208502 A1 | 12/2016 |
| WO | 2016208513 A1 | 12/2016 |
| WO | 2017004309 A1 | 1/2017 |
| WO | 2017105997 A1 | 6/2017 |
| WO | 2017110695 A1 | 6/2017 |
| WO | 2018064595 A1 | 4/2018 |
| WO | 2018154680 A1 | 8/2018 |
| WO | 2018154682 A1 | 8/2018 |
| WO | 2018167836 A1 | 9/2018 |
| WO | 2019150802 A1 | 8/2019 |
| WO | 2019246194 A1 | 12/2019 |
| WO | 2019246196 A1 | 12/2019 |

OTHER PUBLICATIONS

All Office Actions; U.S. Appl. No. 18/487,172, filed Oct. 16, 2023.
Unpublished U.S. Appl. No. 18/487,172, filed Oct. 16, 2023, to Kelyn Anne Arora et. al.
All Office Actions; U.S. Appl. No. 118/616,791, filed Mar. 26, 2024.
Unpublished U.S. Appl. No. 18/616,791, filed Mar. 26, 2024, to Arman Ashraf et. al.
All Office Actions; U.S. Appl. No. 18/331,240, filed Jun. 8, 2023.
Unpublished U.S. Appl. No. 18/331,240, filed Jun. 8, 2023, to Arman Ashraf et. al.
PCT Search Report and Written Opinion for PCT/US2019/036265 dated Oct. 2, 2019, 13 pages.
Extended EP Search Report and Written Opinion for 22176315.4 dated Sep. 27, 2022, 9 pages.
3D Nonwovens Developments for textured nonwovens; Sep. 19, 2017, pp. 1-2.
All Office Actions for U.S. Appl. No. 16/983,140, filed Aug. 3, 2020.
All Office Actions, U.S. Appl. No. 16/445,986, filed Jun. 19, 2019.
All Office Actions, U.S. Appl. No. 16/446,052, filed Jun. 19, 2019.
All Office Actions, U.S. Appl. No. 16/446,118, filed Jun. 19, 2019.
All Office Actions, U.S. Appl. No. 16/446,156, filed Jun. 19, 2019.
All Office Actions, U.S. Appl. No. 16/445,838, filed Jun. 19, 2019.

\* cited by examiner

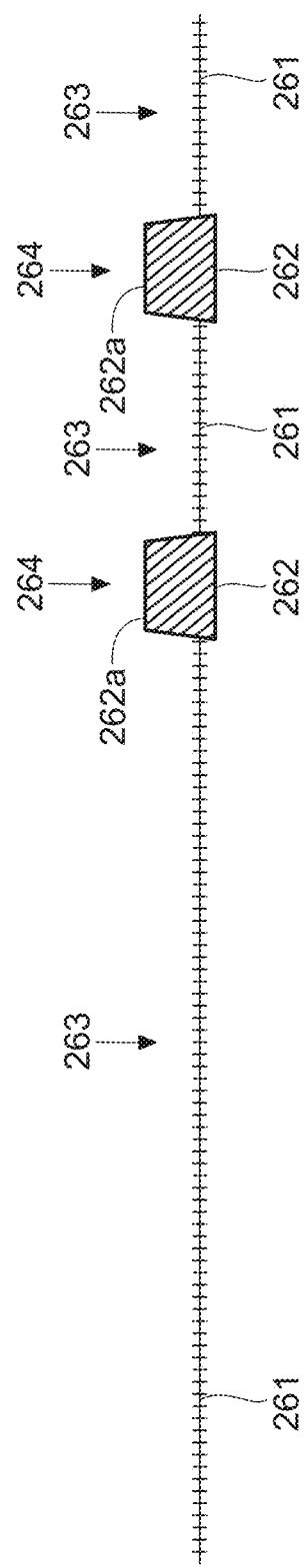

STRETCH LAMINATE WITH BEAMED ELASTICS AND FORMED NONWOVEN LAYER

CROSS REFERENCE TO RELATED APPLICATIONS

This application is a continuation of, and claims priority under 35 U.S.C. § 120 to, U.S. patent application Ser. No. 16/445,838, filed on Jun. 19, 2019 which claims the benefit of U.S. Provisional Application No. 62/687,031, filed on Jun. 19, 2018, the entire disclosures of which are incorporated herein by reference.

This application is a continuation-in-part of application Ser. No.:
  15/831,448, filed on Dec. 5, 2017, now U.S. Pat. No. 10,973,699, granted Apr. 13, 2021;
  Ser. No. 15/831,464, filed on Dec. 5, 2017;
  Ser. No. 15/832,929, filed on Dec. 6, 2017, now U.S. Pat. No. 11,141,321, granted Oct. 12, 2021;
  Ser. No. 15/833,057, filed on Dec. 6, 2017, now U.S. Pat. No. 11,147,717, granted Oct. 19, 2021;
  Ser. No. 15/838,405, filed on Dec. 12, 2017, now U.S. Pat. No. 11,219,555, granted Jan. 11, 2022;
  Ser. No. 15/846,349, filed on Dec. 19, 2017, now U.S. Pat. No. 11,000,426, granted May 11,2021;
  Ser. No. 15/846,745, filed on Dec. 19, 2017.
the entire disclosures of which are incorporated herein by reference.

FIELD OF THE INVENTION

The present disclose relates to stretch laminates formed of nonwoven web material components, and wearable articles in which such stretch laminates may form components.

BACKGROUND OF THE INVENTION

Wearable absorbent articles such as disposable absorbent pants and disposable diapers sometimes include elasticized laminates or "stretch laminates" having one or more layers of nonwoven web material, joined with an elastic material. The elastic material may take a variety of forms, including an elastic film, a plurality of elastic strips, elastic scrim, a plurality of spaced elastic strands, or a combination of these.

By way of non-limiting example, a number of currently marketed disposable absorbent pants for children and adults include a belt structure that surrounds the wearer's lower torso, wherein the belt structure is formed of a stretch laminate that is elastically stretchable along a lateral direction. This type of pants structure is favored for attributes relating to fit and wearer comfort, and manufacturing efficiency. The typical belt structure has an outward-facing layer formed of a first nonwoven web material, a wearer-facing layer formed of a second nonwoven web material, and an elastic material sandwiched between the outward-facing layer and the wearer-facing layer. The elastic material is, typically, a film made of elastomeric polymer, or a plurality of longitudinally-spaced, laterally-oriented strands made of elastomeric polymer. In many examples the elastic material is pre-strained along a stretch direction during the manufacturing process, and sandwiched and affixed between the layers while in the pre-strained condition. Following completion of manufacture, the elastic material contracts toward its relaxed dimension(s), causing the sandwiching layers to gather along the stretch direction. The gathers in the sandwiching layers serve to accommodate stretch of the laminate when the article is donned and worn, while the elasticity of the elastic material provides lateral tensile contraction force, providing for a snug, comfortable and conforming fit about the wearer's lower torso.

Because elastomeric polymer materials are relatively expensive, stretch laminates in which the sandwiched elastic material is elastic film tend to be more expensive and less cost-competitive than stretch laminates in which the elastic material is a plurality of elastic strands. Additionally, elastic film is membrane-like, and renders the laminate relatively less breathable than may be desired for purposes of skin comfort. Alternatively, when the elastic material is in the form of a plurality of longitudinally-spaced, laterally-oriented elastic strands, the laminate can be made less expensively and more cost-competitively, and have relatively greater breathability. One feature of this latter type of laminate, however, is that its structure results in formation of gathers or ruffles of sandwiching material that can be relatively large, imparting to the material a bulky, mottled, ruffled appearance that in some circumstances may be deemed undesirable and/or uncomfortable. Aside from the appearance of the stretch laminate material in and of itself, the relatively large ruffles make inclusion of decorative elements on the laminate problematic, because decorative elements (typically, one or more design elements printed on a surface of one of the sandwiching layers) tend to become folded up within the gathers, substantially reducing or otherwise negatively affecting their recognizability and visual impact.

Recently it has been discovered that use of "beamed" elastics is feasible for use in making stretch laminates of the type contemplated herein, and may provide a number of benefits that include substantial mitigation of the above-mentioned disadvantages of use of film elastic layers and conventional elastic strands, respectively, together with realization of advantages associated, respectively with use of each type of material.

Manufacturers of these types of products continuously strive to improve the functionality and appearance of the products, in ways that are pleasing to consumers while being cost-competitive. Accordingly, any cost-effective improvements to stretch laminates that serve to enhance appearance and/or functionality will provide the manufacturer thereof competitive advantages in the market.

BRIEF DESCRIPTION OF THE DRAWINGS

FIG. 8A is a schematic cross-section view of the portion of the forming belt shown in FIG. 7, taken along line 8-8 in FIG. 7.

DESCRIPTION OF EXAMPLES

Definitions

Figure 1A:
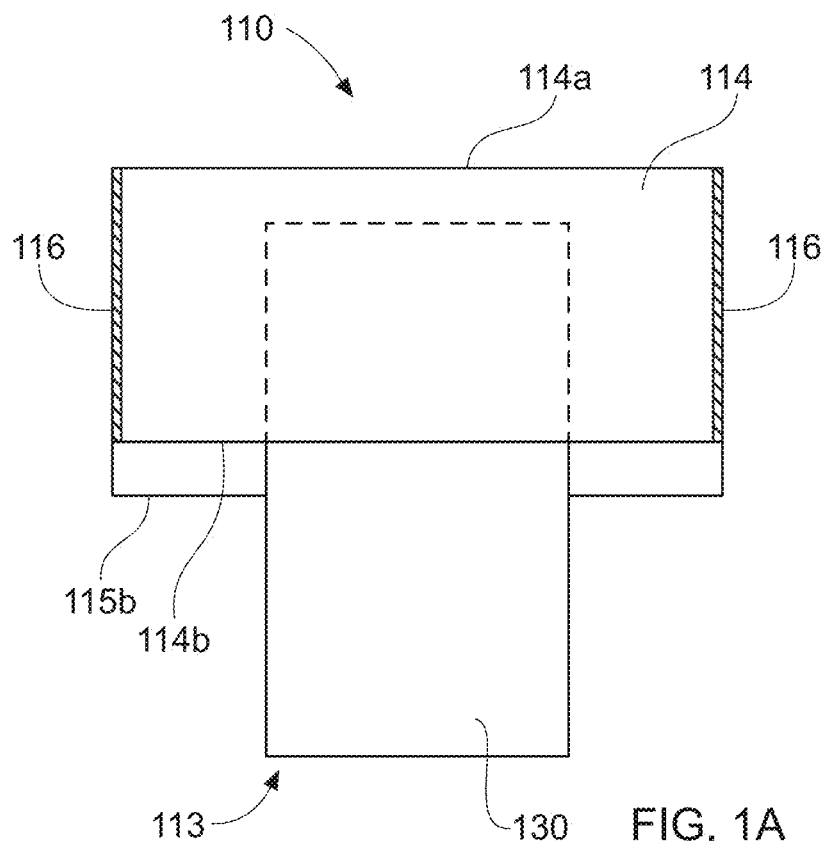
FIG. 1A is a schematic front view of a wearable disposable absorbent article in the form of a pant.

With respect to a nonwoven web material formed partially or entirely of fibers and/or filaments, a "bond" is a three-dimensional volume or shape within the material in which a plurality of the fibers and/or filaments are held together in a unitary mass created by one or a combination of a deposit of adhesive applied to the material, thermal fusing caused by localized application of heating energy to the material (for example, heat from defined bonding protrusions on a heated bonding roller, or ultrasonic vibratory energy from a sonotrode in combination with a bonding roller with defined bonding protrusions), or plastic deformation and entanglement or intermeshing caused by localized application of pressure (for example, by a bonding roller with defined bonding protrusions) to the material in the z-direction. A bond has a two-dimensional profile along the x-y plane approximated by the large surfaces of the web material, as well as a z-direction dimension. When bonds are created via use of a bonding roller with defined bonding protrusions, the two-dimensional profiles of the bonds will approximately reflect the shape(s) of the bonding protrusions.

"Fiber" as used herein means an elongate particulate having a length less than 5.08 cm (2 in.). In the field of nonwoven web manufacturing, fibers are typically considered discontinuous in nature. Non-limiting examples of fibers include natural fibers such as wood pulp, cotton and bamboo fibers, and synthetic staple fibers (which may be manufactured by chopping filaments) such as polypropylene, polyethylene, polyester, copolymers thereof, rayon, lyocell, glass fibers and polyvinyl alcohol fibers.

"Filament" as used herein means an elongate particulate having a length equal to or greater than or equal to 5.08 cm (2 in.). In the field of nonwoven web manufacturing, filaments are typically considered to be of indefinite length and/or be substantially continuous in nature with respect to nonwoven web materials in which they appear, in contrast to fibers, it being recognized that they cannot be of infinite length. Non-limiting examples of filaments include meltblown and/or spunbond filaments. Non-limiting examples of polymers that may be spun into filaments include natural polymers, such as starch, starch derivatives, cellulose, such as rayon and/or lyocell, and cellulose derivatives, hemicellulose, hemicellulose derivatives, and synthetic polymers including, but not limited to polyvinyl alcohol filaments and/or polyvinyl alcohol derivative filaments, and thermoplastic polymers such as polyesters, nylons, polyolefins such as polypropylene, polyethylene, and biodegradable or compostable thermoplastics such as polylactic acid, polyhydroxyalkanoate, polyesteramide, and polycaprolactone. Spun filaments may be monocomponent or multicomponent, for example, bicomponent.

The "region basis weight" of a region of a section of nonwoven web material means the weight in grams of the region of interest, divided by its surface area on one side, measured by any appropriate measurement technique including but not necessarily limited to the Localized Basis Weight measurement method described herein.

"Intensive properties" of a region of a nonwoven web material include basis weight; aggregate total of the lengths of all fibers and/or filaments present per unit surface area of the material lying along an x-y plane (referred to herein as fiber and/or filament "area density"); caliper/thickness in the z-direction; and density (mass per unit volume).

"Lateral," with respect to a pant, refers to the direction perpendicular to the longitudinal direction, and from side-to-side of the article from the wearer's perspective.

"Longitudinal," with respect to a pant, refers to the direction from front-to-rear or from rear-to-front of the article from the wearer's perspective.

"Nonwoven," means a cloth-like fabric or web material formed predominately of fibers, filaments or a combination thereof, which are not knitted or woven, but rather are laid down and accumulated into a batt and then consolidated and held together in a coherent fabric web of material by entangling, by a dispersed binding agent, by a pattern of discrete bonds formed by localized deposits of adhesive, or by a pattern of localized bonds (localized thermal fusing, localized plastic deformation and/or entanglement between fibers or filaments caused by localized applications of pressure), or a combination thereof.

"Ordered arrangement," with respect to a section of nonwoven web material having a regular (repeating) pattern or configuration of zones that each include adjacent regions of differing intensive properties, or an irregular (non-repeating) pattern or configuration of zones that each include adjacent regions of differing intensive properties, along a surface of the material, means an arrangement of such zones that is recognizable by a person of ordinary skill in the art of nonwoven web manufacturing as an ordered, non-random arrangement or pattern, as contrasted with a random, unordered accumulation and distribution of filaments and/or fibers. As will be recognized by persons of ordinary skill in the art relevant to this disclosure, an ordered arrangement of such zones will result from process steps and equipment used to manufacture the nonwoven web material, configured to repeatably effect the ordered arrangement in the nonwoven web material. An ordered arrangement of zones in a nonwoven web material may reflect an ordered arrangement of features of forming equipment, such as an ordered arrangement of features on a forming belt.

"Visually discernible" means visible and visually detectable from a distance of approximately 0.5 meter or more, to the naked eye of an ordinary observer having 20/20 vision, under indoor office lighting conditions deemed appropriate for reading printed text media.

A "zone" is a portion of an area of a nonwoven web material comprising at least first and second adjacent regions thereof, the first and second adjacent regions having differences in one or a combination of basis weight, caliper, density (mass/volume), and/or fiber and/or filament area density.

"z-direction," with respect to a web material or portion thereof laid out along an x-y plane, means the direction orthogonal to the x-y plane. "z-direction," with respect to a forming belt used to manufacture a nonwoven web material moving through a working location of belt travel lying along an x-y plane, means the direction orthogonal to the x-y plane.

"Wearer-facing" and "outward-facing" refer respectively to the relative location of an element or a surface of an element or group of elements. "Wearer-facing" implies the element or surface is nearer to the wearer during wear than some other element or surface. "Outward-facing" implies the element or surface is more remote from the wearer during wear than some other element or surface (i.e., element or surface is proximate to the wearer's garments that may be worn over the disposable absorbent article).

"Joined" encompasses configurations whereby an element is directly secured to another element by affixing the element directly to the other element, and configurations whereby an element is indirectly secured to another element by affixing the element to intermediate member(s), which, in turn are affixed to the other element.

"Liquid-permeable" and "liquid-impermeable" refer to the penetrability of materials in the context of the intended usage of disposable absorbent articles. Specifically, the term "liquid-permeable" refers to a layer or a layered structure having pores, openings, and/or interconnected void spaces that permit aqueous liquid such as water, urine, or synthetic urine to pass through its thickness in the absence of a forcing pressure. Conversely, the term "liquid-impermeable" refers to a layer or a layered structure through the thickness of which aqueous liquid such as water, urine, or synthetic urine cannot pass in the absence of a forcing pressure (aside from natural forces such as gravity). A layer or a layered structure that is liquid-impermeable according to this definition may be permeable to liquid vapor, i.e., may be "vapor-permeable."

"Elastic," "elastomer," or "elastomeric" refers to a material or combination of materials exhibiting elastic properties, by which, upon application of a tensile force to its relaxed, initial length, the material or combination of materials can stretch or elongate to an elongated length more than 10% greater than its initial length, and following such elongation and upon release of the applied tensile force, will contract back toward its initial length by at least 50% of the elongation. Elastomeric materials may include elastomeric films, scrims, nonwovens, ribbons, strands, and other sheet-like structures, and stretch laminates.

"Pre-strain" refers to the strain imposed on an elastic or elastomeric material prior to combining it with another element of an elastic laminate or the absorbent article. Pre-strain is determined by the following equation:

$$\text{Pre-strain} = 100\% \times [(\text{extended length of the material}) - (\text{relaxed length of the material})]/(\text{relaxed length of the material})$$

"Decitex" also known as "dtex" is a unit used in the textile industry used to express linear mass density of fibers and yarns. 1 decitex=1 gram per 10,000 meters. For example, if 10,000 linear meters of a yarn or filament weighs 500 grams, it is 500 decitex.

"Machine direction" (MD) is used herein to refer to the direction of material movement through equipment used to effect a process. In addition, relative placement and movement of material can be described as moving in the machine direction through the equipment from upstream in the process to downstream in the process. With respect to incorporation of pre-strained elastic material into a stretch laminate during manufacture thereof, the direction of pre-strain, and the resulting stretch direction of the stretch laminate product, in most instances will be substantially aligned with the machine direction.

"Cross direction" (CD) is used herein to refer to a direction that is generally perpendicular to the machine direction.

"Pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be pre-formed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be pre-formed anywhere along the circumference of the article in the waist region (e.g., side fastened or seamed, front waist fastened or seamed, rear waist fastened or seamed). Example diaper pants in various configurations are disclosed in U.S. Pat. Nos. 4,940,464; 5,092,861; 5,246,433; 5,569,234; 5,897,545; 5,957,908; 6,120,487; 6,120,489; 7,569,039 and U.S. Patent Publication Nos. 2003/0233082 A1; 2005/0107764 A1, 2012/0061016 A1, 2012/0061015 A1; 2013/0255861 A1; 2013/0255862 A1; 2013/0255863 A1; 2013/0255864 A1; and 2013/0255865 A1, all of which are incorporated by reference herein.

Herein, an "elastic strand" or "strand" refers to a yarn-like bundle of a plurality of individual filaments each spun or extruded of elastomeric material, combined together into an effectively unitary structure. The filaments may or may not be twisted about each other, as in the fiber or filament constituents of a twisted multi-fiber and/or multi-filament yarn. The low-decitex elastic strands contemplated for use herein as beamed elastic strands may have no more than 30 filaments, no more than 20 filaments, no more than 15 filaments or even no more than 10 filaments per strand.

"Average-Pre-Strain" of a plurality of elastic strands within a stretch laminate is determined according to the Average-Pre-Strain measurement method set forth herein.

"Average Decitex" or "Average Dtex" of a plurality of elastic strands within a stretch laminate is determined according to the Average Decitex measurement method set forth herein.

"Average-Strand-Spacing" of a plurality of elastic strands within a stretch laminate is determined according to the Average-Strand-Spacing measurement method set forth herein.

"Manufacturing Pre-Strain" means the average amount, specified by the manufacturer of an article or stretch laminate component thereof, by which a plurality of elastic strands of an elasticized band are elongated together as they are unwound from a single warp beam, spool or other storage device from their relaxed length, as they are first joined to one or more web materials in a process to form a stretch laminate. Manufacturing Pre-Strain may be specified directly, or it may be specified indirectly, e.g., by tensile force under which the strands are placed as they are joined with the web material. Where not specified directly, Manufacturing Pre-Strain may be calculated and/or determined based upon, e.g., the Manufacturing Decitex, material modulus, number of strands, and applied tensile force specified by the manufacturer for manufacturing the laminate.

"Manufacturing Decitex" or "Manufacturing Dtex" means the average decitex of a plurality of elastic strands, specified by the manufacturer of an article or stretch laminate component thereof, that are supplied on and unwound from a single warp beam, spool or other storage device and joined to one or more web materials to form the stretch laminate.

"Manufacturing Strand Spacing" means the average center-to-center spacing among a plurality of elastic strands, specified by the manufacturer of an article or stretch laminate component thereof, that are unwound from a single warp beam, spool or other storage device and joined to one or more web materials to form the stretch laminate, at the time they are first joined to the one or more materials.

Wearable Articles

Wearable articles contemplated herein include any wearable article that includes a portion or section of a stretch laminate. A stretch laminate is a combination of an elastic/elastomeric material in strip, strand or film/sheet form, laminated with one or more relatively less elastic or relatively non-elastic layers of web material, such as a nonwoven web material. A typical stretch laminate may include two layers relatively non-elastic nonwoven web material, with an elastic material sandwiched and laminated therebetween. In some examples, the stretch laminate is manufactured in a process in which the elastic material is strained in a machine/stretch direction during lamination with the other layers. Upon completion of manufacture, elastic contraction of the elastic material causes the other layers to gather into ruffles along the machine/stretch direction. The laminate with the gathered material is useful for forming a variety of components of wearable articles in which elastic stretch and contraction may be desirable, for purposes such as ease of donning, gasketing, secure and conforming fit and wearer comfort.

Figure 1B:
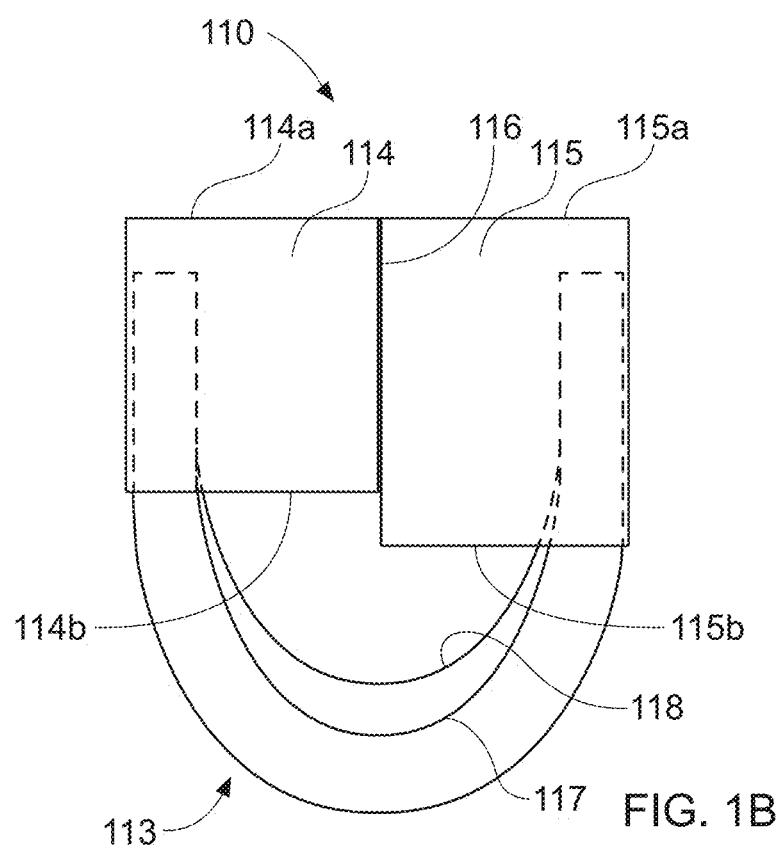
FIG. 1B is a schematic side view of a wearable disposable absorbent article in the form of a pant.

FIGS. 1A and 1B schematically depict front and side views of a wearable absorbent article in the form of a disposable absorbent pant 110 of the belt- or balloon-type. Such a pant may be formed of a waist-surrounding belt structure and a central chassis 113. The belt structure may have a front belt portion 114 and a rear belt portion 115. A front portion of chassis 113 may be joined to the inside (wearer-facing side) of front belt portion 114, and a rear portion of chassis 113 may be joined to the inside (wearer-facing side) of rear belt portion 115, and a crotch portion of chassis 113 may bridge the front and rear belt portions. Central chassis 113 may include components typical for articles such as disposable diapers and disposable absorbent pants, such as a wearer-facing, liquid permeable topsheet (not shown), an outward-facing, liquid impermeable backsheet 130, an absorbent structure (not shown) disposed between the topsheet and backsheet, a pair of elasticized outer leg cuffs 117, and a pair of elasticized inner barrier cuffs 118. One or both of front belt portion 114 and rear belt portion 115 may be formed of stretch laminate material, manufactured so as to be elastically stretchable and contractible at least along a lateral stretch direction. Front belt portion 114 and rear belt portion 115 may be joined to each other at two side/hip seams 116, thereby forming the waist-surrounding belt structure. When the pant is assembled in this manner, the front belt portion may form a front waist opening edge 114a and in part, front leg opening edges 114b, and the rear belt portion may form a rear waist opening edge 115a and in part, rear leg opening edges 115b, of the pant. As suggested in FIGS. 1A and 1B, in some non-limiting examples, the rear belt portion 115 may have a greater longitudinal dimension than the front belt portion 114, for purposes of greater coverage of the wearer's buttocks area. In some examples the lower rear corners of a longer rear belt portion 115 may be trimmed away to impart a more tailored appearance to the leg opening edges; in other examples the lower corners of a longer rear belt portion, being unattached to the front belt portion at the side seams 116, may be effectively pulled laterally inward by contraction of elastic materials in the rear belt portion, serving the same purpose.

The stretch laminate described herein may be used to form one or both of front and rear belt portions 114 and 115 of such a pant, as well as any other components for wearable articles as may find application or be desirable therefor.

Figure 2:
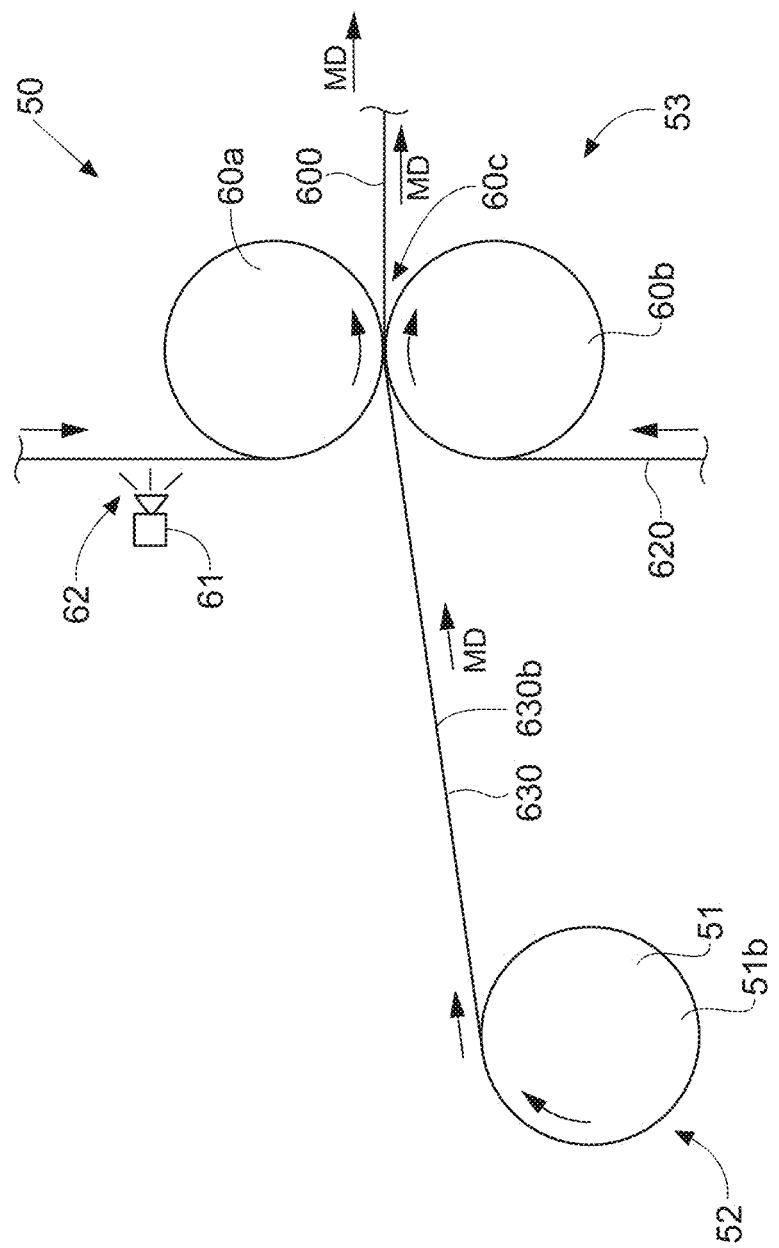
FIG. 2 is a schematic side view of a configuration of components for manufacturing a stretch laminate.

A process for manufacturing a stretch laminate is schematically depicted in FIG. 2. Elastic material 630 may be drawn from one or more spools, beams or supply rolls 51, into a nip between a pair of laminating rollers 60a, 60b. The laminating rollers also may simultaneously draw a first web layer material 610 and a second web layer material 620 into the nip therebetween, such that the elastic material 630 is sandwiched between the first web layer material and the second web layer material. The equipment of the system and/or laminating rollers may be configured to bond or otherwise affix the layers 610, 620 to each other and/or to the elastic material, so that a cohesive stretch laminate 600 is produced. In some examples an adhesive 62 may be applied to a facing surface of one or both web layers by an adhesive applicator 61, whereby the cohesive laminate is adhesively bonded when the layers are compressed together in nip 60c. In some examples adhesive may be applied by an applicator to the elastic material 630 before it enters the nip. In other examples, laminating rollers may be configured with features and equipment to effect mechanical/compression/thermal bonding of the layers in a pattern of bonds, as the layers pass through the nip. In some examples the laminating rollers may be configured to effect a pattern of ultrasonic bonds; and in some examples a sonotrode may be substituted for one of the laminating rollers. Examples of various processes and types of bonding of layers to form a stretch laminate are described in the co-pending application filed on the same date of filing of the present application, with named inventors LaVon et al., Procter & Gamble 62/686,896, entitled "BEAMED ELASTOMERIC LAMINATE STRUCTURE AND TEXTURE."

It has been learned that a formed nonwoven web material as described herein may be advantageously used to form one or more layers of a stretch laminate material. In more particular examples, the formed nonwoven web material may be used to form the outward-facing layer of a stretch laminate material. Formed nonwoven web materials as described herein provide advantages over conventional nonwoven web materials including improved perceived and actual breathability (particularly through the presence of attenuated regions, described below) and any number and variety of design configurations of ordered arrangements of zones of build-up regions and attenuated regions, to aid in donning/application, to provide front/rear visual differentiation, appealing texture, and/or visual and esthetic effects.

Referring now to FIGS. 1A, 1B, 3, 4 and 11, a formed nonwoven web material 610 may be used to form one or more of the relatively non-elastic sandwiching web layers of a stretch laminate. The stretch laminate, in turn, may be used to form for example, one or both of the front belt portion 114 and rear belt portion 115, or other component (such as, for example, an elasticized side panel, ear or fastening member panel, waistband, leg band, etc.), of a pant, disposable diaper or other wearable article. Manufactured according to the process described herein, a nonwoven web material component may be formed to have an ordered arrangement 161 of zones 160 each including a first region 163 (also called an attenuated region 272 herein) and a second region 166 (also called a build-up region 271 herein). The ordered arrangement of zones reflects an ordered arrangement of airflow blocking structures on a forming belt 260, described below. As will be described below, the airflow blocking structures can be formed and configured on the forming belt in virtually unlimited ways to reflect virtually unlimited varieties of functional and esthetically pleasing design layouts, which in turn can be used to effect formation of a nonwoven web material with a configuration of zones 160 reflecting the desired ordered arrangement. In the non-limiting examples shown in FIGS. 4 and 11, ordered arrangement 161 of zones 160 are configured in a pattern defining heart shapes within scallop shapes.

Process for Manufacturing Formed Nonwoven Web Material

Formed nonwoven web material may be manufactured using equipment, processes and materials described in, for example, any of US Application Pub. Nos. US 2017/0191198; US 2017/0029994; US 2017/0029993 and US 2017/0027774, and U.S. application Ser. Nos. 15/840,455; 15/879,474; 15/879,477; 15/881,910; 62/527,216; and 62/527,224, the disclosures of which are incorporated by reference herein.

A formed nonwoven web material may be manufactured using a configuration of equipment adapted to spin nonwoven filaments from one or more polymer component resins according to a spunbond process, utilizing a specially adapted forming belt. For example, referring to FIG. 5, a process line 500 for manufacturing a nonwoven web of bicomponent filaments may include a pair of melt extruders 532 and 534, driven by extruder drives 531 and 533, respectively, for separately melting and extruding a first polymer component resin and a second polymer component resin. The first polymer component resin may be fed into the respective extruder 532 from a first hopper 536 and the second polymer component resin may be fed into the respective extruder 534 from a second hopper 538. The first and second polymer component resins may melted and driven by the extruders 532 and 534 through respective polymer conduits 540 and 542 then through filters 544 and 545, to melt pumps 546 and 547, which help pump the polymer into and through a spin pack 548. Spin packs with spinnerets used in spinning bicomponent filaments are known in the art and therefore are not described here in great detail.

Generally described, a spin pack 548 may include a housing which includes a plurality of plates stacked one on top of the other with a pattern of openings arranged to create flow paths for directing the melted first and second polymer component resins separately through spinneret openings. The spin pack 548 may have spinneret openings arranged in one or more rows. As the melted polymer resins are forced through them, the spinneret openings emit a downward curtain of individual melted polymer streams 122a. For the purposes of the present disclosure, spinnerets may be arranged to form streams for sheath/core or side-by-side bicomponent filaments. Bicomponent filaments may be preferred in some circumstances for their particular characteristics. Side-by-side or eccentric or asymmetric core/sheath bicomponent filaments may be preferred where it is desired that the spun filaments have a spiral or curl induced by differing cooling contraction rates of differing components, wherein spiral or curl in the spun filaments may contribute to enhanced loft and bulk of the nonwoven web material. Core/sheath bicomponent filaments may be preferred where it is desired that the respective components have differing attributes or properties that might be advantageously balanced. Such attributes or properties might include raw material (resin) cost, or spun tensile strength, or surface feel or surface friction. In one example, a core/sheath filament in which the core component is predominately polypropylene and the sheath component is predominately polyethylene may be preferred, wherein polypropylene is selected for the core component for its relatively lower cost and contribution to filament tensile strength, and polyethylene is selected for the sheath component for a relatively lower melting point (for purposes of thermal bonding between filaments) and a relatively lower-friction, silkier feel it imparts to the filament surfaces.

Although the above description contemplates spinning bicomponent filaments, it will be appreciated that the equipment and materials supplied may be adapted, selected and configured to spin monocomponent filaments, or multicomponent filaments having more than two components.

Spinnerets may be configured and adapted to form streams with generally circular cross-sections (to form filaments with generally round/circular cross sections), or streams with generally non-round cross sections such as asymmetric, multi-lobal, e.g., trilobal cross sections (to form asymmetric, lobed, e.g., trilobal filaments). Lobed filaments may be desired in some circumstances for their effects on fluid flow along their surfaces, for their effects on filament and nonwoven opacity, for their effects on fiber and nonwoven feel, or a combination of these effects. Generally, a nonwoven web material formed of lobed filaments such as trilobal filaments has greater opacity than an otherwise comparable nonwoven web material formed of round filaments, as a result of greater light refraction and/or diffusion through trilobal filaments. Fluid flow along filament surfaces may be enhanced or inhibited to a greater extent by lobed cross sections, depending upon whether the surfaces of the filaments are hydrophilic or hydrophobic, respectively.

The process line 530 also may include a quench blower 550 positioned beneath/adjacent the location the polymer streams 122a exit the spinnerets. Temperature, velocity and direction of air from the quench air blower 550 may be suitably controlled to quench the polymer streams, causing them to partially solidify. Quench air may be provided and directed at one (upstream or downstream) side of the curtain or both sides of the curtain.

An attenuator 552 may be positioned below the spinneret to receive the quenched polymer streams 122a. Filament draw units or aspirators for use as attenuators in melt spinning polymers are known in the art. Suitable filament draw units for use in the process of the present disclosure may include a linear filament attenuator of the type shown in U.S. Pat. No. 3,802,817, or eductive guns of the type shown in U.S. Pat. Nos. 3,692,618 and 3,423,266, the disclosures of which are incorporated herein by reference.

Generally, the attenuator 552 may include and define an elongate vertical passage in which the polymer streams 122a may be entrained in a downward air stream, drawn downward, elongated and reduced in cross section to form filaments 122. A shaped, at least partially foraminous forming belt 260 is positioned below the attenuator 552 and receives the downward-moving continuous filaments from the outlet opening of the attenuator 552. The forming belt 260 is a continuous belt, having an outer receiving side 260a and an inner side 260b, and cycles about guide rollers 562, one or more of which may be driven at a controlled speed to cause the belt to move translate along an x-y plane and along a machine direction MD through a working location 561 beneath the attenuator. A forming vacuum system 555 may be positioned below the working location 561 of the belt 260 where the filaments are deposited, to draw the air of the air stream through the belt, and thereby draw the entrained filaments toward and against the belt surface. Although the forming belt 260 is shown and described as a belt herein, it will be understood that a forming device with a suitable forming surface may also have other forms, such as a rotatable drum with a suitable cylindrical forming surface. Features of examples of shaped forming belts are described below.

In operation of the process line 500, the hoppers 536 and 538 may be supplied with the respective desired first and second polymer component resin(s). First and second polymer component resin(s) may be melted by the respective extruders 532 and 534, and forced in their melted state through polymer conduits 540 and 542 to spin pack 548. The line may include filters 544, 545 to filter out solid impurities from the melted resins, and the line may also include supplemental melt pumps 546, 547 to increase pressure in the conduits and thereby assist in driving the polymer components to and through the spin pack 548. Although the temperatures of the melted polymer resins can be controlled and varied for the polymers used and desired process conditions, when one or both of polyethylene and polypropylene are predominately the component resins, the temperatures of the melted polymer resins may be controlled to be within a range from about 190 deg. C. to about 240 deg. C.

Non-limiting examples of particularly suitable polymeric resins for spinning bicomponent filaments contemplated herein include PH-835 polypropylene obtained from LyondellBasell (Rotterdam, Netherlands) and ASPUN-6850-A polyethylene obtained from Dow Chemical Company (Midland, Michigan, USA). In some examples bicomponent filaments may be spun from differing resin formulations for each component—each based upon polypropylene, but having differing melt temperatures and/or cooling contraction rates.

In some examples, all filaments forming layers 610 and/or 620 may be spun from synthetic polymeric resin materials. Although synthetic, petroleum-derived polypropylene and polyethylene are contemplated as the most likely selected predominant polymer resin constituents for spinning filaments, due to their thermodynamic and mechanical attributes and their costs at the present time, a wide variety of polymers may be suitable for use within the scope of the present disclosure. Non-limiting examples of other potentially suitable synthetic polymers include thermoplastic polymers, such as polyesters, polyethylene terephthalate, nylons, polyamides, polyurethanes, polyolefins (such as polypropylene, polyethylene and polybutylene), polyvinyl alcohol and polyvinyl alcohol derivatives, sodium polyacrylate (absorbent gel material), and copolymers of polyolefins such as polyethylene-octene or polymers comprising monomeric blends of propylene and ethylene, and biodegradable or compostable thermoplastic polymers such as polylactic acid, polyvinyl alcohol, and polycaprolactone. Potentially suitable natural polymers include starch, starch derivatives, cellulose and cellulose derivatives, hemicellulose, hemicelluloses derivatives, chitin, chitosan, polyisoprene (cis and trans), peptides and polyhydroxyalkanoates. In one example, a predominate polymer component for spinning filaments may be a thermoplastic polymer selected from the group consisting of: polypropylene, polyethylene, polyester, polylactic acid, polyhydroxyalkanoate, polyvinyl alcohol, polycaprolactone, styrene-butadiene-styrene block copolymer, styrene-isoprene-styrene block copolymer, polyurethane, and mixtures thereof. In another example, the thermoplastic polymer may be selected from the group consisting of: polypropylene, polyethylene, polyester, polylactic acid, polyhydroxyalkanoate, polyvinyl alcohol, polycaprolactone, and mixtures thereof. Alternatively, the polymer may comprise one derived from monomers which are partially produced by biological processes, such as bio-polyethylene or bio-polypropylene.

In some circumstances it may be desired to manipulate and/or the enhance features of the spun filaments such as color, opacity, pliability, hydrophilicity/hydrophobicity and/or surface feel (e.g., surface coefficient of friction) of. In such circumstances one or more melt additives may be included with the polymer component resin(s) fed to the extruder(s).

Inorganic fillers such as the oxides of magnesium, aluminum, silicon, and titanium may be added to the polymer resins as whiteners, opacifiers, fillers or processing aides. Other inorganic materials that may serve one or more of these purposes may include hydrous magnesium silicate, titanium dioxide, calcium carbonate, clay, chalk, boron nitride, limestone, diatomaceous earth, mica glass quartz, and ceramics.

Slip agent melt additives may be included in an amount sufficient to affect and/or enhance desired haptic properties (e.g., impart a soft/silky/slick feel) to the filaments. Some slip agents when melt-blended with a polymer component resin gradually migrate to the filament surfaces during or after cooling, forming a thin coating on the filament surfaces, having lubricating effects. It may be desired that the slip agent be a fast-bloom slip agent, and can be a hydrocarbon having one or more functional groups selected from hydroxide, aryls and substituted aryls, halogens, alkoxys, carboxylates, esters, carbon unsaturation, acrylates, oxygen, nitrogen, carboxyl, sulfate and phosphate. In one particular form, the slip agent is a salt derivative of an aromatic or aliphatic hydrocarbon oil, notably metal salts of fatty acids, including metal salts of carboxylic, sulfuric, and phosphoric aliphatic saturated or unsaturated acid having a chain length of 7 to 26 carbon atoms, preferably 10 to 22 carbon atoms. Examples of suitable fatty acids include the monocarboxylic acids lauric acid, stearic acid, succinic acid, stearyl lactic acid, lactic acid, phthalic acid, benzoic acid, hydroxystearic acid, ricinoleic acid, naphthenic acid, oleic acid, palmitic acid, erucic acid, and the like, and the corresponding sulfuric and phosphoric acids. Suitable metals include Li, Na, Mg, Ca, Sr, Ba, Zn, Cd, Al, Sn, Pb and so forth. Representative salts include, for example, magnesium stearate, calcium stearate, sodium stearate, zinc stearate, calcium oleate, zinc oleate, magnesium oleate and so on, and the corresponding metal higher alkyl sulfates and metal esters of higher alkyl phosphoric acids.

In other examples, the slip agent may be a non-ionic functionalized compound. Suitable functionalized compounds include: (a) esters, amides, alcohols and acids of oils including aromatic or aliphatic hydrocarbon oils, for example, mineral oils, naphthenic oils, paraffinic oils; natural oils such as castor, corn, cottonseed, olive, rapeseed, soybean, sunflower, other vegetable and animal oils, and so on. Representative functionalized derivatives of these oils include, for example, polyol esters of monocarboxylic acids such as glycerol monostearate, pentaerythritol monooleate, and the like, saturated and unsaturated fatty acid amides or ethylenebis(amides), such as oleamide, erucamide, linoleamide, and mixtures thereof, glycols, polyether polyols like Carbowax, and adipic acid, sebacic acid, and the like; (b) waxes, such as carnauba wax, microcrystalline wax, polyolefin waxes, for example polyethylene waxes; (c) fluoro-containing polymers such as polytetrafluoroethylene, fluorine oils, fluorine waxes and so forth; and (d) silicon compounds such as silanes and silicone polymers, including silicone oils, polydimethylsiloxane, amino-modified polydimethylsiloxane, and so on.

Fatty amides that may be useful for purposes of the present disclosure are represented by the formula: $RC(O)NHR^1$, where R is a saturated or unsaturated alkyl group having of from 7 to 26 carbon atoms, preferably 10 to 22 carbon atoms, and R1 is independently hydrogen or a saturated or unsaturated alkyl group having from 7 to 26 carbon atoms, preferably 10 to 22 carbon atoms. Compounds according to this structure include for example, palmitamide, stearamide, arachidamide, behenamide, oleamide, erucamide, linoleamide, stearyl stearamide, palmityl palmitamide, stearyl arachidamide and mixtures thereof.

Ethylenebis(amides) that may be useful for purposes of the present disclosure are represented by the formula:

$$RC(O)NHCH_2CH_2NHC(O)R,$$

where each R is independently is a saturated or unsaturated alkyl group having of from 7 to 26 carbon atoms, preferably 10 to 22 carbon atoms. Compounds according to this structure include for example, stearamidoethylstearamide, stearamidoethylpalmitamide, palmitamidoethylstearamide, ethylenebisstearamide, ethylenebisoleamide, stearylerucamide, erucamidoethylerucamide, oleamidoethyloleamide, erucamidoethyloleamide, oleamidoethylerucamide, stearamidoethylerucamide, erucamidoethylpalmitamide, palmitamidoethyloleamide and mixtures thereof.

Commercially available examples of products containing potentially suitable fatty amides include AMPACET 10061 (Ampacet Corporation, White Plains, New York, USA) which comprises 5 percent of a 50:50 mixture of the primary amides of erucic and stearic acids in polyethylene; ELVAX 3170 (E.I. du Pont de Nemours and Company/DuPont USA, Wilmington, Delaware, USA) which comprises a similar blend of the amides of erucic and stearic acids in a blend of 18 percent vinyl acetate resin and 82 percent polyethylene. Slip agents are also available from Croda International Plc (Yorkshire, United Kingdom), including CRODAMIDE OR (an oleamide), CRODAMIDE SR (a stearamide), CRODAMIDE ER (an erucamide), and CRODAMIDE BR (a behenamide); and from Crompton, including KEMAMIDE S (a stearamide), KEMAMIDE B (a behenamide), KEMAMIDE O (an oleamide), KEMAMIDE E (an erucamide), and KEMAMIDE (an N,N'-ethylenebisstearamide). Other commercially available slip agents include ERUCAMID ER erucamide.

Other suitable melt additives for softness/reduction of the filament surface coefficient of friction include erucamide, stearamide, oleamide, and silicones e.g. polydimethylsiloxane. Some specific examples include CRODAMIDE slip & anti-block agents from Croda International Plc (Yorkshire, United Kingdom), and slip BOPP agents from Ampacet Corporation (White Plains, New York, USA). Some additional specific examples of softness/reduction of the coefficient of friction melt additives specifically tailored for polypropylene available from Techmer PM company (Clinton, Tennessee, USA) include additives sold under the trade designations PPM16368, PPM16141, PPM11790, PPM15710, PPM111767, PPM111771, and PPM12484. Some specific examples of additives specifically tailored for polyethylene available from Techmer PM include additives sold under the trade designations PM111765, PM111770, and PM111768.

Nonwoven web materials within contemplation of the present disclosure may include slip agents/softness melt additives independently, or in conjunction with other additives that affect the surface energy (hydrophilicity/hydrophobicity), or in conjunction with other filament feature variations including but not limited to filament size, filament cross-sectional shape, filament cross-sectional configuration, and/or curled filament variations. In examples of nonwoven web materials including two or more web layers, or two or more deposited layers of differing filaments, additives may be included in filaments of one layer but not the other, or differing additives may be included in filaments of differing layers.

Polymer component resins to be melt spun may also include coloring agents such as tinting or pigmenting agents, and/or whitening and/or opacifying agents. In some examples, all of the filaments and/or fibers forming the nonwoven web material may be tinted or pigmented. Alternatively, referring to FIG. 10B, a second layer 281, of nonwoven material, or of deposited, spun filaments and/or fibers may also include filaments and/or fibers spun from polymer resin blended with a tinting and/or pigmenting agent, to impart a color to the filaments and/or fibers that contrasts with the color of the filaments and/or fibers in first layer 280a. This may be desired for enhancing the visual impact of the ordered arrangement of zones, the attenuated regions 272 and build-up regions 271 (see description below) of the web material. In one non-limiting example, filaments and/or fibers of the first layer 280a may include no tinting or pigmenting agents, while filaments and/or fibers of the second layer 281 may include one or more tinting or pigmenting agents. In another non-limiting example, filaments and/or fibers of the first layer 280a may include a whitening and/or opacifying agent (such as, for example, $TiO_2$), and filaments and/or fibers of the second layer may include a coloring agent such as a non-white pigmenting or tinting agent. It will be appreciated that these and other combinations of tinting, whitening, opacifying and/or pigmenting agents may be used to impart visible color contrast between first and second layers forming the web material. In still other examples, underlying materials such as the elastic material 630 and/or the opposing sandwiching layer of the stretch laminate may include whitening, tinting or pigmenting agents selected to provide visual contrast with the formed nonwoven web material layer of the stretch laminate.

Pigmenting, whitening and/or opacifying agents may be obtained pre-dispersed in carrier resins, in color masterbatch products, suitable for blending with filament component resin(s) prior to or during introduction into the extruder(s). The agent(s) selected are preferably solid, powdered compositions that do not dissolve in or react chemically with the polymer resins when blended and dispersed within the filament component resins as they are melted, extruded and spun into filaments under ordinary melt-spinning process conditions. Suitable pigmenting agents may include solid inorganic or organic compositions, and in some examples may be solid organometallic compositions.

Suitable white pigment masterbatch products typically include solid metallic and/or organometallic compositions, for example, Antimony White, Barium Sulfate, Lithopone, Cremnitz White, Titanium White ($TiO_2$), and Zinc White (ZnO).

In some examples, filaments forming the finished nonwoven web 280, or at least a first layer 280a thereof, may be spun from polymer resin(s) to which a blue pigmenting agent has been added. The inventors believe that an appropriate concentration of blue pigment added to the filament component resin may have a dramatic impact on visibility of the zones and regions thereof in the ordered arrangement, enhancing the appearance of z-direction depth and overall three-dimensional structure. Without intending to be bound by theory, the inventors believe that other single pigments or combinations of pigments, admixed with the filament resin(s) to select weight percent concentrations, may be selected to have a similar effect on enhancing the visibility of apparent depth and/or visibility of three-dimensional structural features of the nonwoven web 280.

Suitable blue pigment masterbatch products typically also include solid metallic and/or organometallic compositions, for example, Ultramarine, Persian Blue, Cobalt Blue, Cerulean Blue, Egyptian Blue, Han Blue, Azurite, Prussian Blue, YImMn Blue and Manganese Blue. In a particular example, a blue color masterbatch product may be admixed to a concentration of approximately 0.25% of total weight polypropylene filament spinning resin, where the masterbatch product comprises approximately 36% by weight blue pigment composition. It is believed that an effective weight percent concentration of blue pigment material within the total spinning resin blend, for purposes of enhancing visibility of apparent depth and/or visibility of three-dimensional structural features of the nonwoven web 280 as described above, may be from approximately 0.03 percent to approximately 0.15 percent, more preferably from approximately 0.06 percent to 0.12 percent.

In yet another approach, an ink of a non-white color or color that contrasts with the spun filament color, may be applied via any suitable technique to the surface of the nonwoven web material that will become the visible surface of a stretch laminate layer, to enhance visual impact as described above.

In other examples, it may be preferred that substantially no pigments and/or whitening and/or opacifying agents be added to the component resin(s) used to spin the filaments of one or both sandwiching layers. In some circumstances, an effective concentration of a pigmenting, whitening or opacifying agent in the filaments may decrease the ability of the nonwoven web material formed therefrom to transfer/transmit heat such as body heat. In some circumstances this may cause the nonwoven web material to serve as a more effective thermal insulator, causing it to retain body heat and to feel uncomfortably warm for a wearer of a pant or other article having the stretch laminate contemplated herein as a component.

Referring again to FIG. 5, during manufacture or in post-treatment or even in both, the component resins, the spun filaments, or the nonwoven web materials contemplated herein may be treated with surfactants or other agents to impart the filament surfaces with surface energy properties making them hydrophilic or hydrophobic as may be desired. This is generally known in the fields of manufacturing and converting nonwoven web materials used to make components of absorbent articles.

As the polymer streams 122a exit the spinnerets, a stream of quenching air from the quench blower 550 at least partially quenches the polymers forming the streams, and, for certain polymers, induces crystallization in the polymers. To increase the rate of crystallization/solidification if desired, the quench blower(s) may be configured to direct quench air in a direction approximately perpendicular to the length of the streams. The quenching air may be cooled or heated as deemed suitable to be at a temperature of about 0 deg. C. to about 35 deg. C. and a velocity from about 100 to about 400 feet per minute when it contacts the polymer streams. The streams may be quenched sufficiently to reduce their surface tackiness so as to prevent them from bonding or fusing together to any undesirable extent, upon contact therebetween, as they travel to and are deposited and accumulate on the forming belt 260.

After quenching, the polymer streams 122a may be drawn into the vertical passage of an attenuator 552 and entrained by downward air flow generated by the attenuator 552. The attenuator may in some examples be positioned 30 to 60 inches below the bottom of the spinnerets. The air flow generated by the attenuator moves at a higher downward velocity than that of the entering quenched polymer streams. The attenuating air flow entrains the polymer streams and draws them downwardly, and thereby elongates them and reduces the size(s) of their cross sections, thereby forming filaments 122.

The filaments 122 exit the attenuator 552 and travel downwardly substantially in a z-direction with respect to the cycling forming belt 260 moving along the machine direction MD through the working location 561, beneath the attenuator 552. The entraining air exiting the attenuator may be drawn through the air-permeable portions of the forming belt 260 by the forming vacuum system 555, and the filaments 122 are stopped in their z-direction travel by the outer receiving side 260a of the forming belt 260, are deposited and accumulate thereon, and then travel with the forming belt 260 in the machine direction along therewith. It will be appreciated that the rate of deposit and accumulation of the filaments on the forming belt 260 may be controlled by controlling the speed at which the forming belt is cycled, the rate at which the filaments are spun, or a combination of these. As will be further explained below, the forming belt 260 may be configured with features that affect localized rates and depths of accumulation of filaments across its overall surface area in the x-y plane, to result in formation of a batt of filaments 270 and subsequent finished nonwoven web material 280 with a desired ordered arrangement of zones with regions of differing basis weight and/or fiber and/or filament area density, and/or thickness or caliper.

In some circumstances it may be desired to include discrete filaments of differing compositions in the nonwoven web material. It will be appreciated that this may be accomplished by configuring equipment carrying differing polymer resins arranged in parallel or in series/sequentially to one or more combinations of spin pack(s), quenching equipment and attenuating equipment configured to spin filaments and direct them at the forming belt. In one non-limiting example, it may be desired that the nonwoven web material have layered deposits of filaments of differing compositions with, for example, differing coloration, differing translucency, differing tactile properties (e.g., differing coefficients of friction), differing levels of hydrophilicity/hydrophobicity, etc. Referring to FIG. 10B, in a particular example, it may be desired, for visual effect, that white filaments are predominately present proximate the outer surface 124 of an outward-facing layer of a stretch laminate material, while non-white, colored filaments are predominately present proximate the inner surface 123. It will be appreciated that, to produce such a configuration, the filament spinning equipment may be configured to spin and deposit a first layer 280a of white filaments onto the forming belt, and sequentially downstream in the process, to spin and deposit a second layer 281 of differing, non-white filaments over the white filaments, as the batt moves along a machine direction on the moving forming belt.

The process line 500 may further include one or more consolidating devices such as compaction rolls 570 and 572, which form a nip 570a in which the batt 270 may be compacted. Optionally, one or both compaction rolls 570, 572 may be heated to promote partial softening and plastic deformation of the filaments. It may be desired, further, to apply a combination of heat and pressure to the filaments in the nip 570a sufficient to induce some bonding between intermeshing/crossing filaments traveling through nip 570a.

Compaction facilitates neat removal of the batt 270 from the forming belt 260, and some bonding may enhance this effect as well as impart added machine- and/or cross-direction tensile strength to the finished material. The compaction rolls 570, 572 may be pair of smooth surface stainless steel rolls with independent heating controllers. One or both compaction rolls may be heated by electric elements or hot oil circulation. The gap between the compaction rolls may be controlled, e.g., hydraulically, to impose desired pressure on the batt as it passes through the nip 570a. In one example, with a forming belt caliper of 1.4 mm, and a spunbond nonwoven having a basis weight of 30 gsm, the nip gap between the compaction rolls 570, 572 may be about 1.35 to 1.50 mm.

Figure 5:
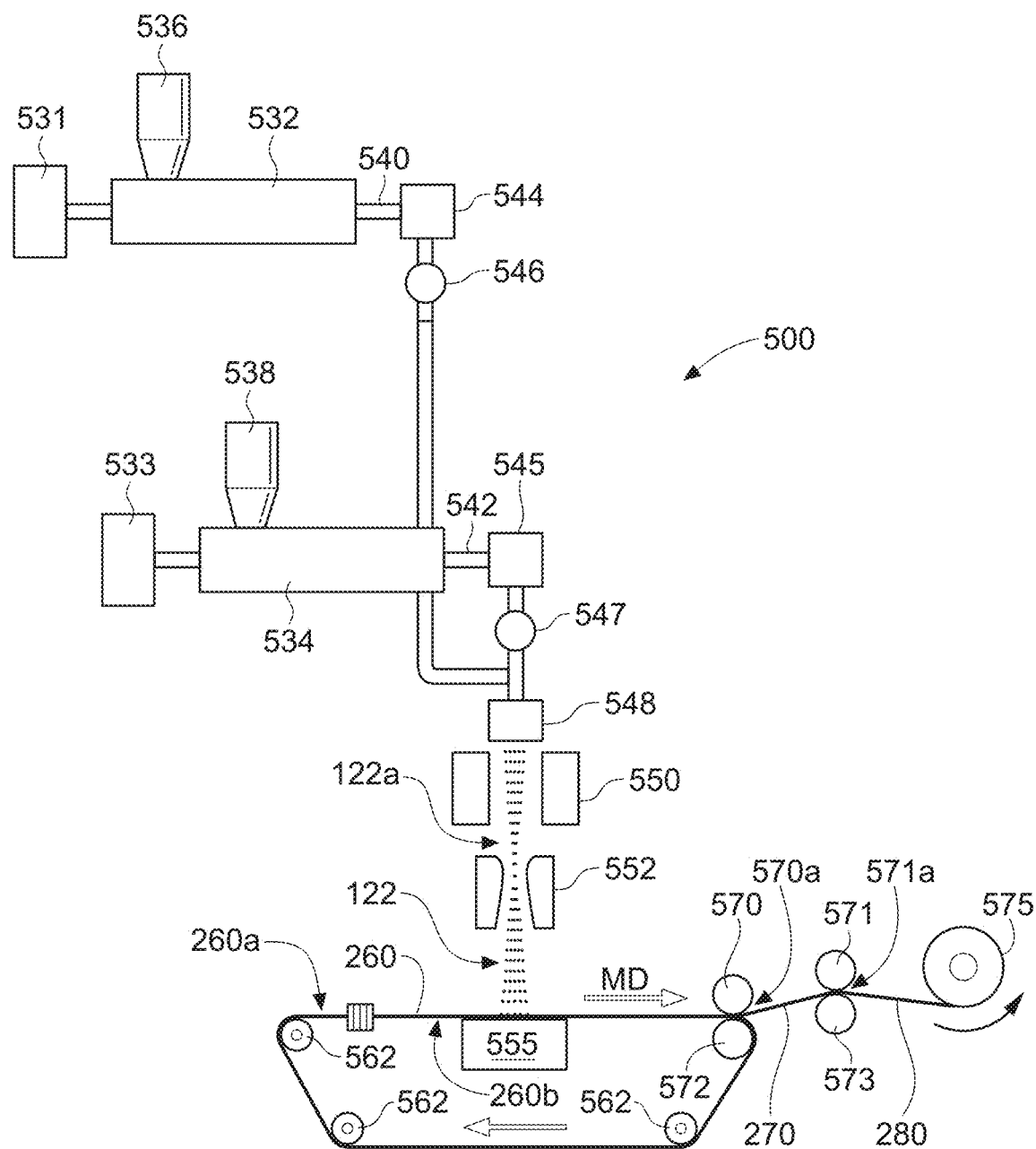
FIG. 5 is a schematic side view of a configuration of components for manufacturing a formed nonwoven web material.

In one example, upper compaction roll 570 may be heated to a temperature sufficient to induce melting of bond filaments on the upper surface of the batt 270, to impart cohesion and strength to the batt that may facilitate its removal from forming belt 260 without losing integrity. As shown in FIG. 5, for example, as rolls 570 and 572 rotate, forming belt 260 with the batt laid down on it enter the nip 570a between rolls 570 and 572. Heated roll 570 can heat the portions of nonwoven fabric 10 that are pressed against it most closely, by land surfaces 262a of airflow blocking structures 262 on forming belt 260 (described below), to deform and/or flatten and/or bond filaments proximate the upper surface (i.e., attenuator-side) surface of batt 270, to an extent desired. As can be understood by the description herein, the regions in which filaments are so deformed will reflect the pattern of the airflow blocking structures 261 on forming belt 260.

After compaction, the compacted batt may be lifted away or separated from the forming belt 260 and be directed through a second nip 571a formed by calender rolls 571, 573. The calender rolls 571, 573 may be stainless steel rolls, one having an engraved or otherwise formed pattern of raised bonding protrusions about its cylindrical surface (bonding roller), and the other being a smooth roll (anvil roller). The bonding roller, or both bonding and anvil rollers, may be heated such that they heat and partially melt the filaments so as to cause them to fuse together in the nip, between the radially outermost surfaces of the bonding protrusions and the anvil roller. The bonding protrusions on the bonding roller may be configured in any suitable regular pattern of bonding "pins" that will effect a like pattern of bonds in the finished web material 280. The radially outermost surfaces of the bonding protrusions effect localized elevated compression of the batt in the nip 571a, between the bonding protrusions and the anvil roller. These surfaces may have a cumulative surface area about the bonding roller that amounts to a percent fraction of the total cylindrical surface area of the working portion of the bonding roller (bonding area percentage), which will be approximately reflected in the percent fraction of the surface area, in the x-y plane, of the web material that is bonded (bonded area percentage). The bonding area percentage of the bonding roller, and the resulting bonded area percentage of the web material, may be approximately from 3% to 30%, from 6% to 20%, or from 7% to 15%. A pattern of thermal calender point-bonds may serve to improve cohesiveness of the web, and enhance machine direction and cross-direction tensile strength and dimensional stability, useful in downstream processing and in incorporation of the web material into finished products.

Additionally or alternatively, in some examples the batt may be bonded via a hot air bonding process. Through-air thermal bonding may be another approach to create higher loft nonwoven structures which may be desired in some circumstances. Through-air thermal bonding involves the application of hot air to the surface of the filament batt. The hot air flows through holes in a plenum positioned just above the nonwoven. However, the air is not pushed through the nonwoven, as in common hot air ovens. Negative pressure or suction, pulls the air through the open conveyor apron that supports the nonwoven as it passes thorough the oven. Pulling the air through the nonwoven fabric allows much more rapid and even transmission of heat and minimizes fabric distortion. As an alternative to use of a conventional through-air bonding unit, it is contemplated placing the bonding unit over the forming belt 260 while a vacuum is operated beneath the belt to draw hot air through the batt, effecting a process similar to that effected by a conventional through-air bonding unit.

Forming belt 260 may be made according to the methods and processes described in U.S. Pat. Nos. 6,610,173; 5,514,523; 6,398,910; or US 2013/0199741, each with the improved features and patterns disclosed herein for making spunbond nonwoven webs. The '173, '523, '910 and '741 disclosures describe belts that are representative of papermaking belts made with cured resin on a belt substrate member, which belts, with improvements and suitable configurations, may be utilized as described herein.

Forming belt 260 having three-dimensional features and patterns for making spunbond nonwoven webs can also be made by the following methods and processes and/or on the following apparatuses, including with modifications as desired for structures taught herein: rotary screen processes as taught in U.S. Pat. No. 7,799,382; polymer extrusion as taught in US 2007/0170610; resin system grafting as taught in U.S. Pat. No. 7,105,465; perforated film as taught in U.S. Pat. No. 8,815,057; successive layer treatment as taught in US 2006/0019567; polymeric droplet deposition as taught in U.S. Pat. No. 7,005,044; polymeric droplet deposition with a sacrificial material as taught in U.S. Pat. No. 7,014,735; air permeable film technology as taught by U.S. Pat. Nos. 8,454,800 or 8,822,009; multilayer belt structures as taught in US 2016/0090692; laser etching as taught by U.S. Pat. Nos. 8,758,569 or 8,366,878; extruded mesh technology as taught in US 2014/0272269; nonwoven belts as described in US 2008/0199655; and additive manufacturing methods and processes as taught in US 2015/0102526A1, or US 2016/0159007, or WO 2016/085704, or US 2016/0185041.

Figure 6:
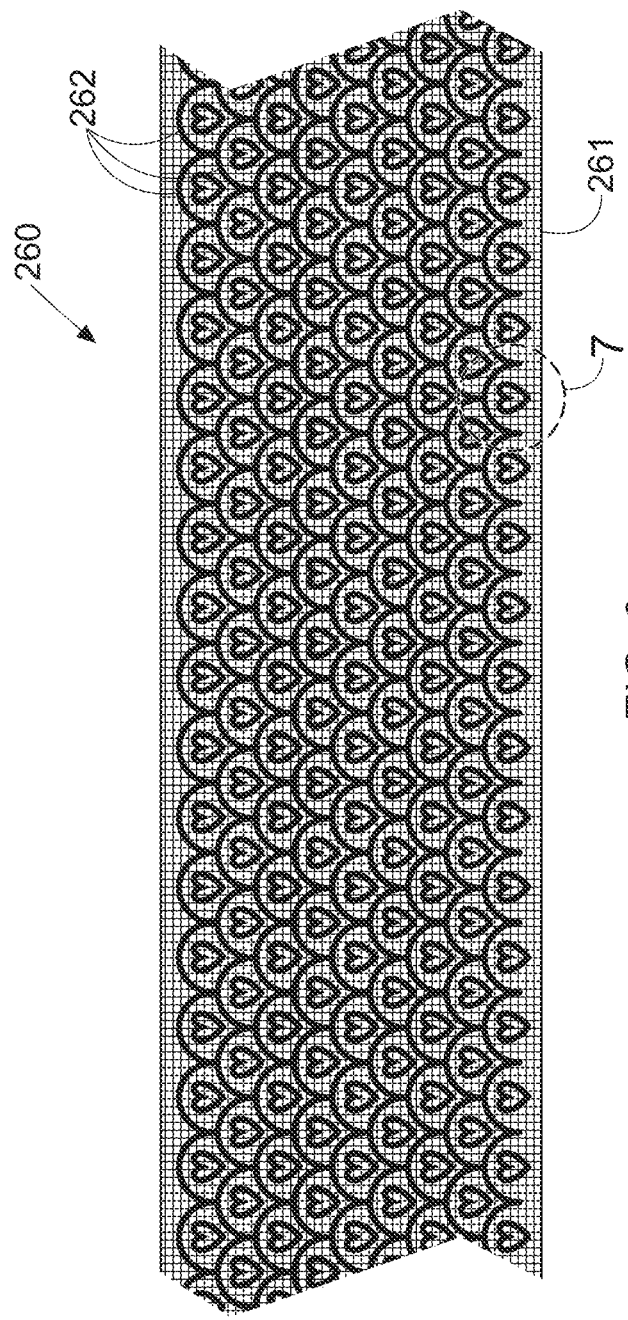
FIG. 6 is a plan view of an outer receiving side of a portion of a forming belt.
Figure 7:
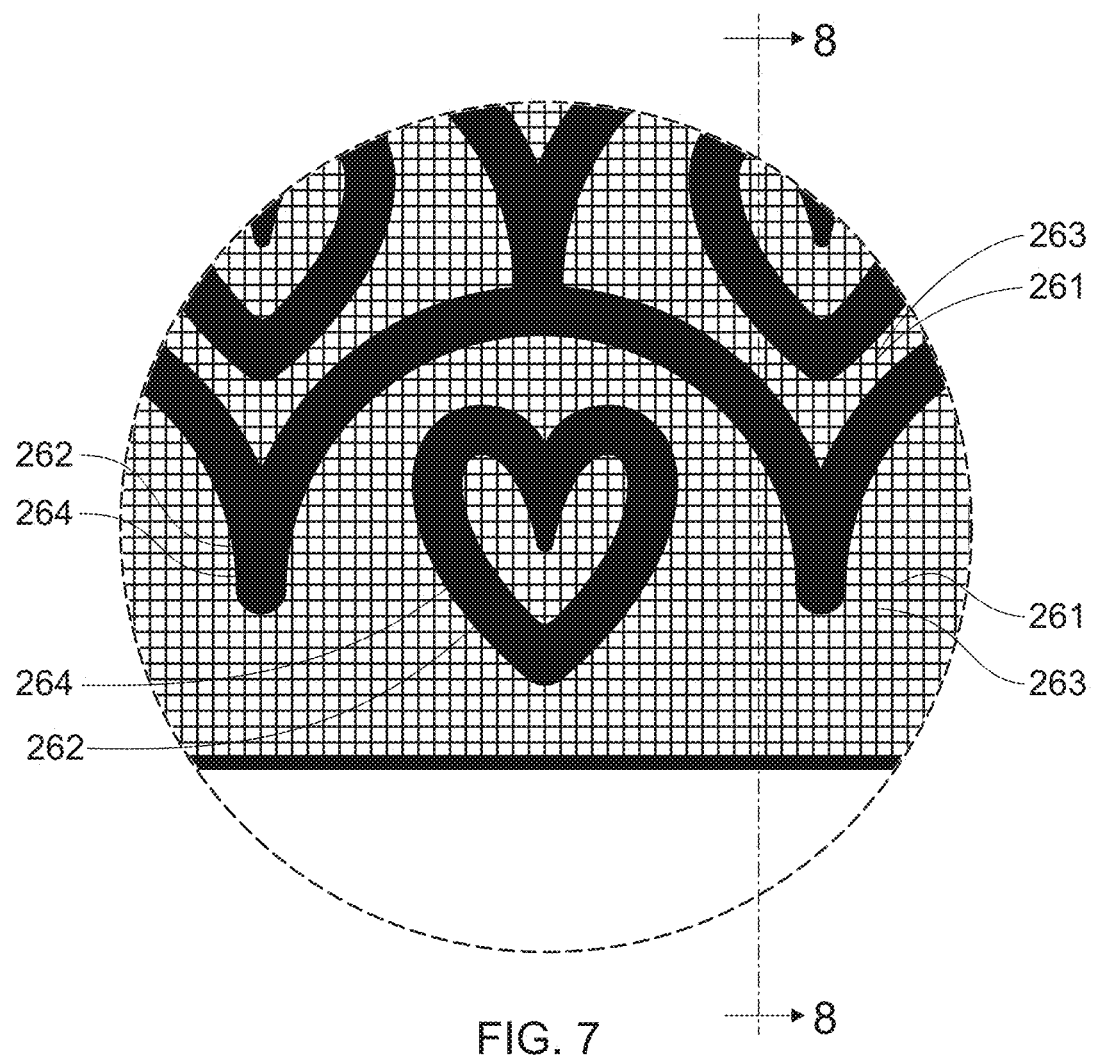
FIG. 7 is an expanded plan view of the portion of the forming belt identified as "7" in FIG. 6.
Figure 8B:
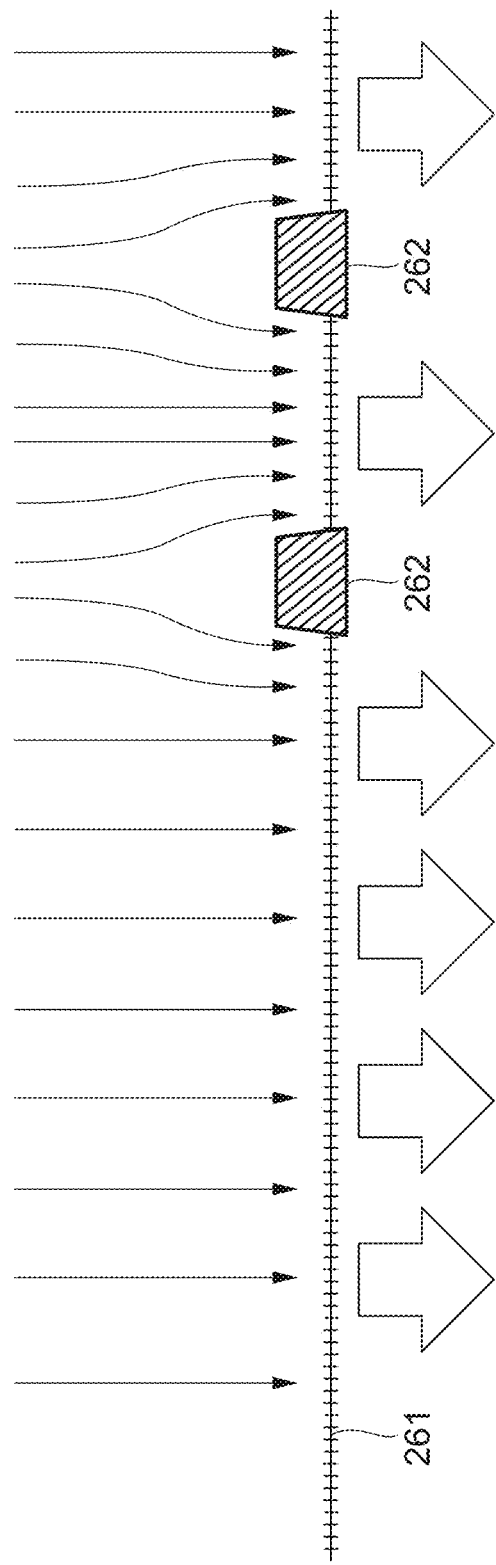
FIG. 8B is a schematic cross-section view of the portion of the forming belt shown in FIG. 7, taken along line 8-8 in FIG. 7, with arrows schematically illustrating air flow through the portion of the forming belt shown, when in use.

An example of portions of a forming belt 260 of the type useful for purposes of the present disclosure and which may be made according to the disclosure of U.S. Pat. No. 5,514,523, is shown in FIGS. 6, 7 and 8A. As taught in the '523 patent, a flat sheet of substrate belt material 261 is thoroughly coated with a liquid photosensitive polymeric resin to a preselected thickness. The substrate belt material 261 (called a "reinforcing structure" in the '523 patent) may be an air-permeable wire mesh or screen material, a woven mat or sheet material, an apertured metal or polymer sheet material, or any other material that provides suitable process dimensional stability and durability under conditions of use contemplated herein, and a relatively high degree of air permeability in a z-direction combined with a relatively small spacing and sizing of air passageways, such that spun filaments striking the belt will accumulate thereon rather than being blown or drawn through air passageways to any substantial extent, by air moving therethrough in the z-direction. A transparent film or mask printed with, or otherwise reflecting in the negative, opaque portions having defining a desired pattern, arrangement, sizes and shape(s) for desired airflow blocking structures 262, is laid down over the liquid photosensitive resin. The resin is then exposed to light of an appropriate wavelength through the film, such as UV light for a UV-curable resin. This exposure to light causes curing of the resin beneath the transparent portions (e.g., non-printed portions) of the mask. Uncured resin (beneath the opaque portions in the mask) may then be removed from the substrate (e.g., via use of a solvent), leaving behind solid, airflow blocking structures formed of the cured resin formed on the substrate, arranged in the desired pattern and shape(s), for example, the pattern of airflow blocking structures 262 shown in FIG. 12. Other patterns of airflow blocking structures for imparting any desired decorative or functional features to a nonwoven web material can also be formed. Airflow blocking structures 262 form and define airflow blocked regions 264 of forming belt 260, through which z-direction air flow through the belt is blocked. The portions of the substrate belt material 261 on which the resin was left uncured, and from which it was removed, form and define airflow permeable regions 263 of forming belt 260, through which z-direction air flow through the belt is permitted. The resin may be formed and cured on the belt to a depth and in a manner such that airflow blocking structures 262 have a desired z-direction depth, and flat land surfaces 262a generally along an x-y plane. Following formation of the airflow blocking structures, ends of the sheet of substrate belt material with the airflow blocking structures formed thereon may be joined in any suitable manner to form a continuous forming belt 260.

Figure 9:
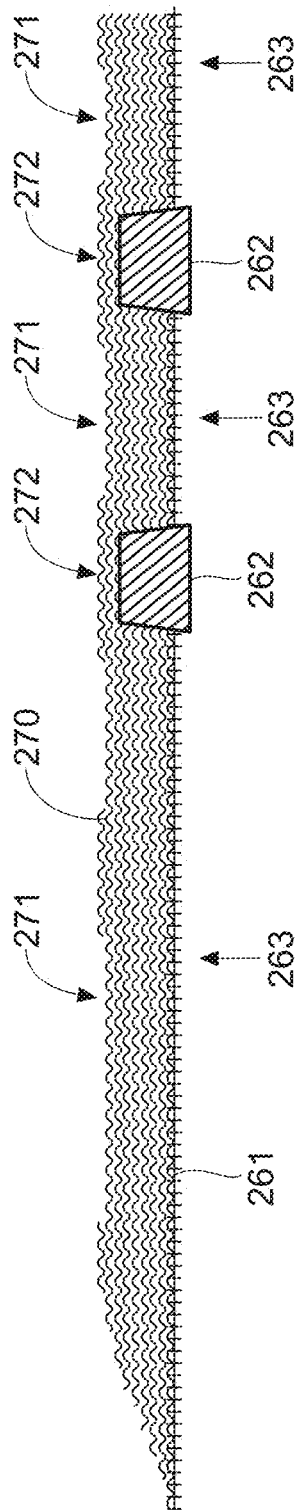
FIG. 9 is a schematic cross-section view of the portion of the forming belt shown in FIG. 7, taken along line 8-8 in FIG. 7, and shown with a schematic cross-section view of an accumulation of spun filaments deposited thereon.
Figure 10A:
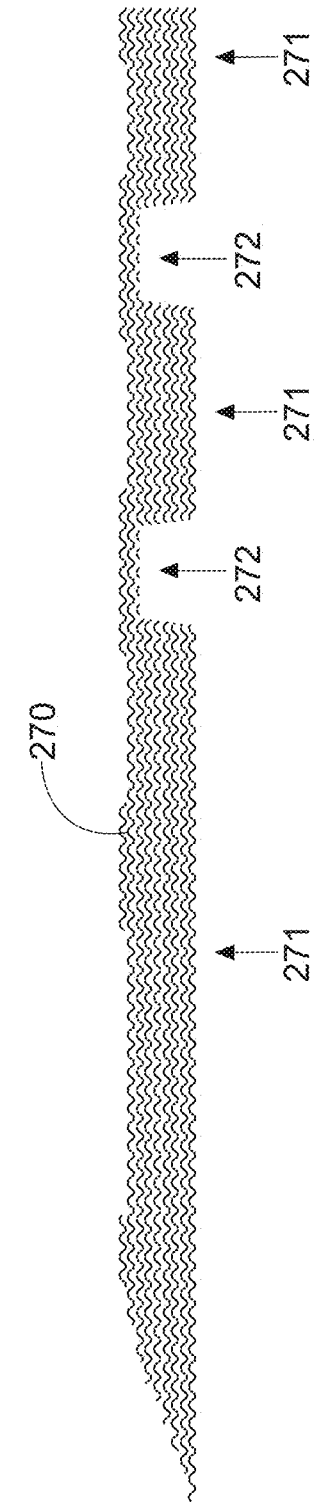
FIG. 10A is a schematic cross-section view of the accumulation of spun filaments shown in FIG. 9, shown apart from the forming belt.
Figure 10B:
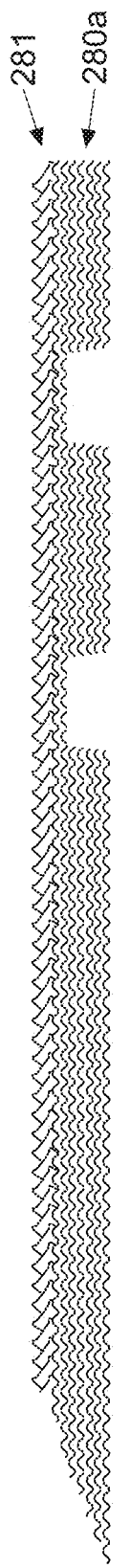
FIG. 10B is a schematic cross-section view of an accumulation of spun filaments similar to that shown in FIG. 9, shown apart from the forming belt, including first and second, differing layers of deposited filaments.
Figure 11:
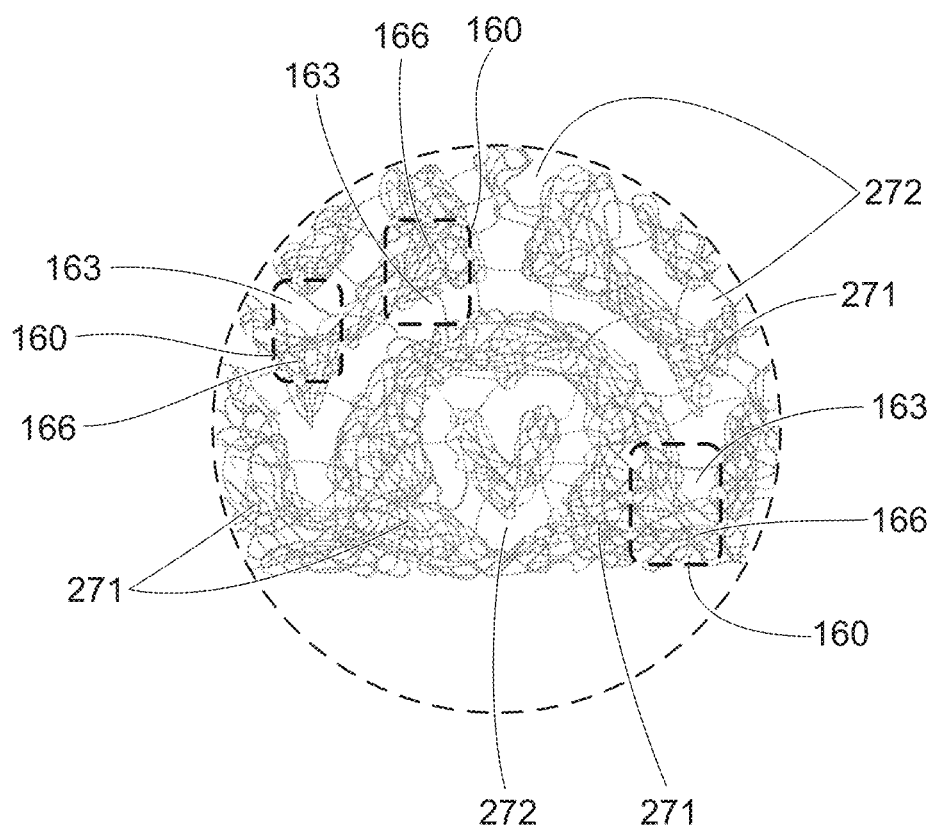
FIG. 11 is a schematic, enlarged plan view of a portion of an accumulation of spun filaments as may be formed on the forming belt shown in FIG. 6, within the portion of the forming belt identified as "7" in FIG. 6.

FIGS. 8B-11 schematically illustrate the manner in which spun filaments may be accumulated on forming belt 260, with the location and depth of filament accumulation being affected by the arrangement and depth of airflow blocking structures 262 on the forming belt. Because the filaments are entrained in attenuating air being driven downward and drawn through the belt in the z-direction by the forming vacuum system 555 (see FIG. 5) they follow the air as it finds its way around and past the blocking structures 262, and are deposited predominately on/over airflow permeable regions 263 of the forming belt. Accordingly, the filaments accumulate to a greater depth, fiber and/or filament area density and weight over the airflow permeable regions 263, to form build-up regions 271 of a batt 270 of filaments accumulated on the belt. The extent of filament accumulation on the forming belt, generally, may be controlled by controlling the belt cycling speed and the filament spinning rate, or a combination thereof. Turbulence and resulting randomness in the air flow as it approaches the belt, and machine direction movement of the belt, will cause smaller accumulations of filaments (which are generally continuous as spun) crossing over and thereby accumulating to a lesser extent over the land surfaces 262a of the airflow blocking structures 262, forming attenuated regions 272 in the batt 270 of accumulated filaments. This effect is schematically illustrated in FIGS. 9-11, which depict a relatively small accumulation of filaments 122 crossing through attenuated regions 272, as they may be formed by appropriately configured airflow blocking structures.

Following compaction between compaction rollers 571, 572 (shown in FIG. 5) and subsequent removal from the forming belt, as illustrated in FIG. 10A the batt 270 will have a structure with build-up regions 271 and attenuated regions 272 substantially corresponding to the arrangement of airflow blocking structures on the forming belt. As noted, filaments and/or portions thereof occupying the attenuated regions 271 may be somewhat plastically deformed (e.g., flattened) as a result of compaction between compaction roller 570 and the land surfaces 262a of the airflow blocking structures 262. Correspondingly, filaments and/or portions thereof occupying the build-up regions 271 generally will not be deformed by compaction or may be deformed to a substantially lesser extent, because during compaction they are disposed in the spaces between the airflow blocking structures and thus are not so closely compressed as the batt passes through compaction nip 270a.

Using a forming belt 260 and process as described above, a difference between the fiber and/or filament area density, and/or the basis weight, of the batt, of the build-up regions versus the attenuated regions can be achieved to a level of 2:1, 3:1 or even 4:1 or greater.

From the description above and the figures, it will also be appreciated that a formed nonwoven web material manufactured according to the process described will exhibit "sidedness," meaning a difference between features of its opposite major surfaces. Referring to FIGS. 9 and 10A, for example, it will be appreciated that the surface of the batt (and subsequent nonwoven web material) formed by filaments that reached the forming belt first in time (first-formed surface) will exhibit topographic features and/or texture, according to the ordered arrangement, that have substantially greater z-direction depth, than any topographic features and/or texture of the opposite surface, i.e., the surface formed by filaments that reached the forming belt last in time (last-formed surface), prior to compaction of the batt. As a result of such sidedness, visual discernibility of zones reflecting an ordered arrangement may be substantially greater on the first-formed surface (which may in some examples form the outer surface of an outward-facing layer of a stretch laminate). Consequently, the visual impact of the zones and of the resulting topographic/textural features may be more dramatic on the first-formed surface, than on the opposing last-formed surface. In conjunction therewith and with the method of manufacture, those portions of filaments occupying the attenuated regions will generally be closer in the z-direction, to the last-formed surface.

Although a melt spinning/spunbond process and deposition of filaments onto a forming belt is described above, it is also contemplated that other filaments and/or fiber deposition and basis weight distribution techniques and processes may be employed, including so-called co-forming processes described in, for example, U.S. Pat. Nos. 9,944,047; 8,017,534; 5,508,102; 4,100,324; and US 2003/0211802; PCT application publication number WO 2018/064595 A1; and US 2018/002848; US 2017/002486; US 2017/000695; US 2017/0342617; US 2016/0355950; and other techniques such as spunlace formation techniques in which a web formed of airlaid fibers (including natural and/or synthetic/polymeric fibers) have fiber location and distribution within the web material modified by controlled and ordered hydroenhancement/hydroentanglement, to form the ordered arrangement of attenuated regions and build-up regions contemplated herein.

An advantage provided by the forming belt manufacturing technique described above and in the references incorporated by reference in the present disclosure is that airflow blocking structures 262 may be formed and configured on a forming belt 260 according to any number of desired combinations of recognizable, visually discernible shapes, images of natural or artificial objects, people, animals, fanciful characters, anthropomorphic characters, decorative elements, alphanumeric characters, words, numbers, phrases, trademarks, logos, functional features, designs, patterns, sizes, spacings etc., by simply printing the negative of the desired configuration on the mask used to selectively block resin-curing light, as described above. It will be appreciated, therefore, that in addition to forming airflow blocking structures to impart the pattern of shapes depicted in FIG. 4, the airflow blocking structures may be designed and included on a forming belt to impart, without limitation, any of the types features listed above as may be desired, or any combination thereof, to the nonwoven web material.

Figure 15:
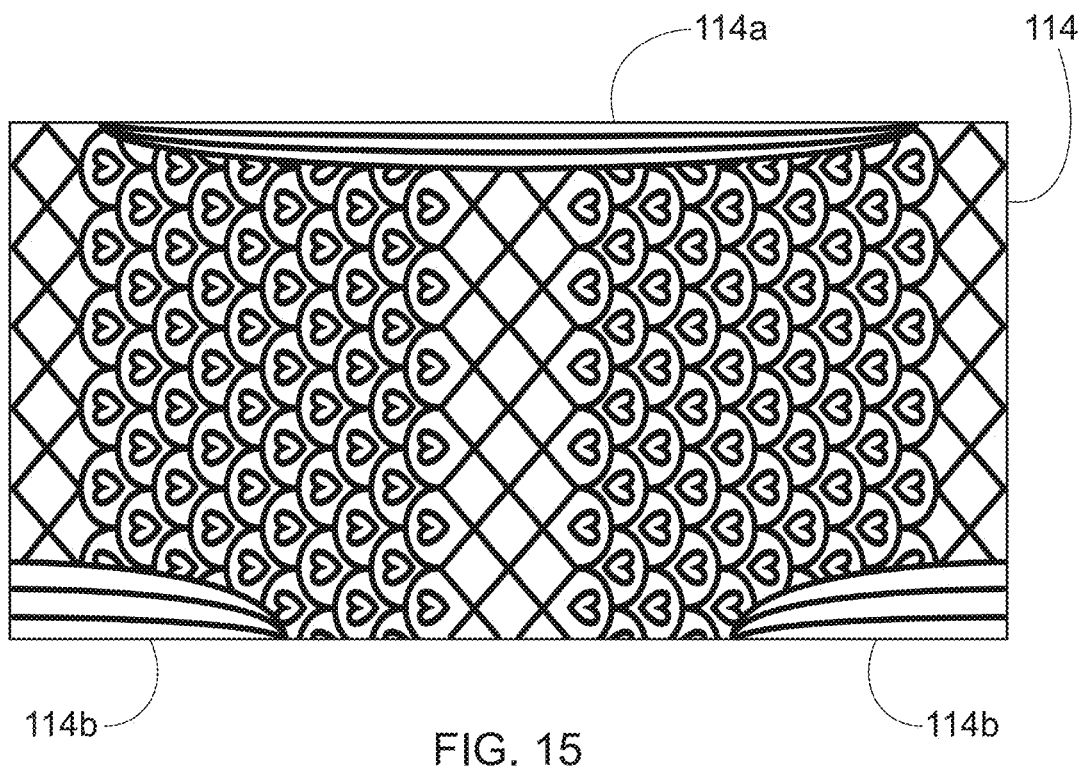
FIG. 15 is a plan view of a portion of a formed nonwoven material reflecting another example of an ordered arrangement of zones, suitable for use as a layer of a front belt portion of a pant article.
Figure 16:
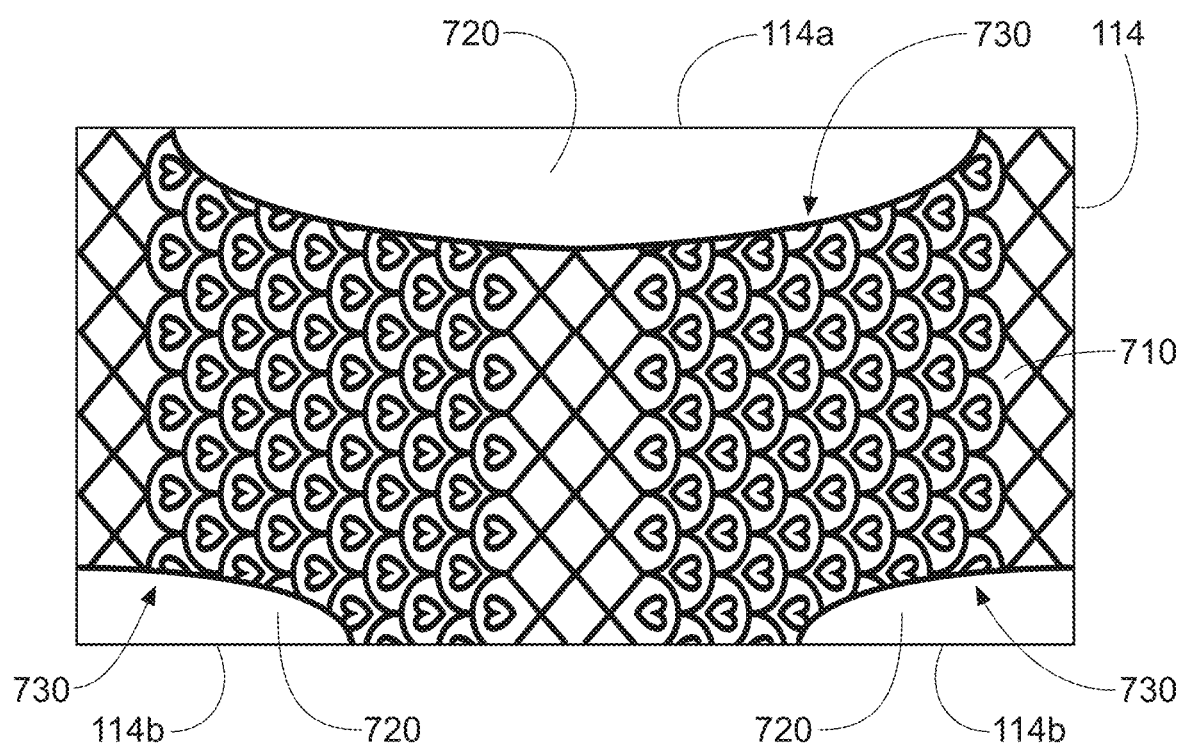
FIG. 16 is a plan view of a portion of a formed nonwoven material reflecting another example of an ordered arrangement of zones, suitable for use as a layer of a front belt portion of a pant article.
Figure 17:
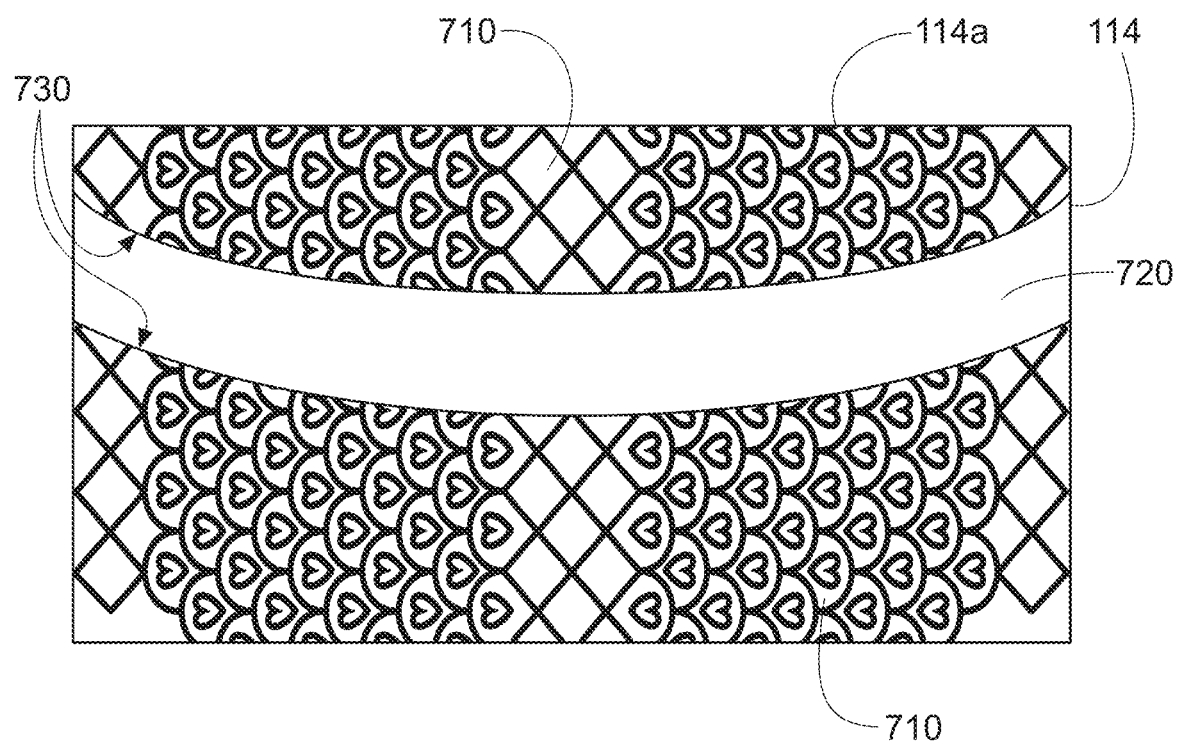
FIG. 17 is a plan view of a portion of a formed nonwoven material reflecting another example of an ordered arrangement of zones, suitable for use as a layer of a front belt portion of a pant article.

FIGS. 15-17 illustrate three possible, non-limiting examples. FIGS. 15-17 each depict a section of formed nonwoven web material that may be formed according to the process described herein, and used to form a layer, such as an outward-facing layer, of a section of stretch laminate material used, for example, to form a front belt portion of a pant. In one example, shown in FIG. 15, waist edge 114a and leg edges 114b may be visually accented by formed features that vary from decorative patterns and features appearing elsewhere on the section of formed nonwoven web material. In another pair of examples, shown in FIGS. 16 and 17, a first area 710 may be occupied by an ordered arrangement of zones 160, while one or more second areas 720 may be unoccupied by zones 160, and may have a substantially uniform basis weight and/or caliper, reflecting its manufacture on a forming belt with similar areas not occupied by airflow-blocking structures. In the example depicted in FIG. 16, unoccupied areas 720 may serve to visually accent a waist edge 114a and/or leg edges 114b of a section of nonwoven web material forming the outer layer of a stretch laminate, used to form, e.g., the outer layer of a front belt portion of a pant. In the example depicted in FIG. 17, the unoccupied area 720 may serve to visually cradle or hug the wearer's belly (e.g., when used as the outer layer of a stretch laminate material forming the front belt portion of a baby pant).

In some examples, an occupied area 710 or unoccupied area 720 on a stretch laminate forming a component of a wearable article may extend to and along an end edge or side edge of the laminate, and be substantially aligned with an occupied area 710 or unoccupied area 720 along an end edge or side edge of an adjoining component, the adjoining component also being formed of a formed nonwoven web material as described herein. The respective ordered arrangements of zones on the adjoining components may be substantially aligned such that they appear to be substantially continuous across the components, such that an embodied decorative pattern, design, image, etc., appears to continue across the seam, junction, etc. where the respective components meet. Thus, in such examples, unoccupied areas 720 may appear to continue across the respective adjoining components, with the respective perimeters or boundaries 730 thereof being substantially aligned where the adjoining components meet; and/or, embodied decorative designs, patterns, images, etc. reflected in occupied areas 710 appear to continue substantially uninterruptedly across the seam, junction, etc.

For purposes herein, an "unoccupied area" is distinguished from an "occupied area" by an absence of an attenuated region 270 over a continuous surface area of the formed nonwoven web material in its ungathered condition, equal to or greater than approximately 4 cm$^2$ and having no dimension in the x-y plane smaller than approximately 1 cm, the unoccupied area being delineated from the occupied area by a perimeter or boundary 730 demarking a discontinuity or interruption in the arrangement of zones 160. It may be appreciated that when an unoccupied area is of a certain size or larger, its local basis weight will tend toward an average between the local basis weights of proximate attenuated regions and build-up regions in the occupied areas. This occurs in unoccupied areas because filaments deposited on the associated forming belt 260 used to manufacture the formed nonwoven material, have not been diverted by entraining air away from airflow blocked regions 264, thereby accumulating more lightly thereover, to accumulate more heavily over airflow permeable regions 263 of a forming belt 260 (see FIGS. 8B and 9), to form attenuated regions 272 and build-up regions 271, during manufacture of the material. Thus, when an unoccupied region 720 of a formed nonwoven material reaches a certain size, it will have a local basis weight that is greater than the basis weight of proximate attenuated regions, and less than the basis weight of proximate build-up regions. The minimum size for an unoccupied area at which this condition begins to exist will depend upon the particular ordered arrangement for the formed nonwoven material that is designed and embodied in the forming belt used, and manufacturing process conditions such as filament size, spinning rate, forming belt speed, etc.

Stretch Laminate with Beamed Elastics

A stretch laminate having a sandwiching layer of formed nonwoven web material as described above may include any suitable form of elastic material 630. For example, the elastic material 630 may be an elastic film, an elastic scrim material, or a plurality of substantially parallel, spaced elastic strands substantially aligned with the stretch direction. In some examples, the elastic material 630 may be a plurality of elastic strands arranged in parallel and substantially aligned with the stretch direction, having a decitex of 470 to 940; having a longitudinal (cross direction, or cross-stretch direction) spacing of approximately 4 mm to approximately 10 mm (center-to-center) or greater, and having a manufacturing pre-strain greater (and typically substantially greater) than 150%.

Figure 3:
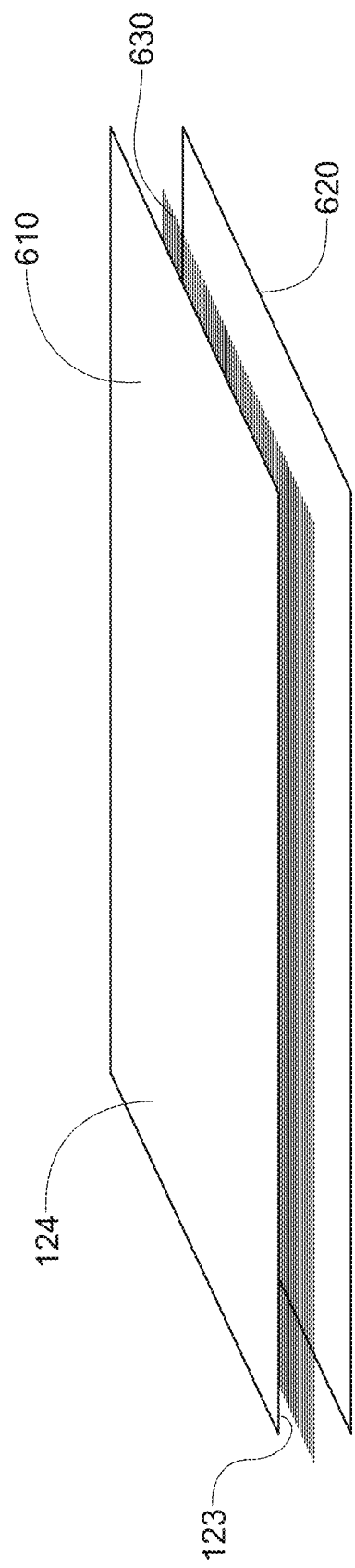
FIG. 3 is a schematic, exploded view of a components of a section of a stretch laminate.
Figure 4:
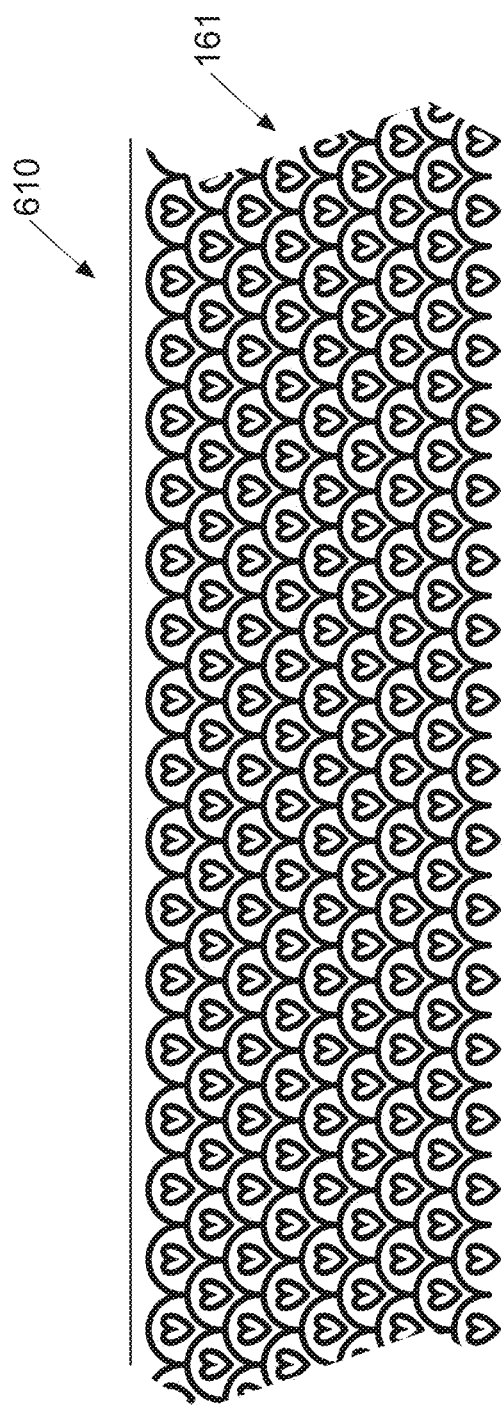
FIG. 4 is a plan view of a portion of a formed nonwoven web material forming a layer component of a stretch laminate, having one example of an ordered arrangement of zones.

In other examples, however, referring to FIGS. 2 and 3, elastic material 630 used as the elasticizing element of a stretch laminate may be beamed elastic strands, and the supply roll 51 may be one or more warp beams.

As noted above, stretch laminates in which conventional arrangements of elastic strands serve as the elasticizing mechanism are typified by relatively large, bulky gathers or ruffles of the sandwiching material layers when the laminate is in a partially or fully contracted condition. These relatively large, bulky gathers or ruffles will be present on both (outward-facing and wearer-facing) surfaces of the laminate, such that they will be in contact under pressure against the wearer's skin—in examples in which the laminate forms a component that contacts the wearer's skin—which can lead to increased chances of skin marking and wearer discomfort. Any decorative elements that may be included, such as printed graphic elements, tend to be folded up within the gathers or ruffles, and thus, distorted, partially concealed or otherwise rendered of substantially reduced visual impact. This would include features of a formed nonwoven material manufactured as described above, when used as a sandwiching layer for the stretch laminate.

It has been learned, however, that inclusion and use of beamed elastics as described herein provides for gathers of the sandwiching material layers that are greatly reduced in size and amplitude, and greatly increased in number or frequency per unit dimension of the stretch laminate along the stretch direction. It has been learned that, as a result, visibility and visual impact of any decorative elements that are printed or otherwise formed and included on the stretch laminate, may be substantially less impaired when the stretch laminate made with beamed elastics is in a contracted condition.

"Beamed elastics" as used herein refers to elastic strands that are provided, not on individual spools for each individual strand, but rather, as a plurality of strands that are of relatively low decitex, in relatively closely spaced arrangement, on a single spool or "beam". As they are unwound from the beam, they may be incorporated into a web product in such relatively closely spaced arrangement via suitable processing equipment and conditions. Beamed elastics have been used in various applications in textile and garment manufacturing for a number of years, but their potential usefulness for manufacturing elasticized components for wearable disposable absorbent articles has only recently been recognized. Stretch laminates improved via inclusion and use of beamed elastics may be used to form components for substantially improved fit, comfort, appearance and/or gasketing function about a wearer's waist, legs, crotch and sides.

A wearable disposable absorbent article in the form of a pant 110 is generally depicted in FIGS. 1A and 1B. A pant 110 may be designed to be donned by the wearer in a manner similar to that of a pair of durable underpants. A pant 110 may include discrete front and rear belt portions 114, 115 in the front waist region and rear waist region, respectively.

When a pant 110 includes front and rear belt portions 114, 115, the side edges of the front and rear belt portions may be joined permanently or refastenably to each other to form a waist opening having waist opening edges 114a, 115a and a pair of leg openings each having leg opening edges 114b, 115b. Front and rear belt portions 114, 115 formed of stretch laminate material provide an elastic extensibility feature that provides a comfortable and conforming fit, by initially conformably fitting the pant 110 to the wearer and sustaining this fit throughout the time of wear, including during the time the pant is loaded with bodily exudates, since the stretchable belt portions allow the waist-surrounding portions of the pant to expand and contract. Further, the elastomeric belt portions provide for ease of donning, and develop and maintain lateral/hoop tensile forces that help to maintain the pant in position on the wearer and enhance its fit.

A pant 110 including front and rear belt portions 114, 115 may include first and second side seams 116. One or both side seams 116 may be permanent (i.e., not non-destructively separable), and may be formed by joining a surface along a side edge of the front belt portion 114 to a surface along a side edge of the rear belt portion 114, via mechanical bonding, thermal bonding or adhesive bonding. Alternatively, one or both side seams may be separable and refastenable (i.e., non-destructively separable and refastenable following separation, effected by, e.g., a hook-and-loop fastening system).

Particularly regarding sections of stretch laminate material used to form one or both of front belt portion 114 and rear belt portion 115, referring to FIG. 3, a first web layer 610, and a second web layer 620, may form an outward-facing layer and a wearer-facing layer, respectively, of the stretch laminate material. One or both of the first and second web layers 610, 620 may be formed of nonwoven web material; and one or both of the first and second web layers 610, 620, for example, the outward-facing layer, may be formed of a formed nonwoven web material as described above. First and second web layers 610, 620 may be laminated about an elastic material 630 to form a stretch laminate, wherein the elastic material 630 is beamed elastics. As suggested in FIGS. 1A and 1B, a rear belt portion 115 of a pant may have a greater longitudinal dimension than the front belt portion 114. This length difference may be desired for purposes of providing for a higher leg opening edge 114b in front, accommodating more comfortable forward bending of the upper legs at the hips, while providing for a lower leg opening edge 115b in rear, providing for greater coverage of the wearer's buttocks, and a more underwear-like appearance of the pant 110. In some examples, one of layers 610 or 620 may be folded around and over the opposing surface to form an end edge of the laminate, about a fold line. In some examples in which the laminate includes elastic strands as the elastic material 630 extending in a stretch direction and is used to form a belt portion of a pant, web layer 610 may be folded around and over web layer 620, about a fold line substantially parallel with the elastic strands to form, for example, a waist edge of the belt portion.

Stretch laminates using elastic strands as the elasticizing element, and used to form elasticized belt portions in typically appearing in currently marketed pant products, typically include elastic strands having a decitex of 470 to 940 or even greater; have a longitudinal (cross direction, or cross-stretch direction) spacing of approximately 4 mm to 10 mm (center-to-center) or greater, and a manufacturing pre-strain greater (and typically substantially greater) than 150%. At typical combinations of values within these ranges, the non-elastic web material components of the stretch laminates form relative large, uncontrolled ruffles or gathers (also sometimes called "rugosities" or "corrugations"), of web material affixed to the strands, that are of a substantially low frequency (along the stretch direction) and substantially high z-direction amplitude or height, such that they are highly visible and impart a rough, mottled and bulky appearance to the laminate. Further, as the material ruffles are pressed against the wearer's skin by tensile forces in the elastic strands, they subject the skin to uneven distributions of pressure beneath the elastic strands, with pressure points at the inward/wearer-facing ruffles, which can promote undesirable skin marking and even skin irritation.

Substituting beamed elastic strands as the elasticizing element, of a stretch laminate used to form a front belt portion or rear belt portion of a pant, enables inclusion of a substantially greater number of finer elastic strands per unit cross-direction dimension to form a more cloth-like skin-contacting material, with dramatically smaller ruffles of substantially higher machine direction frequency and lower z-direction amplitude, than is practically available using non-beamed elastic strand technology. Use of a warp beam as a supply mechanism for supplying elastic strands to a stretch laminate manufacturing process enables this. Beamed elastic strands can be selected for this purpose to be substantially lower in decitex and lower in pre-strain, than those in a conventional stretch laminate exhibiting similar cumulative tensile, expansion and contraction characteristics, formed using conventional elastic strand technology.

In some examples, elastic material 630 may be beamed elastics incorporated into the laminate at a Manufacturing Strand Spacing no more than 2.0 mm, 1.5 mm, 1.0 mm, 0.8 mm, 0.5 mm, or even no more than 0.25 mm. The beamed elastics may be disposed within the laminate so as to result in an Average-Strand-Spacing no more than 2.0 mm, 1.5 mm, 1.0 mm, 0.8 mm, 0.5 mm, or even no more than 0.25 mm.

Beamed elastics may be formed of elastomeric material such as Spandex and similar materials disclosed herein. In order to provide a total tensile force in the laminate, suitable for providing a gasketing function while not exerting an uncomfortable amount of pressure against the wearer's skin, and also to preserve spacing between the strands to maintain breathability, the strands may be selected to have a Manufacturing Decitex and/or to result in an Average Decitex no greater than 400, more preferably no greater than 300, 200, 150, or most preferably no greater than 100.

In combination with relatively close spacing and low decitex, it may be desired to impart the beamed elastics with a Manufacturing Pre-Strain, during their incorporation into the structure, no greater than 300%, 200%, 150%, 100% or even no greater than 75%; or alternatively, to impart the strands with an amount of pre-strain that results in a laminate with an Average-Pre-Strain within these ranges.

With appropriate selection of beamed elastic strand spacing and decitex, and amount of pre-strain imparted to the strands as they are incorporated in to the cuff structure, a stretch laminate structure forming a front and/or rear belt portion of a pant and exhibiting lateral tensile forces when stretched suitable, and comparable to, those in conventional pant belt structures can provide for substantially fewer pressure points or localizations, i.e., more evenly distributed pressure against the wearer's skin, resulting in substantially reduced possibility for skin marking, and greater wearer comfort.

Figure 12:
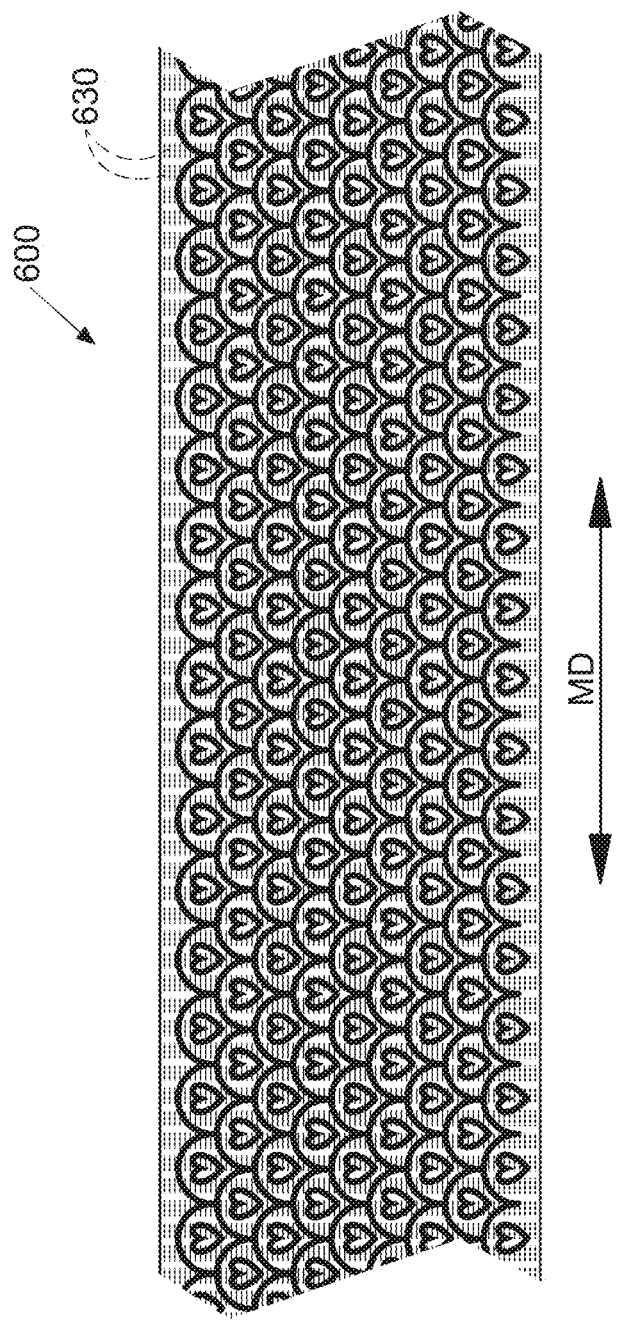
FIG. 12 is a schematic plan view of a portion of a stretch laminate with the nonwoven web material shown in FIG. 4 forming a layer component thereof, shown following manufacture but prior to elastic contraction of the elastic material therein.
Figure 13:
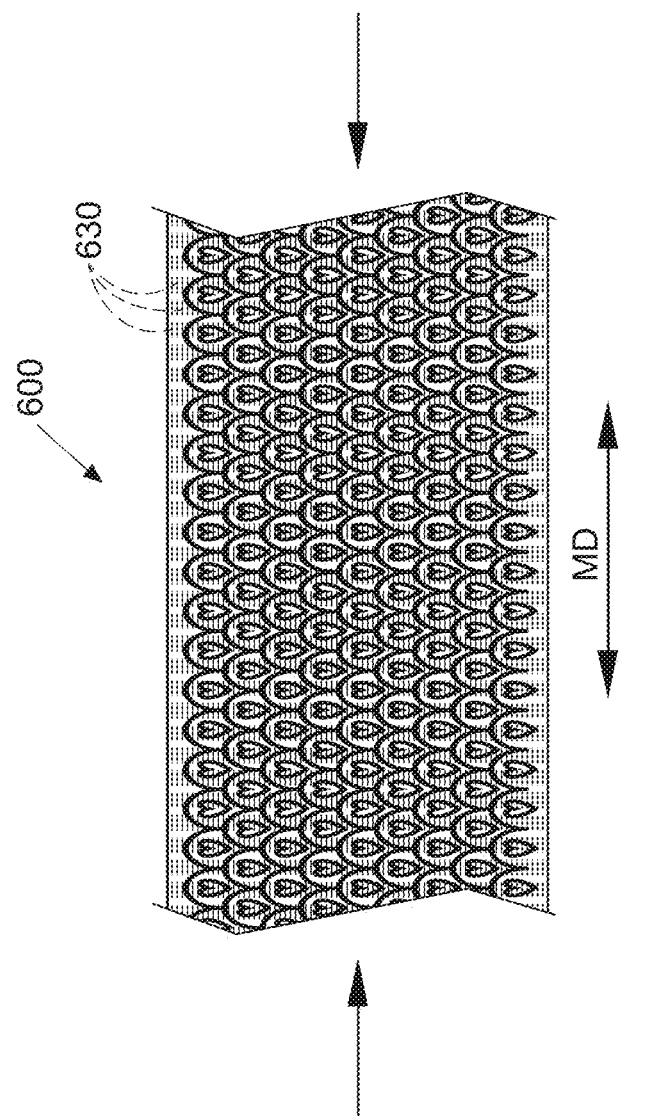
FIG. 13 is a schematic plan view of the portion of a stretch laminate shown in FIG. 11, shown following manufacture and after elastic contraction of the elastic material therein.

In addition to providing for improved appearance and wearer comfort, the relatively small, closely-spaced gathers in the sandwiching layers, made possible by use of beamed elastics, provides an improved substrate for inclusion of decorative elements. This is because decorative elements will not become substantially folded into and thereby concealed and/or visually impaired by the relatively small gathers. This makes used of beamed elastics of particular benefit for combination with a formed nonwoven web material layer with an ordered arrangement of zones embodying decorative features. Referring to FIGS. 12 and 13, an example of an ordered arrangement of zones embodying a decorative, repeating pattern of heart shapes within scallop shapes, on a formed nonwoven web material layer, is depicted. FIG. 12 depicts a portion of the laminate 600 in a stretched condition (elastic material 630 still in strained condition), as it might appear immediately following lamination. FIG. 13 depicts the same portion of the laminate in a relaxed, laterally contracted position, as it might appear following manufacture and elastic contraction of the elastic material 630. When the elastic material 630 is beamed elastics of suitably close spacing, fine decitex and low pre-strain, the gathers in the sandwiching layers including the formed nonwoven web material layer are sufficiently small and fine so as not to fold up and conceal the decorative pattern of zones. Rather, the laminate may be configured as described herein such that the pattern will remain visible, only visibly contracting laterally such that the proportions of the pattern visually change.

Figure 14:
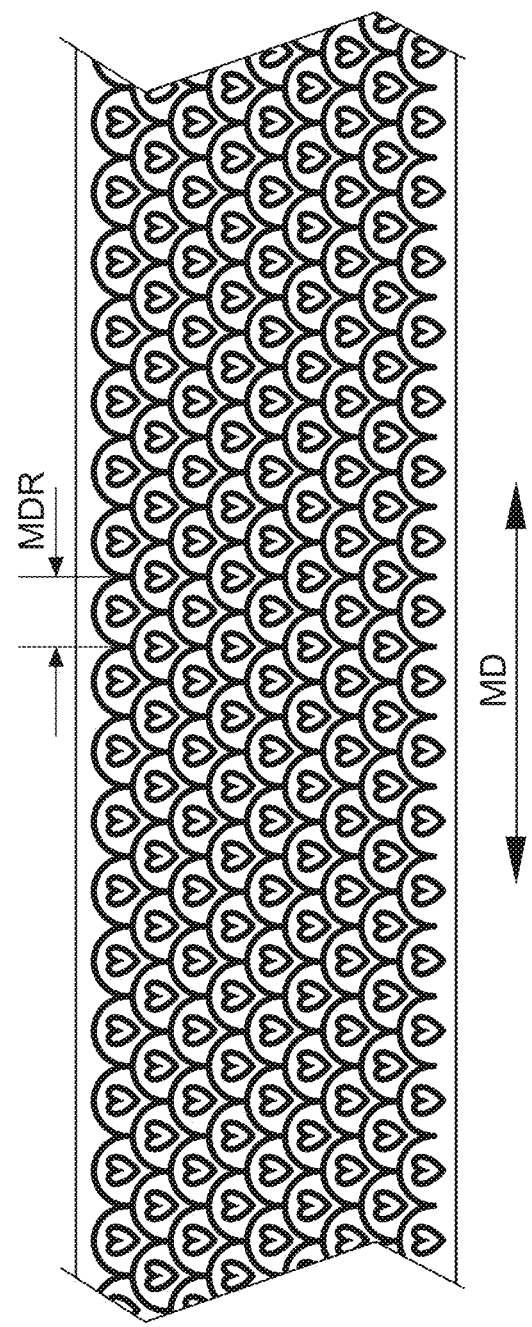
FIG. 14 is a schematic plan view of the portion of a formed nonwoven web material shown in FIG. 4, and illustrating measurement of a machine/stretch direction repeat interval in an ordered arrangement of zones.

It will be appreciated, however, that it may be desired that the ordered arrangement of zones on the formed nonwoven web material have dimensions that are large enough that they remain visible/visually discernible following such elastic contraction of the beamed elastics. Accordingly, referring to FIG. 14, in some examples, it may be desired that the pattern on the formed nonwoven web material layer (in its non-contracted condition) have a minimum repeat interval MDR in the machine direction of formation of the stretch laminate, that is sufficiently large to be not less than about 0.5 mm when the stretch laminate is relaxed and fully contracted along the machine/stretch direction of the laminate.

It may be desired that the web material(s) used to form the layers 610, 620 be selected to as to be of low enough caliper and substantial enough pliability (which affect bending stiffness) such that they can easily flex and form the comparatively fine, high-frequency, low amplitude ruffles or gathers contemplated herein, made possible by beamed elastics used to form a stretch laminate as described herein. Accordingly, it may be desired that nonwoven web materials(s) used to form one or both of layers 610, 620 have an average basis weight no greater than 30 gsm, more preferably no greater than 20 gsm, and even more preferably no greater than 15 gsm, or a combined basis weight no greater than 60 gsm, more preferably no greater than 40 gsm, and even more preferably no greater than 30 gsm. (Herein, "gsm" means grams of material per square meter. For a nonwoven web material, its basis weight is expressed in gsm. For an added material such as adhesive applied to a nonwoven web material, the quantity applied is expressed in gsm, meaning grams of added material applied per square meter of the web material.)

In some example, a first layer 610 of a stretch laminate may be formed of formed nonwoven material manufactured as described herein, with any desired ordered arrangement of build-up regions and attenuated regions imparting any desired decorative and/or functional structural features to the first layer, while a second layer 620 of the stretch laminate may be a conventional nonwoven web material that has substantially random fiber and/or filament distribution. The first layer 610 may form the outward-facing layer of, for example, a front or rear belt portion of a pant, while the second layer 620 may form the wearer-facing layer. Combined with pre-strained beamed elastics as the incorporated elasticizing mechanism as described herein, the relatively less-structured wearer-facing layer will form very fine, evenly-distributed gathers that help to evenly distribute pressure across the wearer's skin, while dramatic texture and visible structural features may be formed into the outward-facing layer. The layers may be selected and/or configured such that the outer surface of the outward-facing layer, having the formed texture, may exhibit an outer percent contact area of only from about 20 percent to about 40 percent (generally reflective of substantial texture), while the wearer-facing layer exhibits an inner percent contact area that is at least 1.25 times (1.25×), more preferably at least about 1.50 times (1.5×), even more preferably at least about 1.75 times (1.75×), and still more preferably at least about 2.0 times (2.0×) the outer percent contact area (reflective of relatively less texture and more even pressure distribution).

Nonwoven web material(s) used to form layers 610, 620 may be bonded together to form a laminate structure about beamed elastics by any suitable mechanism. In some examples, these layers may be bonded together by applying adhesive to the strand-facing surface of one or both sandwiching layers, and then bringing the layers together and compressing them about the beamed elastics, in the nip between a pair of rollers, to form a laminate structure (see, e.g. FIG. 2). Adhesive may be applied in any suitable quantity sufficient to hold the laminate structure together, but it may be desired to avoid application of adhesive to an extent that it significantly compromises elastic contractibility of the beamed elastics and of the stretch laminate structure. Accordingly, it may be desired that adhesive holding the stretch laminate structure together be applied to a basis weight of about 3 to about 15 gsm, or about 6 to about 12 gsm, or even about 7 to about 10 gsm. Adhesive may be applied to one or both of the sandwiching layers 610, 620 by any suitable method, such as by a slot coating process. The adhesive may be any adhesive formulation having elastic properties and deemed suitable for assembly of components of wearable absorbent articles, such as any hot melt adhesive known for use in the manufacture of disposable diapers and disposable absorbent pants.

Alternatively, or in addition, the material forming layers 610, 620 may be bonded together to form a laminate structure about beamed elastics by a pattern of mechanical bonds. Herein, "mechanical bonds" are bonds formed by application of pressure with or without heat or heating energy applied, in which bonds are formed between the material layers by deformation and in some examples fusing of components of the respective layers together. In some examples, the material(s) forming layers 610, 620 may be bonded together to form a laminate structure by methods described in U.S. application Ser. No. 15/832,929 or U.S. application Ser. No. 15/833,057. Referring to FIG. 2, laminating rolls 60a, 60b may be a pair of calender bonding rollers, wherein at least one of the rolls, a bonding roller, bears on its cylindrical surface a plurality of radially-projecting bonding protrusions, arranged in any desired pattern, and the other roll has a smooth cylindrical surface and thereby constitutes an anvil roller. The pattern of bonding protrusions on the bonding roller exert localized pressure on the laminate components, where the bonding protrusions approach the anvil roller in the nip 60c. In conjunction therewith, one or both rolls 60a, 60b may be heated. The combination of localized pressure and heat may be used to fuse the material(s) forming the filaments of the layers 610, 620 together in a pattern of mechanical bonds corresponding to the pattern of bonding protrusions on the calender roller.

In some examples, a sonotrode may be substituted for an anvil roller, to transmit ultrasonic vibratory energy to heat the filaments beneath the bonding protrusions in the nip, and effect fusing via ultrasonic energy as a substitute for direct heat. Various methods for bonding a stretch laminate are also described in the co-pending application filed on the same date of filing of the present application, with named inventors LaVon et al., Procter & Gamble 62/686,896, entitled "BEAMED ELASTOMERIC LAMINATE STRUCTURE AND TEXTURE."

When one or both sandwiching layers 610, 620 of a stretch laminate material are formed of a formed nonwoven web material as described herein, in some circumstances it may be preferred that the laminate be assembled and laminated via use of adhesive. Use of adhesive rather than a pattern of mechanical bonds may be preferred to bond a laminate as contemplated herein, for several reasons. One reason may be that attempts to form an even pattern of mechanical bonds between layers may be difficult when a substantial number of the bond protrusions on the calendar bonding roller will encounter attenuated regions 272 within an ordered arrangement of zones 160, in a formed nonwoven web layer. Filament material in an attenuated region of a formed nonwoven web material may be insufficient in quantity to create a robust bond between respective layers 610, 620 about the elastic strands, resulting in either no bond, or only a very fragile, weak bond likely to fail upon exposure to minimal stress, risking creation of a ragged hole in the formed nonwoven web material layer where the individual bond was intended. A second reason, particular to use of beamed elastics as the elastic material 630, may be that a mechanical bonding process and intended pattern of bonding may in some circumstances be likely to sever or otherwise severely deform and weaken a substantial number of individual strands within the array of beamed elastics. The resulting stretch laminate may be unable to withstand substantial strain without failure of a substantial number of severed or damaged strands, resulting in substantial lessening of the ability of the stretch laminate to contract toward the unstrained lengths of the beamed elastics.

Accordingly, in some circumstances it may be preferred that adhesive be the mechanism by which a stretch laminate including beamed elastics and a formed nonwoven web material layer is held together. Such circumstances may include circumstances in which most or all of the surface area of the formed nonwoven layer is occupied by zones within the ordered arrangement, or where the attenuated regions of the zones are closely spaced relative the spacing of the bonding pattern.

In other examples, however, a pattern of mechanical bonds may be deemed suitable for bonding the layers 610, 620 about the elastic material. Such circumstances may include situations where, for example, a relatively large proportion of the surface area of the formed nonwoven layer is unoccupied by attenuated regions in the ordered arrangement and/or where the attenuated regions are widely spaced, relative the pattern, sizes and spacing of the mechanical bonds in the bonding pattern. In these circumstances, substantial defects in the laminate such as those described above may be less likely, or may be less likely to be substantially numerous.

This disclosure also contemplates hybrid configurations, i.e., wherein both a pattern of mechanical bonds, e.g., ultrasonic bonds, and an application of adhesive (which also may be patterned), are used to bond the laminate in differing areas thereof. Referring to FIGS. 2, 3, 11, 16 and 17, for example, it may be desired to configure the process equipment to apply adhesive to portions of the layers 610, 620 and/or the elastic material 630 components to effect adhesive bonding in areas 710 occupied by zones 160 of the ordered arrangement on a formed material layer, and to effect mechanical bonding between layers 610, 620 in areas of the stretch laminate corresponding/subjacent to areas 720 of the formed nonwoven material unoccupied by zones 160 of the ordered arrangement. The pattern of mechanical bonds may be designed (via design of the calender bonding roller) to effect any desired placement and pattern, and may have bonds that are relatively widely spaced to, e.g., impart a quilt-like appearance to the stretch laminate, where no adhesive is applied to bond the formed nonwoven web layer and prevent it from billowing out in the z-direction between bonds, when the stretch laminate is contracted.

Further, in some circumstances an adhesive may impair the elastic contractibility of relatively fine decitex beamed elastics. The impairment is simply the result of physical obstruction, by the adhesive, of the fine elastic strands. Accordingly, bonding without adhesive may help to better preserve contractibility. Ultrasonic bonding in a pattern and depth as described in the co-pending application filed on the same date of filing of the present application, with named inventors LaVon et al., Procter & Gamble 62/686,896, entitled "BEAMED ELASTOMERIC LAMINATE STRUCTURE AND TEXTURE," may be particularly useful for preserving elastic contractibility of beamed elastics in a stretch laminate.

In the examples depicted in FIGS. 16 and 17, as noted, mechanical bonding rather than adhesive bonding may be used to bond layers 610, 620 about elastic material 630, in unoccupied areas 720 of the formed nonwoven web material layer. For reasons explained above, this configuration may provide for relatively better elastic contractibility along a generally lateral direction, along selected areas. In the example depicted in FIG. 16, mechanical bonding rather than adhesive bonding may be provided in areas 720 along waist opening edge 114a and leg opening edges 114b, to provide for relatively better elastic contractibility along these areas, forming a waistband-like structure and legband-like structures differentiated by such relatively better contractibility. In the example depicted in FIG. 17, mechanical bonding rather than adhesive bonding may be provided in area 720 along a belly curve, to provide for relatively better elastic contractibility thereabout, forming a contouring body-hugging structure, differentiated by such relatively better contractibility. As suggested in the figures, a region of the stretch laminate corresponding with an unoccupied region 720 of the formed nonwoven web material layer, and bonded with a pattern of mechanical bonds rather than adhesive, may extend along a majority or all of the lateral width of a front or rear belt portion of a pant.

Referring to FIG. 2, a plurality of beamed elastics 630b (from about 10 strands to about 1500 strands having a decitex from about 10 to about 500) may be unwound from a beam 51b (which is a first metering device 52) in the machine direction MD and transferred from the beam 51b to a second metering device 53 (which includes a first roller 60a and a second roller 60b, which form a nip 60c). The plurality of beamed elastics 630b may be stretched along the machine direction MD between the first metering device 52 and the second metering device 53 to pre-strain the elastics (from about 50% to about 400%). The stretched elastic strands 630b may be joined via an adhesive 62 from an adhesive applicator 61 with a first layer 610 and a second layer 620 at the second metering device 53 to produce an elasticized stretch laminate 600, such that each of the beamed elastic strands are spaced (in the cross direction) in the laminate from about 0.25 mm to about 5 mm (center-to-center). It is this laminate 600 that may be further incorporated into a wearable absorbent article or component thereof, to offer the benefits described herein. Further details of the process of creating beamed elastic laminate(s) for use in disposable absorbent articles are disclosed in U.S. App. Ser. No. 62/436,589, filed on Dec. 20, 2016. The laminate 600 may be produced as part of the absorbent article manufacturing line, or may be produced offline, and unwound as an elastic laminate that is fed into the absorbent article manufacturing line.

A stretch laminate may be manufactured using a plurality of beams 51b configured to deliver beamed elastics having the same or differing decitex, spacing, elastomer composition and/or pre-strain level in parallel (side-by-side), to create a stretch laminate having bands of differing lateral stretch and/or tensile force characteristics.

Beamed Elastic Strand Composition (Spandex vs. Extruded Strands)

Beamed elastic may comprise spandex fibers. One type of spandex fiber is "polyurethane urea" elastomer or the "high hard segment level polyurethane" elastomer, which must be formed into fibers using a solution (solvent) spinning process (as opposed to being processable in the molten state.) The urea linkages in polyurethane urea provides strong mutual chemical interactions crucial for providing "anchoring" that enables good stress relaxation performance at temperatures near body temperature on timescales corresponding to diaper wear, including overnight. This type of anchoring enables better force relaxation (i.e. little force decay with time when held in stretched condition at body temperature) over many thermoplastic polyurethane (polyurethane with hard segment melting below 200 deg. C.) or thermoplastic styrenic block copolymers.

In contrast, extruded strands and scrims are typically made of styrenic block copolymers or thermoplastic elastomers that can be formed in the molten state by conventional extrusion processes. Thermoplastic elastomers include compositions like polyolefin, polyurethane (polyurethane with hard segment melting below 200 deg. C.) elastomers, etc. Because these thermoplastic elastomers like Polyurethane (polyurethane with hard segment melting below 200 deg. C.) can be melted/re-melted, and extruded it makes them susceptible to higher stress relaxation in use, which is a major negative. The styrenic block copolymers used in extruded strands include a comparatively long rubbery midblock situated between comparatively short end blocks. End blocks sufficiently short to enable good flow conventional extrusion processes often have a greater propensity to stress relax and undergo force relaxation over time.

The urea linkage present in spandex requires it to be made by spinning process. Spandex cannot be melted/re-melted or extruded like styrenic block copolymers. Spandex pre-polymer is combined with solvent and additives, and the solution is spun to make solid spandex fiber. Multiple fibers are then formed together to make one spandex strand. The spandex strands may have surface finish to avoid blocking and wound onto spools. The one spandex fiber may have a decitex of about 15, so a 500 decitex strand may have nominally 33 fibers wound together to make one strand. Depending on the decitex we use for beam approach, we may have 15 fibers (or filaments), 8 fibers, 5 fibers, 3 fibers or even as low as 2 fibers. Spandex fiber can be mono-component or bi-component (as disclosed in WO201045637A2).

Further related to the chemistry of beamed elastics, it may be desirable to coat the beamed elastics with an oil, such as a silicone oil, mineral oil or the like, including about 10%, about 7%, about 5%, about 3%, or about 1% of such oil. Treating the beamed elastics with such an oil helps to prevent blocking (cross-linking) when the strands are wound to a spool or a beam and it also lowers the coefficient of friction of the strand, which may be desirable in some circumstances in connection with movement of the strands through processing equipment.

Commercially available spandex strands may also be known as LYCRA (a product of INVISTA, Wichita, KS), CREORA (a product of Hyosung, Seoul, Korea), or DORLASTAN (a product of Asahi Kasei Corporation, Tokyo, Japan). Spandex is often referred as Elastane fiber or Polyurethane fiber.

EXAMPLES

Consumer interactions and research have shown that a longstanding unmet consumer need exists to provide absorbent articles which have the right balance of modulus for application and removal ease and freedom of movement while providing an article with low elastic pressure (relative to today's stranded products) to provide a comfortable wearing experience free from skin marks. It has been found that elastic laminate structures having a Section-Modulus of between about 2 gf/mm and 15 gf/mm, alternatively from about 4 gf/mm to about 10 gf/mm, are most desirable for ease of application, ease of removal, conforming fit and freedom of movement. Depending on the elastic configuration in these structures they may exhibit very high Pressure-Under-Strand, e.g., elastic strands, leading to increased skin marking and reduced comfort. One approach to reduce the pressure of the elastic on the skin is to increase the number of elastics for a given area. Increasing the number of elastics within a given area alone may reduce the Pressure-Under-Strand, however, if that is the only change it can also significantly increase the overall modulus of the elastic laminate structure. In order to achieve the right balance of modulus and pressure on the skin it is necessary to reduce the elastic decitex and/or the elastic strain as the spacing between the elastics is reduced thereby increasing the elastic number in order to balance the modulus and pressure on the skin and maintain these parameters within the consumer preferred range. This breakthrough has been enabled through delivery of very low decitex elastic at very low strain levels and with very tight elastic spacing that have never before been seen in disposable absorbent articles. Delivery of such low decitex elastic at low strain and tight spacing is enabled via a new to absorbent article technology created from the textile warp beam technology approach. The examples below are some embodiments of such elastomeric structures.

TABLE 1

Inventive Belt Elastic Profiles

| Section | Number of Elastics | Average-Dtex | Average-Pre-Strain | Average-Strand-Spacing (mm) | Open Area (%) | Section-Modulus (gf/mm) | Pressure-Under-Strand (psi) |
|---|---|---|---|---|---|---|---|
| A Front Belt | | | | | | | |
| 1 | 40 | 140 | 100% | 0.6 | 79.2% | 10.9 | 0.328 |
| 2 | 40 | 70 | 150% | 0.6 | 85.3% | 5.5 | 0.463 |
| 3 | 40 | 70 | 150% | 0.6 | 85.3% | 5.5 | 0.463 |
| 4 | 40 | 140 | 100% | 0.6 | 79.2% | 10.9 | 0.328 |
| Back Belt | | | | | | | |
| 4 | 40 | 140 | 100% | 0.6 | 79.2% | 10.9 | 0.328 |
| 3 | 40 | 70 | 150% | 0.6 | 85.3% | 5.5 | 0.463 |
| 2 | 40 | 70 | 150% | 0.6 | 85.3% | 5.5 | 0.463 |
| 1 | 40 | 140 | 100% | 0.6 | 79.2% | 10.9 | 0.328 |
| B Front Belt | | | | | | | |
| 1 | 50 | 70 | 175% | 0.5 | 82.4% | 6.6 | 0.386 |
| 2 | 50 | 70 | 175% | 0.5 | 82.4% | 6.6 | 0.386 |
| 3 | 50 | 70 | 175% | 0.5 | 82.4% | 6.6 | 0.386 |
| 4 | 50 | 70 | 175% | 0.5 | 82.4% | 6.6 | 0.386 |
| Back Belt | | | | | | | |
| 4 | 50 | 70 | 175% | 0.5 | 82.4% | 6.6 | 0.386 |
| 3 | 50 | 70 | 175% | 0.5 | 82.4% | 6.6 | 0.386 |
| 2 | 50 | 70 | 175% | 0.5 | 82.4% | 6.6 | 0.386 |
| 1 | 50 | 70 | 175% | 0.5 | 82.4% | 6.6 | 0.386 |
| C Front Belt | | | | | | | |
| 1 | 30 | 70 | 200% | 0.8 | 89.0% | 4.1 | 0.618 |
| 2 | 20 | 210 | 150% | 1.1 | 86.1% | 8.9 | 0.490 |
| 3 | 30 | 70 | 200% | 0.8 | 89.0% | 4.1 | 0.618 |
| 4 | 30 | 70 | 200% | 0.8 | 89.0% | 4.1 | 0.618 |

TABLE 1-continued

Inventive Belt Elastic Profiles

| Section | Number of Elastics | Average-Dtex | Average-Pre-Strain | Average-Strand-Spacing (mm) | Open Area (%) | Section-Modulus (gf/mm) | Pressure-Under-Strand (psi) |
|---|---|---|---|---|---|---|---|
| Back Belt | | | | | | | |
| 4 | 30 | 70 | 200% | 0.8 | 89.0% | 4.1 | 0.618 |
| 3 | 30 | 70 | 200% | 0.8 | 89.0% | 4.1 | 0.618 |
| 2 | 30 | 70 | 200% | 0.8 | 89.0% | 4.1 | 0.618 |
| 1 | 30 | 210 | 150% | 1.1 | 86.1% | 8.9 | 0.490 |

Example—Belt-Type Pant

Example 1 is a belted pant absorbent article. The pant includes a belt laminate disposed in both front and rear waist regions and the following materials and construction.
Outer belt layer: 13 gsm spunbond nonwoven
Inner belt layer: 13 gsm spunbond nonwoven
Backsheet film: 12 gsm liquid impermeable polyethylene film
Core Wrap: 10 gsm hydrophilic spunbond nonwoven
AGM: absorbent gelling material
Distribution Layer: crosslinked cellulosic fiber
Acquisition Layer: 43 gsm synthetic acquisition layer
Topsheet: 12 gsm hydrophilic spunbond nonwoven
Belt Elastic Profile: Table 1, col B It may be desirable for the elastomeric laminate of the present invention to have a Pressure-Under-Strand of from about 0.1 psi to about 1.0 psi. In certain embodiments, the Pressure-Under-Strand may be from about 0.2 to about 0.8 psi.

Test and Measurement Methods
General Sample Preparation

The General Sample Preparation is intended to be used for methods that do not have specific sample preparation instructions within the method itself.

When collecting a specimen for testing, the specimen must contain a plurality of elastic strands and/or an elastic material; film, elastic scrim, elastic foam, elastic ribbons, elastic strips, etc. In situations where the elastic material and/or elastic strands is not fully secured within the sample, the test specimen must be obtained in a way that elastic material and/or elastic strands within the test region of the specimen are as they were intended and not altered as a result of collection of the specimen. If the elastic material or any elastic strands release, creep or become separated within or from the laminate, the specimen is discarded and a new specimen prepared.

For pants, remove the side panels where they are attached to the chassis and separate the side panels at the side seams. Identify the elastic material that transverses the entire width

TABLE 2

Performance Characteristics of Existing and Inventive Belt Sections

| Example Belt Sections | Average-Dtex | Average-Strand-Spacing (mm) | Open Area (%) | Section-Modulus (gf/mm) | Pressure-Under-Strand (psi) |
|---|---|---|---|---|---|
| Pampers Easy Ups Training Underwear for Boys size 4T-5T (example section 1 of 4) | 1100 | 9.0 | 96.1% | 5.7 | 1.753 |
| Pampers Easy Ups Training Underwear for Boys size 4T-5T (example section 2 of 4) | 940 | 9.0 | 96.4% | 7.3 | 1.897 |
| Pampers Easy Ups Training Underwear for Boys size 4T-5T (example section 3 of 4) | 680 | 9.0 | 97.0% | 3.5 | 2.230 |
| Always Discreet Underwear Maximum Classic Cut size S/M (example section 1 of 4) | 800 | 7.0 | 95.7% | 5.4 | 1.599 |
| Always Discreet Underwear Maximum Classic Cut size S/M (example section 2 of 4) | 680 | 7.0 | 96.1% | 4.6 | 1.734 |
| Always Discreet Boutique Maximum Protection size S/M (example section 1 of 4) | 470 | 4.0 | 94.3% | 5.5 | 1.192 |
| Always Discreet Boutique Maximum Protection size S/M (example section 2 of 4) | 680 | 4.0 | 93.1% | 8.0 | 0.991 |
| Inventive Example (example section 1 of 4) | 160 | 0.5 | 73.4% | 15.0 | 0.255 |
| Inventive Example (example section 2 of 4) | 140 | 0.5 | 75.1% | 13.1 | 0.273 |
| Inventive Example (example section 3 of 4) | 250 | 0.8 | 79.2% | 14.6 | 0.327 | of the panel. Identify the longitudinally distal most edge of the elastic material or elastic strand (closest to the waist edge) and the longitudinally proximal most edge of the elastic material or elastic strand (closest to the leg edge) determine the midpoint between the distal most elastic strand or elastic material edge and the proximal most elastic strand or elastic material edge. Cut a 40 mm wide strip laterally across the entire panel centered at the midpoint. Repeat for each front and rear side panel that contains elastic material and/or elastic strands.

For taped diapers, remove ear panels where they are attached to the chassis. Identify the elastic material that transverses the entire width of the panel. Identify the distal most elastic material edge or elastic strand (closest to the waist edge) and the proximal most elastic material edge or elastic strand (closest to the leg edge) determine the midpoint between the distal most elastic strand or elastic material edge and the proximal most elastic strand or elastic material edge. Cut a 40 mm wide strip laterally across the entire ear panel centered at the midpoint. Repeat for each front and rear ear panel that contains elastic material and/or elastic strands.

For a belted article, mark the product on the front and back by extending a line from along the side of the core to the waist edge. Remove the belt from the article, using an appropriate means (e.g. freeze spray), taking care not to delaminate the belt or release the elastics. Separate the front belt from the back belt along any seams. Identify the distal most elastic material edge or elastic strand (closest to the waist edge) and the proximal most elastic material edge or strand (closest to the leg edge) determine the midpoint between the distal most elastic strand or elastic material edge and the proximal most elastic strand or elastic material edge. Cut a 40 mm wide strip parallel to the waist edge if linear or to the elastic strands if linear and centered at the midpoint, across the entire belt portion. If the strip has a region that does not contain elastic strands or elastic material (e.g., a portion that overlapped the core, etc.) cut along the ends of the elastic strands/elastic material, to remove the non-elastic region and treat as two specimens.

For waistbands, they are tested as a single piece of material. Remove the belt from the article, using an appropriate means (e.g. freeze spray), taking care not to delaminate the belt or release the elastics.

For the leg cuffs, each of the leg cuffs is tested as a single piece of material. The inner leg cuff sample is considered to be the portion of the inner leg cuff that extends from the proximal most edge of the inner leg cuff to and including the distal most elastic of the inner leg cuff and extending longitudinally to the front and back waist edges of the chassis. The outer leg cuff sample is considered to be the portion of the outer leg cuff that extends from the distal most edge of the outer leg cuff to and including the proximal most elastic of the outer leg cuff and extending longitudinally to the front and back waist edges of the chassis.

For all specimen strips calculate a Span Corrected Width (SCW) is calculated as:

$$\text{Span Corrected Width} = d\left(\frac{n}{n-1}\right)$$

where d is the distance (mm) between the two distal strands, and n is the number of strands, when n>1. Clamp the strip at each end and measure the length between the clamps to the nearest 1 mm. Apply a weight equal to 3 g/mm SCW. After 10 seconds measure the final weight to the nearest 1 mm. Calculate the elongation as (Final Length−Initial Length)/Initial length.

Average-Strand-Spacing

Using a ruler calibrated against a certified NIST ruler and accurate to 0.5 mm, measure the distance between the two distal strands within a section to the nearest 0.5 mm, and then divide by the number of strands in that section−1

$$\text{Average-Strand-Spacing} = d/(n-1) \text{ where } n>1$$

report to the nearest 0.1 mm.

Average Decitex (Average-Dtex)

The Average Decitex Method is used to calculate the Average-Dtex on a length-weighted basis for elastic strands present in an entire article, or in a specimen of interest extracted from an article. The decitex value is the mass in grams of a strand present in 10,000 meters of that material in the relaxed state. The decitex value of elastic strands or elastic laminates containing elastic strands is often reported by manufacturers as part of a specification for an elastic strand or an elastic laminate including elastic strands. The Average-Dtex is to be calculated from these specifications if available. Alternatively, if these specified values are not known, the decitex value of an individual elastic strand is measured by determining the cross-sectional area of a strand in a relaxed state via a suitable microscopy technique such as scanning electron microscopy (SEM), determining the composition of the strand via Fourier Transform Infrared (FT-IR) spectroscopy, and then using a literature value for density of the composition to calculate the mass in grams of the strand present in 10,000 meters of the strand. The manufacturer-provided or experimentally measured decitex values for the individual elastic strands removed from an entire article, or specimen extracted from an article, are used in the expression below in which the length-weighted average of decitex value among elastic strands present is determined.

The lengths of elastic strands present in an article or specimen extracted from an article is calculated from overall dimensions of and the elastic strand pre-strain ratio associated with components of the article with these or the specimen, respectively, if known. Alternatively, dimensions and/or elastic strand pre-strain ratios are not known, an absorbent article or specimen extracted from an absorbent article is disassembled and all elastic strands are removed. This disassembly can be done, for example, with gentle heating to soften adhesives, with a cryogenic spray (e.g. Quick-Freeze, Miller-Stephenson Company, Danbury, CT), or with an appropriate solvent that will remove adhesive but not swell, alter, or destroy elastic strands. The length of each elastic strand in its relaxed state is measured and recorded in millimeters (mm) to the nearest mm.

Calculation of Average-Dtex

For each of the individual elastic strands $f_i$ of relaxed length $L_i$ and strand decitex value $d_i$ (obtained either from the manufacturer's specifications or measured experimentally) present in an absorbent article, or specimen extracted from an absorbent article, the Average-Dtex for that absorbent article or specimen extracted from an absorbent article is defined as:

$$\text{Average-}Dtex = \frac{\sum_{i=1}^{n}(L_i \times d_i)}{\sum_{i=1}^{n} L_i}$$

where n is the total number of elastic strands present in an absorbent article or specimen extracted from an absorbent article. The Average-Dtex is reported to the nearest integer value of decitex (grams per 10 000 m).

If the decitex value of any individual strand is not known from specifications, it is experimentally determined as described below, and the resulting strand decitex value(s) are used in the above equation to determine Average-Dtex.

Experimental Determination of Decitex Value for a Strand

For each of the elastic strands removed from an absorbent article or specimen extracted from an absorbent article according to the procedure described above, the length of each elastic strand $L_k$ in its relaxed state is measured and recorded in millimeters (mm) to the nearest mm. Each elastic strand is analyzed via FT-IR spectroscopy to determine its composition, and its density $\rho_k$ is determined from available literature values. Finally, each strand is analyzed via SEM. The strand is cut in three approximately equal locations perpendicularly along its length with a sharp blade to create a clean cross-section for SEM analysis. Three strand segments with these cross sections exposed are mounted on an SEM sample holder in a relaxed state, sputter coated with gold, introduced into an SEM for analysis, and imaged at a resolution sufficient to clearly elucidate strand cross sections. Strand cross sections are oriented as perpendicular as possible to the detector to minimize any oblique distortion in the measured cross sections. Strand cross sections may vary in shape, and some strands may consist of a plurality of individual filaments. Regardless, the area of each of the three strand cross sections is determined (for example, using diameters for round strands, major and minor axes for elliptical strands, and image analysis for more complicated shapes), and the average of the three areas $a_k$ for the elastic strand, in units of micrometers squared ($\mu m^2$), is recorded to the nearest 0.1 $\mu m^2$. The decitex $d_k$ of the kth elastic strand measured is calculated by:

$$d_k = 10\ 000\ m \times a_k \times \rho_k \times 10^{-6}$$

where $d_k$ is in units of grams (per calculated 10,000 meter length), $a_k$ is in units of $\mu m^2$, and $\rho_k$ is in units of grams per cubic centimeter (g/cm$^3$). For any elastic strand analyzed, the experimentally determined $L_k$ and $d_k$ values are subsequently used in the expression above for Average-Dtex.

Surface Topography (Percent Contact Area, Rugosity Frequency, Rugosity Wavelength and 2-98% Height Value)

In the Surface Topography Method, an elastic laminate specimen is removed from an absorbent article and extended across and in contact with the convex surface of a transparent horizontal cylindrical tubing segment, allowing the areal surface topology of the wearer-facing side of the laminate to be measured through the transparent tubing segment using optical profilometry. The 3D surface data are then sampled and processed to extract several parameters that describe the percent contact area and height of the elastic laminate specimen surface as well as the frequency and wavelength of its associated rugosities. All sample preparation and testing is performed in a conditioned room maintained at about 23±2° C. and about 50±2% relative humidity, and samples are equilibrated in this environment for at least 24 hours prior to testing.

Sample Preparation

Each elastic laminate specimen extracted from an article is mounted on a horizontal tubing segment as described below. The tubing segment is cut from a sufficient length of optically clear, colorless cast acrylic cylindrical tubing having an outer diameter of 8.0 inches (203 mm) and a wall thickness of 0.1875 inches (4.76 mm). The segment has a dimension of 4.0 inches (102 mm) along an axis parallel to the central cylindrical axis of the parent tubing and a circumferential outer arc length of 5.5 inches (140 mm).

The elastic laminate specimen is extended in its primary stretch direction to a ratio corresponding to its extension at 3 g/mm (mass per linear width), where its width is determined by the Span Corrected Width metric as defined in the Caliper Test Method, and in which the extension is the average ratio measured under static load for the first ten seconds during which it is applied. In this extended state, the extended elastic laminate specimen is oriented such that its wearer-facing surface is in contact with the convex surface of the tubing segment and that the axis of extension is oriented around the circumference of the tubing segment. The extended laminate is secured at both ends to the transparent tubing segment such that the wearer-facing surface of the laminate is viewable through the concave side of the transparent tubing segment.

Five replicate elastic laminate specimens are isolated and prepared in this way from five equivalent absorbent articles for analysis.

3D Surface Image Acquisition

A three-dimensional (3D) surface topography image of the wearer-facing surface of the extended elastic laminate specimen is obtained using a DLP-based, structured-light 3D surface topography measurement system (a suitable surface topography measurement system is the MikroCAD Premium instrument commercially available from LMI Technologies Inc., Vancouver, Canada, or equivalent). The system includes the following main components: a) a Digital Light Processing (DLP) projector with direct digital controlled micro-mirrors; b) a CCD camera with at least a 1600×1200 pixel resolution; c) projection optics adapted to a measuring area of at least 60 mm×45 mm; d) recording optics adapted to a measuring area of 60 mm×45 mm; e) a table tripod based on a small hard stone plate; f) a blue LED light source; g) a measuring, control, and evaluation computer running surface texture analysis software (a suitable software is MikroCAD software with Mountains Map technology, or equivalent); and h) calibration plates for lateral (XY) and vertical (Z) calibration available from the vendor.

The optical 3D surface topography measurement system measures the surface height of a sample using the digital micro-mirror pattern fringe projection technique. The nature of this pattern projection technique allows the surface topography of a specimen to be interrogated through a transparent material. The result of the measurement is a 3D data set of surface height (defined as the Z-axis) versus displacement in the horizontal (X-Y) plane. This 3D data set can also be thought of as an image in which every pixel in the image there is associated an X-Y displacement, and the value of the pixel is the recorded Z-axis height value. The system has a field of view of 60×45 mm with an X-Y pixel resolution of approximately 37 microns, and a height resolution of 0.5 microns, with a total possible height range of 32 mm.

The instrument is calibrated according to manufacturer's specifications using the calibration plates for lateral (X-Y plane) and vertical (Z-axis) available from the vendor.

The elastic laminate specimen mounted on the transparent tubing segment is positioned with the concave surface of the tubing segment surface facing upward so that the wearer-facing surface is facing upward and visible through the transparent material. The tubing segment is placed on a stand such that the convex (downward-facing) specimen surface in the region to be analyzed is suspended freely and not resting on a surface. The tubing segment is oriented such that its circumferential direction (that direction or axis along which the laminate is stretched) is centered and perpendicular relative to the long axis of the camera's field of view (or either of the central axes if the field of view is square). A 3D surface topology image of the elastic laminate specimen is collected by following the instrument manufacturer's recommended measurement procedures, which may include focusing the measurement system and performing a brightness adjustment. No pre-filtering options are used. The collected height image file is saved to the evaluation computer running the surface texture analysis software.

If the field of view of the 3D surface topography measurement system exceeds the evaluation region on the elastic laminate specimen the image may be cropped to remove extraneous areas and retain a rectangular field of view of the relevant portion, while maintaining the X-Y resolution, prior to performing the analysis.

3D Surface Image Analysis

The 3D surface topography image is opened in the surface texture analysis software. The following filtering procedure is then performed on each image: 1) removal of invalid or non-measured points; 2) a 5×5 pixel median filter to remove noise; 3) a 5×5 pixel mean filter to smooth the surface; and 4) subtraction of a two-dimensional, second-order polynomial (determined via least-squares fit of the surface topology image) to remove the general form and flatten the surface. The second-order polynomial is defined by the following equation:

$$f(x,y)=c_1+c_2x+c_3y+c_4x^2+c_5y^2+c_6xy$$

Each data set that has been processed to this point as described above is referred to as a "preprocessed specimen data set." The highest points of the resulting topology image correspond to those areas in contact with the convex surface of the tubing segment, and the lowest points are those points most distal below the convex surface of the tubing segment.

Contact Surface Areas and 2-98% Height

For each of the 3D surface topography images of the five replicate specimens, the following analysis is performed on preprocessed specimen data sets. The Percent Surface Contact Area and 2-98% Height measurements are derived from the Areal Material Ratio (Abbott-Firestone) curve described in the ISO 13565-2:1996 standard extrapolated to surfaces. This curve is the cumulative curve of the surface height distribution histogram versus the range of surface heights measured. A material ratio is the ratio, expressed as a percent, of the area corresponding to points with heights equal to or above an intersecting plane passing through the surface at a given height, or cut depth, to the cross-sectional area of the evaluation region (field of view area). The height at a material ratio of 2% is initially identified. A cut depth of 100 μm below this height is then identified, and the material ratio at this depth is recorded as the Percent Surface Contact Area at 100 p.m. This procedure is repeated at a cut depth of 200 μm and 300 μm below the identified height at a material ratio of 2%, and the material ratio at these depths are recorded as the Percent Surface Contact Area at 200 μm and the Percent Surface Contact Area at 300 μm respectively. All of the Percent Contact Area values are recorded to the nearest 0.1%.

The 2-98% Height of the specimen surface is defined as the difference in heights between two material ratios that exclude a small percentage of the highest peaks and lowest valleys. The 2-98% Height of the specimen surface is the height between the two cutting depths corresponding to a material ratio value of 2% to the material ratio of 98%, and is recorded to the nearest 0.01 mm.

Reporting of Method Parameters

After the 3D surface image analysis described above is performed on 3D surface topology images of all five specimen replicates, the following output parameters are defined and reported. The arithmetic mean of all five Percent Surface Contact Area at 100 μm measurements is defined as the Average Percent Surface Contact Area at 100 μm and is reported to the nearest 0.1%. The arithmetic mean of all five Percent Surface Contact Area at 200 μm measurements is defined as the Average Percent Surface Contact Area at 200 μm and is reported to the nearest 0.1%. The arithmetic mean of all five Percent Surface Contact Area at 300 μm measurements is defined as the Average Percent Surface Contact Area at 300 μm and is reported to the nearest 0.1%. The arithmetic mean of all five 2-98% Height measurements is defined as the Average 2-98% Height and is reported in units of mm to the nearest 0.01 mm. The arithmetic mean of all five Rugosity Frequency measurements is defined as the Average Rugosity Frequency and is reported in units of mm to the nearest 0.001 $mm^{-1}$. The arithmetic mean of all five Rugosity Wavelength measurements is defined as the Average Rugosity Wavelength and is reported in units of mm to the nearest 0.01 mm.

Average-Pre-Strain

The Average-Pre-Strain of a specimen are measured on a constant rate of extension tensile tester (a suitable instrument is the MTS Insight using Testworks 4.0 Software, as available from MTS Systems Corp., Eden Prairie, MN) using a load cell for which the forces measured are within 1% to 90% of the limit of the cell. Articles are conditioned at 23° C.±2° C. and 50%±2% relative humidity for 2 hours prior to analysis and then tested under the same environmental conditions.

Program the tensile tester to perform an elongation to break after an initial gage length adjustment. First raise the cross head at 10 mm/min up to a force of 0.05N. Set the current gage to the adjusted gage length. Raise the crosshead at a rate of 100 mm/min until the specimen breaks (force drops 20% after maximum peak force). Return the cross head to its original position. Force and extension data is acquired at a rate of 100 Hz throughout the experiment.

Set the nominal gage length to 40 mm using a calibrated caliper block and zero the crosshead. Insert the specimen into the upper grip such that the middle of the test strip is positioned 20 mm below the grip. The specimen may be folded perpendicular to the pull axis, and placed in the grip to achieve this position. After the grip is closed the excess material can be trimmed. Insert the specimen into the lower grips and close. Once again, the strip can be folded, and then trimmed after the grip is closed. Zero the load cell. The specimen should have a minimal slack but less than 0.05 N of force on the load cell. Start the test program.

From the data construct a Force (N) verses Extension (mm). The Average-Pre-Strain is calculated from the bend in the curve corresponding to the extension at which the nonwovens in the elastic are engaged. Plot two lines, corresponding to the region of the curve before the bend (primarily the elastics), and the region after the bend (primarily the nonwovens). Read the extension at which these two lines intersect, and calculate the % Pre-Strain from the extension and the corrected gage length. Record as % Pre-strain 0.1%. Calculate the arithmetic mean of three replicate samples for each elastomeric laminate and Average-Pre-Strain to the nearest 0.1%.

Localized Basis Weight

Localized basis weight of the nonwoven fabric may be determined by several available techniques, but a simple representative technique involves cutting a sample piece of the web representing the selected region from the overall area of a nonwoven fabric. The sample piece is then weighed and divided by its area to yield the localized basis weight of the nonwoven fabric in, units of grams per square meter (gsm). Results are reported as a mean of 2 samples per selected region.

Micro-CT Intensive Property Measurement Method

The micro-CT intensive property measurement method measures the basis weight, thickness and volumetric density values within visually discernable regions of a sample of nonwoven web material. It is based on analysis of a 3D x-ray sample image obtained on a micro-CT instrument (a suitable instrument is the Scanco µCT 50 available from Scanco Medical AG, Switzerland, or equivalent). The micro-CT instrument is a cone beam microtomograph with a shielded cabinet. A maintenance free x-ray tube is used as the source with an adjustable diameter focal spot. The x-ray beam passes through the sample, where some of the x-rays are attenuated by the sample. The extent of attenuation correlates to the mass of material the x-rays have to pass through. The transmitted x-rays continue on to the digital detector array and generate a 2D projection image of the sample. A 3D image of the sample is generated by collecting several individual projection images of the sample as it is rotated, which are then reconstructed into a single 3D image. The instrument is interfaced with a computer running software to control the image acquisition and save the raw data. The 3D image is then analyzed using image analysis software (a suitable image analysis software is MATLAB available from The Mathworks, Inc., Natick, MA, or equivalent) to measure the basis weight, thickness and volumetric density intensive properties of regions within the sample.

Sample Preparation

To obtain a sample for measurement, lay a single layer of the nonwoven web material of interest out flat on a work surface, and die cut therefrom a circular piece with a diameter of 30 mm.

If the substrate material is a layer of an absorbent article, for example a topsheet, backsheet nonwoven, acquisition layer, distribution layer, or other component layer; tape the absorbent article to a rigid flat surface in a planar configuration. Carefully separate the individual substrate layer from the absorbent article. A scalpel and/or cryogenic spray (to substantially deactivate adhesives) (such as Cyto-Freeze, Control Company, Houston TX) may be used as necessary to remove a substrate layer from additional underlying layers, if necessary, to avoid any longitudinal and lateral extension of the material. Once the substrate layer has been removed from the article proceed with die cutting the sample as described above.

A sample may be cut from any location containing the zone to be analyzed. Within a zone, regions to be analyzed are ones associated with an ordered arrangement as defined herein. The zone includes a least two regions. A zone and regions thereof may be visually discernible or otherwise identifiable due to changes in fiber and/or filament area density, basis weight, opacity, caliper/thickness or z-direction elevation. Regions within different samples taken from the same substrate material may be analyzed and compared to each other. Care should be taken to avoid folds, wrinkles or tears when selecting a location on the nonwoven web material of interest for sampling.

Image Acquisition

Set up and calibrate the micro-CT instrument according to the manufacturer's specifications. Place the sample into the appropriate holder, between two rings of low density material, which have an inner diameter of 25 mm. This will allow the central portion of the sample to lay horizontal and be scanned without having any other materials directly adjacent to its upper and lower surfaces. Measurements should be taken in this region. The 3D image field of view is approximately 35 mm on each side in the x-y plane with a resolution of approximately 5000 by 5000 pixels, and with a sufficient number of 7 micron thick slices collected to fully include the z-direction of the sample. The reconstructed 3D image resolution contains isotropic voxels of 7 microns. Images are acquired with the source at 45 kVp and 133 µA with no additional low energy filter. These current and voltage settings may be optimized to produce the maximum contrast in the projection data with sufficient x-ray penetration through the sample, but once optimized held constant for all substantially similar samples. A total of 1500 projections images are obtained with an integration time of 1000 ms and 3 averages. The projection images are reconstructed into the 3D image, and saved in 16-bit RAW format to preserve the full detector output signal for analysis.

Image Processing

Load the 3D image into the image analysis software. Threshold the 3D image at a value which separates, and removes, the background signal due to air, but maintains the signal from the sample fibers within the substrate.

Three 2D intensive property images are generated from the threshold 3D image. The first is the Basis Weight Image. To generate this image, the value for each voxel in an x-y plane slice is summed with all of its corresponding voxel values in the other z-direction slices containing signal from the sample. This creates a 2D image where each pixel now has a value equal to the cumulative signal through the entire sample.

In order to convert the raw data values in the Basis Weight Image into real values a basis weight calibration curve is generated. Obtain a substrate that is of substantially similar composition as the sample being analyzed and has a uniform basis weight. Follow the procedures described above to obtain at least ten replicate samples of the calibration curve substrate. Accurately measure the basis weight, by taking the mass to the nearest 0.0001 g and dividing by the sample area and converting to grams per square meter (gsm), of each of the single layer calibration samples and calculate the average to the nearest 0.01 gsm. Following the procedures described above, acquire a micro-CT image of a single layer of the calibration sample substrate. Following the procedure described above, process the micro-CT image, and generate a Basis Weight Image containing raw data values. The real basis weight value for this sample is the average basis weight value measured on the calibration samples. Next, stack two layers of the calibration substrate samples on top of each other, and acquire a micro-CT image of the two layers of calibration substrate. Generate a basis weight raw data image of both layers together, whose real basis weight value is equal to twice the average basis weight value measured on the calibration samples. Repeat this procedure of stacking single layers of the calibration substrate, acquiring a micro-CT image of all of the layers, generating a raw data basis weight image of all of the layers, the real basis weight value of which is equal to the number of layers times the average basis weight value measured on the calibration samples. A total of at least four different basis weight calibration images are obtained. The basis weight values of the calibration samples must include values above and below the basis weight values of the original sample being analyzed to ensure an accurate calibration. The calibration curve is generated by performing a linear regression on the raw data versus the real basis weight values for the four calibration samples. This linear regression must have an R2 value of at least 0.95, if not repeat the entire calibration procedure. This calibration curve is now used to convert the raw data values into real basis weights.

The second intensive property 2D image is the Thickness Image. To generate this image the upper and lower surfaces of the sample are identified, and the distance between these surfaces is calculated giving the sample thickness. The upper surface of the sample is identified by starting at the uppermost z-direction slice and evaluating each slice going through the sample to locate the z-direction voxel for all pixel positions in the x-y plane where sample signal was first detected. The same procedure is followed for identifying the lower surface of the sample, except the z-direction voxels located are all the positions in the x-y plane where sample signal was last detected. Once the upper and lower surfaces have been identified they are smoothed with a 15×15 median filter to remove signal from stray fibers. The 2D Thickness Image is then generated by counting the number of voxels that exist between the upper and lower surfaces for each of the pixel positions in the x-y plane. This raw thickness value is then converted to actual distance, in microns, by multiplying the voxel count by the 7 μm slice thickness resolution.

The third intensive property 2D image is the Volumetric Density Image. To generate this image divide each x-y plane pixel value in the Basis Weight Image, in units of gsm, by the corresponding pixel in the Thickness Image, in units of microns. The units of the Volumetric Density Image are grams per cubic centimeter (g/cc).

Micro-CT Basis Weight, Thickness and Volumetric Density Intensive Properties

Begin by identifying the region to be analyzed. A region to be analyzed is one associated with a zone. The zone includes a least two regions. A zone and regions thereof, may be visually discernible or otherwise identifiable due to changes in fiber and/or filament area density, basis weight, opacity, caliper/thickness or z-direction elevation. Next, identify the boundary of the region to be analyzed. The boundary of a region is identified by visual discernment of differences in intensive properties when compared to other regions within the sample. For example, a region boundary may be identified based by visually discerning a thickness/caliper difference when compared to another region in the sample. Any of the intensive properties may be used to discern region boundaries on either the physical sample itself of any of the micro-CT intensive property images. Once the boundary of the region has been identified, draw an oval or circular "region of interest" (ROI) within the interior of the region. The ROI should have an area of at least 0.1 mm², and be selected to measure an area with intensive property values representative of the identified region. From each of the three intensive property images calculate the average basis weight, thickness and volumetric density within the ROI. Record these values as the region's basis weight to the nearest 0.01 gsm, thickness to the nearest 0.1 micron and volumetric density to the nearest 0.0001 g/cc.

General Examples

In view of the foregoing description, the following general, non-limiting examples of products and configurations and combinations thereof are contemplated:

1. A stretch laminate for a wearable article, comprising an outward-facing layer (610), a wearer-facing layer (620), and an elastic material (630) sandwiched between the outward-facing layer and the wearer-facing layer, the elastic material having been pre-strained by a pre-strain percentage along a stretch direction during manufacture of the laminate, such that when the stretch laminate is in a relaxed condition the outward-facing layer and the wearer-facing layer are gathered along the stretch direction, wherein the outward-facing layer is formed of a section of nonwoven web material comprising an accumulation of filaments (122) and has an inner surface (123) and an outer surface (124), the outer surface comprising an ordered arrangement of zones (160) each zone comprising an attenuated region (272) adjacent to a build-up region (271), wherein the attenuated region has a first basis weight and the build-up region has a second basis weight, wherein the first basis weight is less than the second basis weight, the difference in basis weight corresponding to disposition of the filaments according to the ordered arrangement.

2. A stretch laminate for a wearable article, comprising an outward-facing layer (610), a wearer-facing layer (620), and an elastic material (630) sandwiched between the outward-facing layer and the wearer-facing layer, the elastic material having been pre-strained by a pre-strain percentage along a stretch direction during manufacture of the laminate, such that when the stretch laminate is in a relaxed condition the outward-facing layer and the wearer-facing layer are gathered along the stretch direction, wherein the outward-facing layer is formed of a section of nonwoven web material comprising an accumulation of filaments and has an inner surface (123) and an outer surface (124), wherein the nonwoven web material has been formed via continuous deposition of spun filaments (122) onto a continuous forming belt (260) having an outer receiving side (260a) and an inner side (260b) and moving along a machine direction through a working location (561), to form a batt (270) of filaments deposited on the receiving side (260a) of the forming belt (260), the forming belt (260) comprising an airflow permeable substrate belt (261) and an ordered arrangement of airflow blocking structures (262) disposed on the substrate belt, thereby imparting to the forming belt an ordered arrangement of airflow-permeable regions (263) and airflow-blocked regions (264) coextensive with the airflow blocking structures, the airflow blocking structures (262) extending in a z-direction outward from the substrate belt (261) so has to have a z-direction depth on the receiving side (260a) of the forming belt (260);

wherein before and as they contact the forming belt the filaments are entrained in air flow directed at and through the belt generally along a z-direction, such that the filaments accumulate on the forming belt (260) to a greater weight over the airflow-permeable regions (263) and to a lesser weight over the airflow-blocked regions (264), to create build-up regions (271) of the batt over the airflow-permeable portions and attenuated regions (272) of the batt over the airflow-blocked regions;

wherein the batt (270) is consolidated into a nonwoven web material following its formation on the forming belt;

whereby the attenuated regions form one or more z-direction depressions predominately in the outer surface of the section of nonwoven web material.

3. The stretch laminate of either of the preceding examples wherein the attenuated region(s) and the build-up region(s) comprised by the zone(s), and the zone(s) itself (themselves), are visually discernible.

4. The stretch laminate of any of the preceding examples wherein the elastic material comprises a plurality of elastic strands spaced apart from each other in a cross-stretch direction.

5. The stretch laminate of example 4 wherein the elastic strands have an Average-Strand-Spacing no greater than 3.0 mm, more preferably no greater than 2.0 mm, even more preferably no greater than 1.0 mm, even more preferably no greater than 0.8 mm, and still more preferably no greater than 0.5 mm.

6. The stretch laminate of examples 4 or 5 wherein the elastic strands have an Average Decitex no greater than 300, more preferably no greater than 200, even more preferably no greater than 150, and still more preferably no greater than 100.

7. The stretch laminate of any of examples 4-6 wherein the percentage of pre-strain is an Average-Pre-Strain and the Average-Pre-Strain is no greater than 250 percent, more preferably no greater than 200 percent, even more preferably no greater than 150 percent, and still more preferably no greater than 100 percent.

8. The stretch laminate of example 4 wherein the elastic strands have an Manufacturing-Strand-Spacing no greater than 3.0 mm, more preferably no greater than 2.0 mm, even more preferably no greater than 1.0 mm, and still more preferably no greater than 0.8 mm.

9. The stretch laminate of either of examples 4 or 8 wherein the percentage of pre-strain is a Manufacturing Pre-Strain, and the elastic strands have been joined with the outward-facing layer under a Manufacturing Pre-Strain no greater than 250 percent, more preferably no greater than 200 percent, even more preferably no greater than 150 percent, and still more preferably no greater than 100 percent.

10. The stretch laminate of any of examples 4, 8 or 9 wherein the percentage of pre-strain is a Manufacturing Pre-Strain, and the elastic strands have been joined with the outward-facing layer under a Manufacturing Pre-Strain no greater than 250 percent, more preferably no greater than 200 percent, even more preferably no greater than 150 percent, and still more preferably no greater than 100 percent.

11. The stretch laminate of any of the preceding examples wherein in the outward-facing layer apart from the laminate, at least some of the zones repeat along the stretch direction at a repeat interval.

12. The stretch laminate of example 10 wherein the repeat interval is sufficient in combination with the pre-strain percentage to cause the repeat interval to be gathered in the relaxed laminate to a gathered repeat interval no less than 5.0 mm for the at least some of the zones.

13. The stretch laminate of any of the preceding examples wherein the outward-facing layer bears a pattern of outward-facing layer bonds distinct from any pattern of zones in the ordered arrangement.

14. The stretch laminate of any of the preceding examples wherein the outward-facing layer is formed at least in part of filaments spun from resin comprising polypropylene and a melt additive.

15. The stretch laminate of example 13 wherein the melt additive is selected from the group consisting of erucamide, stearamide, oleamide, silicones and combinations thereof.

16. The stretch laminate of any of the preceding examples wherein the outward-facing layer is formed at least in part of bicomponent filaments.

17. The stretch laminate of example 15 wherein the bicomponent filaments have a core-sheath configuration.

18. The stretch laminate of example 15 wherein the bicomponent filaments have a side-by-side configuration.

19. The stretch laminate of any of examples 15-17 wherein the bicomponent filaments have a first component comprising polypropylene and a second component comprising polyethylene.

20. The stretch laminate of any of the preceding examples wherein the outer surface of the outward-facing layer exhibits an outer percent contact area of from about 20 percent to about 40 percent, and the wearer-facing layer has a wearer-facing surface that exhibits an inner percent contact area that is at least 1.25 times, more preferably at least about 1.50 times, even more preferably at least about 1.75 times, and still more preferably at least about 2.0 times, the outer percent contact area.

21. The stretch laminate of any of the preceding examples wherein the wearer-facing layer comprises a section of wearer-facing nonwoven material.

22. The stretch laminate of example 21 wherein the wearer-facing nonwoven material has a predominately random distribution of fibers or filaments.

23. The stretch laminate of either of examples 21 or 22 wherein the wearer-facing nonwoven material has an overall third basis weight that is less than the second basis weight.

24. The stretch laminate of any of examples 21-23 wherein the wearer-facing nonwoven material bears a pattern of wearer-facing layer bonds.

25. The stretch laminate of any of the preceding examples wherein one or more of the outward-facing layer (610), wearer-facing layer (620), and elastic material (630) comprises a pigmenting or opacifying agent.

26. The stretch laminate of example 25 wherein either or both of the wearer-facing layer (620) and elastic material (630) comprises a non-white pigmenting agent.

27. The stretch laminate of either of examples 25 or 26 wherein the outward-facing layer (610) comprises filaments comprising a white pigmenting agent and/or a blue pigmenting agent.

28. The stretch laminate of any of examples 25-27 wherein the outward-facing layer (610) comprises a first deposition of filaments comprising a first pigmenting agent or first combination of pigmenting agents, and a second deposition of filaments comprising a second pigmenting agent or second combination of pigmenting agents, wherein the first pigmenting agent or first combination of pigmenting agents differs from the second pigmenting agent or second combination of pigmenting agents in one or more of particular pigmenting agents included and weight concentrations thereof.

29. The stretch laminate of any of the preceding examples wherein the outward-facing layer (610) and the wearer-facing layer (620) are bonded together about the elastic material (630) at least in part by an adhesive.

30. The stretch laminate of example 29 wherein the outward-facing layer (610) and the wearer-facing layer (620) are bonded together about the elastic material (630) by an adhesive along a portion but not an entirety of the x-y plane surface area of the laminate.

31. The stretch laminate of any of the preceding examples wherein the outward-facing layer (610) and the wearer-facing layer (620) are bonded together about the elastic material (630) at least in part by a pattern of laminate thermal bonds in which materials respectively comprised by the outward facing layer and the wearer-facing layer are thermally fused.

32. The stretch laminate of any of examples 29-31 wherein the outward-facing layer (610) and the wearer-facing layer (620) are bonded together about the elastic material (630) by a pattern of laminate thermal bonds in which materials respectively comprised by the outward facing layer and the wearer-facing layer are thermally fused, along a portion but not an entirety of the x-y plane surface area of the laminate.

33. The stretch laminate of any of examples 29-32 wherein the outward-facing layer (610) and the wearer-facing layer (620) are bonded together about the elastic material (630) by a pattern of laminate thermal bonds in which materials respectively comprised by the outward facing layer and the wearer-facing layer are thermally fused, exclusively along a first portion of the x-y plane surface area of the laminate; and the outward-facing layer (610) and the wearer-facing layer (620) are bonded together about the elastic material (630) by an adhesive exclusively along a second portion of the x-y plane surface area of the laminate.

34. The stretch laminate of any of the preceding examples wherein the outward-facing layer comprises a first area (710) occupied by the ordered arrangement of zones and a second area (720), the second area being distinguishable from the first area by an absence of an attenuated region over a continuous surface area of the outward-facing layer in its ungathered condition, equal to or greater than approximately 4 cm² and having no dimension in the x-y plane smaller than approximately 1 cm, the second area being delineated from the first area by a perimeter demarking a discontinuity or interruption in the arrangement of zones.

35. The stretch laminate of example 34 wherein the second area has an average basis weight that is less than the second basis weight and greater than the first basis weight.

36. The stretch laminate of either of examples 34 or 35 wherein the outward-facing layer (610) and the wearer-facing layer (620) are bonded together about the elastic material (630) at least in part by a pattern of laminate thermal bonds in which materials respectively comprised by the outward facing layer and the wearer-facing layer are thermally fused, wherein thermal bonds of the pattern are present in a greater number of bonds per unit surface area in the second area, and in a lesser number of bonds per unit surface area in the first area, or thermal bonds are substantially absent in the first area.

37. The stretch laminate of either of examples 35 or 36 wherein the outward-facing layer (610) and the wearer-facing layer (620) are bonded together about the elastic material (630) at least in part by an adhesive in the first area.

38. A disposable absorbent pant having a waist-surrounding belt portion formed at least in part of the stretch laminate any of the preceding examples.

39. A disposable absorbent pant having a waist-surrounding belt portion formed at least in part of the stretch laminate of any of examples 34-37, wherein the belt portion forms at least in part a waist opening edge and/or leg opening edges of the pant, and wherein the second area is disposed along the waist opening edge and/or a leg opening edge.

40. A disposable absorbent pant having a waist-surrounding belt portion with front and rear belt portions formed of the stretch laminate of any of examples 35-38, wherein the second area is continuous across a majority or substantially all of a width of one or both of front and rear belt portions.

Additionally, the following general, non-limiting examples of methods are contemplated:

1. A method for manufacturing a stretch laminate (600) useful as a component of a wearable article, comprising the steps of:

providing a continuous forming belt (260) cycling about a set of guide rollers (562), the forming belt (260) comprising an outer receiving side (260a) and an inner side (260b), and comprising an air permeable substrate belt (261) with an ordered arrangement of airflow blocking structures (262) disposed thereon, the airflow blocking structures (262) projecting in a z-direction outward from the substrate belt (261) and having outermost land surfaces (262a) and a z-direction depth on the receiving side (260a) of the forming belt (260), whereby the belt has an arrangement of airflow permeable regions (263) and airflow blocked regions (264) corresponding with the ordered arrangement of airflow blocking structures (262);

providing a forming vacuum system (555) below a working location (561) of travel of the forming belt and proximate its inner side (260b), wherein the forming belt (260) moves in a machine direction MD through the working location (561);

continuously introducing and entraining a flow of individual polymer streams (122a) into an air flow moving generally in a z-direction with respect to the working region (561) of the forming belt (260);

continuously attenuating the polymer streams (122a) via the air flow, to form spun filaments (122);

continuously directing the air flow and entrained spun filaments (122) to the working location (561);

using the forming vacuum system (555) to continuously draw air in the air flow through the airflow permeable regions (263) of the forming belt (260) as they move along the machine direction through the working location (561), and thereby drawing the entrained filaments (122) predominately toward and onto the airflow permeable regions (263), such that they accumulate in greater weight over the airflow permeable regions (263) and in lesser weight over the airflow blocked regions (262), to form a batt (270) of accumulated filaments (122) on the receiving side (260a) of the forming belt (260), whereby the batt is provided with an arrangement of build-up regions (271) and attenuated regions (272) corresponding with the ordered arrangement of airflow blocking structures (262) on the forming belt (260);

compacting the batt against the forming belt (260) via a compaction roller (570), whereby filaments in the attenuated regions (272) are deformed by pressure between the land surfaces (262a) and the compaction roller (570); and lifting the batt (270) away from the forming belt (260);

further consolidating the batt (270) to form a consolidated nonwoven web material (280) having an ordered arrangement of the build-up regions (271) and attenuated regions (272) corresponding with the ordered arrangement of airflow blocking structures (262) on the forming belt (260); and manufacturing the stretch laminate, by the steps of:

providing the consolidated nonwoven web material (280) to form an outward-facing layer (610) of the stretch laminate;

providing an elastic material (630), and pre-straining the elastic material along a stretch direction;

providing a second web material to form a wearer-facing layer (620) of the stretch laminate;

sandwiching the elastic material (630) in the pre-strained condition, between the outward-facing layer (610) and the wearer-facing layer (620);

affixing the outward-facing layer (610), the elastic material (630) and the wearer-facing layer (620) together to form the stretch laminate (600).

2. The method of example 1 further comprising conveying the batt through a nip (571*a*) between a pair of calender bonding rollers (571, 573) thereby consolidating the batt and imparting a pattern of bonds to the batt to form a consolidated, calender bonded nonwoven web material.

3. The method of either of the preceding examples wherein the elastic material comprises a film.

4. The method of either of examples 1 or 2 wherein the elastic material comprises a plurality of elastic strands substantially aligned with the stretch direction and spaced apart in a cross-stretch direction.

5. The method of example 5 wherein the elastic material comprises beamed elastics.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention.

Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A stretch laminate for a wearable article, comprising an outward-facing layer, a wearer-facing layer, and an elastic material sandwiched between the outward-facing layer and the wearer-facing layer, the elastic material having been pre-strained by a pre-strain percentage along a stretch direction during manufacture of the laminate, such that when the stretch laminate is in a relaxed condition the outward-facing layer and the wearer-facing layer are gathered along the stretch direction, wherein the outward-facing layer is formed of a section of nonwoven web material comprising an accumulation of filaments and has an inner surface and an outer surface, the outer surface comprising an ordered arrangement of zones each zone comprising an attenuated region adjacent to a build-up region, wherein the attenuated region has a first basis weight and the build-up region has a second basis weight, wherein the first basis weight is less than the second basis weight, the difference in basis weight corresponding to disposition of the filaments according to the ordered arrangement, wherein the outward-facing layer comprises a first area and a second area, the first area being occupied by the ordered arrangement of zones and the second area being distinguishable from the first area by an absence of an attenuated region over a continuous surface area of the outward-facing layer in its ungathered condition, the continuous surface area being equal to or greater than approximately 4 cm$^2$ and having no dimension in the x-y plane smaller than approximately 1 cm, the second area being delineated from the first area by a perimeter demarking a discontinuity or interruption in the arrangement of zones; and wherein the outward-facing layer is bonded about the elastic material to the wearer-facing layer in the second area by adhesive positioned on the outward-facing layer and the wearer-facing layer.

2. The stretch laminate of claim 1, wherein the nonwoven web material has been formed via continuous deposition of spun filaments onto a continuous forming belt having an outer receiving side and an inner side and moving along a machine direction through a working location, to form a batt of filaments deposited on the receiving side of the forming belt, the forming belt comprising an airflow permeable substrate belt and an ordered arrangement of airflow blocking structures disposed on the substrate belt, thereby imparting to the forming belt an ordered arrangement of airflow-permeable regions and airflow-blocked regions coextensive with the airflow blocking structures, the airflow blocking structures extending in a z-direction outward from the substrate belt so has to have a z-direction depth on the receiving side of the forming belt;

wherein before and as they contact the forming belt the filaments are entrained in air flow directed at and through the belt generally along a z-direction, such that the filaments accumulate on the forming belt to a greater weight over the airflow-permeable regions and to a lesser weight over the airflow-blocked regions, to create build-up regions of the batt over the airflow-permeable portions and attenuated regions of the batt over the airflow-blocked regions;

wherein the batt is consolidated into a nonwoven web material following its formation on the forming belt;

whereby the attenuated regions form one or more z-direction depressions predominately in the outer surface of the section of nonwoven web material.

3. The stretch laminate of claim 1 wherein the attenuated region(s) and the build-up region(s) comprised by the zone(s), and the zone(s) itself (themselves), are visually discernible.

4. The stretch laminate of claim 1 wherein the elastic material comprises a plurality of elastic strands spaced apart from each other in a cross-stretch direction.

5. The stretch laminate of claim 4 wherein the elastic strands have an Average-Strand-Spacing no greater than 3.0 mm.

6. The stretch laminate of claim 5 wherein the elastic strands have an Average Decitex no greater than 300.

7. The stretch laminate of claim 5 wherein the pre-strain percentage is an Average-Pre-Strain and the Average-Pre-Strain is no greater than 250 percent.

8. The stretch laminate of claim 4 wherein the elastic strands have a Manufacturing-Strand-Spacing no greater than 3.0 mm.

9. The stretch laminate of claim 4 wherein the pre-strain percentage is a Manufacturing Pre-Strain, and the elastic strands have been joined with the outward-facing layer under a Manufacturing Pre-Strain no greater than 250 percent.

10. The stretch laminate of claim 1 wherein the outward-facing layer is formed at least in part of filaments spun from resin comprising polypropylene and a melt additive.

11. The stretch laminate of claim 10 wherein the melt additive is selected from the group consisting of erucamide, stearamide, oleamide, silicones and combinations thereof.

12. The stretch laminate of claim 1 wherein the outward-facing layer is formed at least in part of bicomponent filaments.

13. The stretch laminate of claim 12 wherein the bicomponent filaments have a core-sheath configuration.

14. The stretch laminate of claim 12 wherein the bicomponent filaments have a side-by-side configuration.

15. The stretch laminate of claim 12 wherein the bicomponent filaments have a first component comprising polypropylene and a second component comprising polyethylene.

16. The stretch laminate of claim 1 wherein the outer surface of the outward-facing layer exhibits an outer percent contact area of from about 20 percent to about 40 percent, in accordance with the Percent Surface Contact Area Method described herein, and the wearer-facing layer has a wearer-facing surface that exhibits an inner percent contact area that is at least 1.25 times the outer percent contact area.

* * * * *